US012760105B2

(12) United States Patent
Chang et al.

(10) Patent No.: US 12,760,105 B2

(45) **Date of Patent: *Oct. 13, 2026**

(54) MULTI-SPECIFIC BINDING PROTEINS BINDING BCMA, NKG2D AND CD16 AND METHODS OF USE

(71) Applicant: Dragonfly Therapeutics, LLC, Waltham, MA (US)

(72) Inventors: Gregory P. Chang, Medford, MA (US); Ann F. Cheung, Lincoln, MA (US); William Haney, Wayland, MA (US); Bradley M. Lunde, Lebanon, NH (US); Bianka Prinz, Lebanon, NH (US)

(73) Assignee: Dragonfly Therapeutics, LLC, Waltham, MA (US)

(*) Notice: Subject to any disclaimer, the term of this patent is extended or adjusted under 35 U.S.C. 154(b) by 41 days.

This patent is subject to a terminal disclaimer.

(21) Appl. No.: 16/484,936

(22) PCT Filed: Feb. 9, 2018

(86) PCT No.: PCT/US2018/017653

§ 371 (c)(1),
(2) Date: Aug. 9, 2019

(87) PCT Pub. No.: WO2018/148566

PCT Pub. Date: Aug. 16, 2018

(65) Prior Publication Data

US 2019/0375838 A1 Dec. 12, 2019

Related U.S. Application Data

(60) Provisional application No. 62/457,780, filed on Feb. 10, 2017.

(51) Int. Cl.
*C07K 16/28* (2006.01)

(52) U.S. Cl.
CPC ........ *C07K 16/283* (2013.01); *C07K 16/2878* (2013.01); *C07K 2317/31* (2013.01); (Continued)

(58) Field of Classification Search
None
See application file for complete search history.

(56) References Cited

U.S. PATENT DOCUMENTS

| | | | |
|---|---|---|---|
| 5,776,427 | A | 7/1998 | Thorpe et al. |
| 5,807,706 | A | 9/1998 | Carter et al. |

(Continued)

FOREIGN PATENT DOCUMENTS

| | | | |
|---|---|---|---|
| CA | 2990511 | | 12/2016 |
| CN | 101945893 | A | 1/2011 |

(Continued)

OTHER PUBLICATIONS

Chen et al., Enhancement and destruction of antibody function by somatic mutation: unequal occurrence is controlled by V gene combinatorial association, EMBO J. 14(12):2784-2794, 1995.*

(Continued)

*Primary Examiner* — Claire Kaufman

(74) *Attorney, Agent, or Firm* — Goodwin Procter LLP

(57) ABSTRACT

Multi-specific binding proteins that bind BCMA, the NKG2D receptor, and CD 16 are described, as well as pharmaceutical compositions and therapeutic methods useful for the treatment of cancer.

20 Claims, 22 Drawing Sheets

Specification includes a Sequence Listing.

(52) U.S. Cl.
CPC .... *C07K 2317/33* (2013.01); *C07K 2317/526* (2013.01); *C07K 2317/55* (2013.01); *C07K 2317/622* (2013.01); *C07K 2317/624* (2013.01); *C07K 2317/64* (2013.01); *C07K 2317/73* (2013.01); *C07K 2317/76* (2013.01); *C07K 2317/92* (2013.01); *C07K 2317/94* (2013.01); *C07K 2319/03* (2013.01); *C07K 2319/30* (2013.01); *C07K 2319/33* (2013.01)

(56) References Cited

U.S. PATENT DOCUMENTS 5,863,538 A 1/1999 Thorpe et al.
5,959,084 A 9/1999 Ring et al.
6,036,955 A 3/2000 Thorpe et al.
6,129,914 A 10/2000 Weiner et al.
6,210,670 B1 4/2001 Berg
6,294,167 B1 9/2001 Lindhofer et al.
6,572,856 B1 6/2003 Taylor et al.
6,737,056 B1 5/2004 Presta
7,112,324 B1 9/2006 Dorken et al.
7,235,641 B2 6/2007 Kufer et al.
7,575,923 B2 8/2009 Dorken et al.
7,635,472 B2 12/2009 Kufer et al.
7,642,228 B2 1/2010 Carter et al.
7,695,936 B2 4/2010 Carter et al.
7,820,166 B2 10/2010 Lanzavecchia
7,879,985 B2 2/2011 Urso et al.
7,951,917 B1 5/2011 Arathoon et al.
8,007,796 B2 8/2011 Baeuerle et al.
8,076,459 B2 12/2011 Hofmeister et al.
8,101,722 B2 1/2012 Kufer et al.
8,236,308 B2 8/2012 Kischel et al.
8,409,577 B2 4/2013 Thompson et al.
8,518,403 B2 8/2013 Hoffmann et al.
8,592,562 B2 * 11/2013 Kannan .................. A61P 37/04 530/387.3
8,593,562 B2 * 11/2013 Ernst ..................... G02B 27/46 359/569
8,658,765 B2 2/2014 Martin, Jr. et al.
8,679,785 B2 3/2014 Carter et al.
8,759,494 B2 6/2014 Bachmann
8,784,821 B1 7/2014 Kufer et al.
8,796,420 B2 8/2014 Martin, Jr. et al.
8,840,888 B2 9/2014 Nagorsen et al.
8,931,406 B2 1/2015 Detloff et al.
9,079,969 B2 7/2015 Martin, Jr. et al.
9,102,736 B2 8/2015 Hofmeister et al.
9,127,064 B2 9/2015 Urso et al.
9,150,656 B2 10/2015 Johnson et al.
9,150,663 B2 10/2015 Labrijn et al.
9,200,078 B2 12/2015 Bachmann
9,248,181 B2 2/2016 De Kruif et al.
9,248,182 B2 2/2016 De Kruif et al.
9,273,136 B2 3/2016 Radar et al.
9,334,331 B2 5/2016 Igawa et al.
9,447,185 B2 9/2016 Romagne et al.
9,493,578 B2 11/2016 Lazar et al.
9,562,109 B2 2/2017 Von Kreudenstein et al.
9,587,036 B2 3/2017 Kufer et al.
9,637,557 B2 5/2017 Scheer et al.
9,683,053 B2 * 6/2017 Blein .................. C07K 16/468
9,690,969 B2 6/2017 Okamoto
9,718,893 B2 8/2017 Jung et al.
9,951,145 B2 4/2018 Kim et al.
9,963,513 B2 * 5/2018 Vu .......................... A61P 31/00
9,969,809 B2 5/2018 Kuo et al.
10,040,853 B2 8/2018 Spies et al.
10,047,167 B2 8/2018 Demarest et al.
10,059,765 B2 8/2018 Velardi et al.
10,377,827 B2 * 8/2019 Swanson ................. A61P 19/04
10,421,807 B2 9/2019 Gonzalez et al.
10,526,409 B2 1/2020 Urso et al.
10,752,694 B2 8/2020 Kufer et al.
10,767,760 B2 9/2020 Ando
11,084,880 B2 * 8/2021 Brogdon ................. A61P 35/02
11,124,582 B2 9/2021 Ambrogelly et al.
11,787,864 B2 10/2023 Cheung et al.
11,834,506 B2 12/2023 Chang et al.
11,884,732 B2 1/2024 Chang et al.
11,884,733 B2 1/2024 Chang et al.
11,939,384 B1 3/2024 Chang et al.
2002/0103345 A1 8/2002 Zhu
2002/0193569 A1 12/2002 Hanna
2003/0095965 A1 5/2003 Van Beneden et al.
2004/0038339 A1 2/2004 Kufer et al.
2004/0052783 A1 3/2004 Weiner et al.
2004/0115198 A1 6/2004 Spies et al.
2005/0037002 A1 2/2005 Velardi et al.
2005/0054019 A1 3/2005 Michaud et al.
2005/0058639 A1 3/2005 Gudas et al.
2005/0158307 A1 7/2005 Spies et al.
2005/0244416 A1 11/2005 Jung
2006/0018899 A1 1/2006 Kao et al.
2006/0235201 A1 10/2006 Kischel
2006/0246004 A1 11/2006 Adams et al.
2007/0004909 A1 1/2007 Johnson et al.
2007/0071759 A1 3/2007 Shin et al.
2007/0179086 A1 8/2007 Gliniak et al.
2007/0190063 A1 8/2007 Bahjat et al.
2008/0025975 A1 1/2008 Weiner et al.
2008/0299137 A1 12/2008 Svendsen et al.
2008/0305105 A1 12/2008 Kufer et al.
2009/0142352 A1 6/2009 Jackson et al.
2009/0175867 A1 7/2009 Thompson et al.
2009/0226442 A1 9/2009 Huet et al.
2009/0226466 A1 9/2009 Fong et al.
2009/0252729 A1 10/2009 Farrington et al.
2009/0304693 A1 12/2009 Ghayur et al.
2009/0304696 A1 12/2009 Lawson et al.
2010/0009866 A1 1/2010 Prinz et al.
2010/0055034 A1 3/2010 Martin et al.
2010/0056764 A1 3/2010 Urso et al.
2010/0124764 A1 5/2010 Hufton et al.
2010/0174053 A1 7/2010 Johnson et al.
2010/0178298 A1 7/2010 Lindhofer
2010/0260765 A1 10/2010 Barry et al.
2010/0272718 A1 10/2010 Urso et al.
2010/0286374 A1 11/2010 Kannan et al.
2010/0291112 A1 11/2010 Kellner et al.
2010/0310463 A1 12/2010 Cicortas Gunnarsson et al.
2011/0008335 A1 1/2011 Velardi et al.
2011/0008355 A1 1/2011 Velardi et al.
2011/0020273 A1 1/2011 Chang et al.
2011/0044980 A1 2/2011 Ghayur et al.
2011/0054151 A1 3/2011 Lazar et al.
2011/0150870 A1 6/2011 Rader et al.
2011/0311535 A1 12/2011 Dranoff et al.
2012/0014957 A1 1/2012 Ghayur et al.
2012/0058082 A1 3/2012 Kaplan et al.
2012/0058906 A1 3/2012 Smider et al.
2012/0093823 A1 4/2012 Van Den Brink et al.
2012/0149876 A1 6/2012 Kreudenstein
2012/0171173 A1 7/2012 Ideno et al.
2012/0195900 A1 8/2012 Ghayur et al.
2012/0263722 A1 10/2012 Ghayur et al.
2012/0269723 A1 10/2012 Brinkmann et al.
2012/0294796 A1 11/2012 Johnson et al.
2012/0294857 A1 11/2012 Sentman et al.
2012/0321626 A1 12/2012 Zhou
2012/0328619 A1 12/2012 Fey et al.
2013/0115208 A1 5/2013 Ho et al.
2013/0177555 A1 7/2013 Wilkinson et al.
2013/0209514 A1 8/2013 Gilboa et al.
2013/0216528 A1 8/2013 Cheung et al.
2013/0216544 A1 8/2013 Bachmann
2013/0230525 A1 9/2013 Li et al.
2013/0336977 A1 12/2013 Thompson et al.
2014/0044739 A1 2/2014 Teng et al.
2014/0072579 A1 3/2014 De Kruif et al.
2014/0072581 A1 3/2014 Dixit et al.
2014/0105889 A1 4/2014 Igawa et al.
2014/0105915 A1 4/2014 Algate et al.
2014/0112926 A1 4/2014 Liu et al.

(56) References Cited

U.S. PATENT DOCUMENTS

| | | | |
|---|---|---|---|
| 2014/0120096 | A1 | 5/2014 | Bakker et al. |
| 2014/0127203 | A1 | 5/2014 | Thompson et al. |
| 2014/0140999 | A1 | 5/2014 | De Kruif et al. |
| 2014/0141022 | A1 | 5/2014 | Thompson et al. |
| 2014/0154250 | A1 | 6/2014 | Thompson et al. |
| 2014/0154252 | A1 | 6/2014 | Thompson et al. |
| 2014/0199294 | A1 | 7/2014 | Mimoto et al. |
| 2014/0234342 | A1 | 8/2014 | Narni-Mancinelli et al. |
| 2014/0242077 | A1 | 8/2014 | Choi et al. |
| 2014/0271617 | A1 | 9/2014 | Igawa et al. |
| 2014/0288275 | A1 | 9/2014 | Moore et al. |
| 2014/0294827 | A1 | 10/2014 | Gastwirt et al. |
| 2014/0302064 | A1 | 10/2014 | Moore |
| 2014/0363426 | A1 | 12/2014 | Moore et al. |
| 2014/0364340 | A1 | 12/2014 | Vasquez et al. |
| 2014/0377269 | A1 | 12/2014 | Mabry et al. |
| 2015/0050269 | A1 | 2/2015 | Igawa et al. |
| 2015/0056206 | A1 | 2/2015 | Zhou |
| 2015/0079088 | A1 | 3/2015 | Lowman et al. |
| 2015/0119555 | A1 | 4/2015 | Jung et al. |
| 2015/0166636 | A1 | 6/2015 | Igawa et al. |
| 2015/0166654 | A1 | 6/2015 | Igawa et al. |
| 2015/0175697 | A1 | 6/2015 | Bonvini et al. |
| 2015/0175700 | A1 | 6/2015 | Lum et al. |
| 2015/0203591 | A1 | 7/2015 | Yancopoulos et al. |
| 2015/0210765 | A1 | 7/2015 | Roschke et al. |
| 2015/0259431 | A1 | 9/2015 | Stemmer et al. |
| 2015/0259434 | A1 | 9/2015 | Johnson et al. |
| 2015/0274838 | A1 | 10/2015 | Johnson et al. |
| 2015/0299319 | A1 | 10/2015 | Velardi et al. |
| 2015/0307617 | A1 | 10/2015 | Du et al. |
| 2015/0307628 | A1 | 10/2015 | Kim et al. |
| 2015/0329637 | A1 | 11/2015 | Urech et al. |
| 2015/0353636 | A1 | 12/2015 | Parren et al. |
| 2016/0017038 | A1 | 1/2016 | Koenig |
| 2016/0024214 | A1 | 1/2016 | Urso et al. |
| 2016/0032009 | A1 | 2/2016 | Cheung et al. |
| 2016/0039942 | A1 | 2/2016 | Cobbold et al. |
| 2016/0046727 | A1 | 2/2016 | Labrijn et al. |
| 2016/0046730 | A1 | 2/2016 | Ghayur et al. |
| 2016/0077105 | A1 | 3/2016 | Bobrowicz et al. |
| 2016/0090426 | A1 | 3/2016 | Zhou et al. |
| 2016/0096892 | A1 | 4/2016 | Brogdon et al. |
| 2016/0122432 | A1 | 5/2016 | Inserm et al. |
| 2016/0159882 | A1 | 6/2016 | Landgraf et al. |
| 2016/0159924 | A1 | 6/2016 | Padkjaer et al. |
| 2016/0176968 | A1 | 6/2016 | Chang et al. |
| 2016/0289341 | A1 | 10/2016 | Wu |
| 2016/0326249 | A1 | 11/2016 | Ng et al. |
| 2016/0347849 | A1 | 12/2016 | Cai et al. |
| 2016/0369002 | A1 | 12/2016 | Gauthier et al. |
| 2017/0022291 | A1 | 1/2017 | Baruah et al. |
| 2017/0029529 | A1 | 2/2017 | Croasdale et al. |
| 2017/0051068 | A1 | 2/2017 | Pillarisetti et al. |
| 2017/0066827 | A1 | 3/2017 | Pule et al. |
| 2017/0114141 | A1 | 4/2017 | Amann et al. |
| 2017/0233472 | A1 | 8/2017 | Barat et al. |
| 2017/0291955 | A1 | 10/2017 | Li et al. |
| 2017/0362321 | A1 | 12/2017 | Campbell et al. |
| 2017/0368169 | A1* | 12/2017 | Loew ...................... A61P 35/02 |
| 2017/0369595 | A1 | 12/2017 | Brinkmann et al. |
| 2018/0044415 | A1 | 2/2018 | Escarpe et al. |
| 2018/0057608 | A1 | 3/2018 | Jung et al. |
| 2018/0105594 | A1 | 4/2018 | Urso et al. |
| 2018/0105599 | A1 | 4/2018 | Cobbold et al. |
| 2018/0118851 | A1 | 5/2018 | Comeau et al. |
| 2018/0237519 | A1 | 8/2018 | Yu et al. |
| 2018/0237541 | A1 | 8/2018 | Kim et al. |
| 2018/0273633 | A1 | 9/2018 | Jiang et al. |
| 2018/0312592 | A1 | 11/2018 | Junutula et al. |
| 2018/0346600 | A1 | 12/2018 | Kim et al. |
| 2019/0048079 | A1 | 2/2019 | Spies et al. |
| 2019/0225702 | A1 | 7/2019 | Baeuerle et al. |
| 2019/0352427 | A1 | 11/2019 | Vu et al. |
| 2019/0359716 | A1 | 11/2019 | Chang et al. |
| 2019/0375838 | A1 | 12/2019 | Chang et al. |
| 2020/0002436 | A1 | 1/2020 | Chang et al. |
| 2020/0024353 | A1 | 1/2020 | Chang et al. |
| 2020/0048347 | A1 | 2/2020 | Miao et al. |
| 2020/0055939 | A1 | 2/2020 | Lombana et al. |
| 2020/0095327 | A1 | 3/2020 | Chang et al. |
| 2020/0157174 | A1 | 5/2020 | Chang et al. |
| 2020/0157226 | A1 | 5/2020 | Chang et al. |
| 2020/0157227 | A1 | 5/2020 | Chang et al. |
| 2020/0165344 | A1 | 5/2020 | Chang et al. |
| 2020/0216544 | A1 | 7/2020 | Chang et al. |
| 2020/0231678 | A1 | 7/2020 | Chang et al. |
| 2020/0231679 | A1 | 7/2020 | Chang et al. |
| 2020/0231700 | A1 | 7/2020 | Cheung et al. |
| 2020/0277383 | A1 | 9/2020 | Chang et al. |
| 2020/0277384 | A1 | 9/2020 | Chang et al. |
| 2020/0376034 | A1 | 12/2020 | Chang et al. |
| 2021/0009718 | A1 | 1/2021 | Ambrogelly et al. |
| 2021/0032349 | A1 | 2/2021 | Dengl et al. |
| 2021/0054082 | A1 | 2/2021 | Chang et al. |
| 2021/0070887 | A1 | 3/2021 | Ambrogelly et al. |
| 2021/0079102 | A1 | 3/2021 | Chang et al. |
| 2021/0101976 | A1 | 4/2021 | Chang et al. |
| 2021/0130471 | A1 | 5/2021 | Chang et al. |
| 2021/0130474 | A1 | 5/2021 | Chang et al. |
| 2021/0130496 | A1 | 5/2021 | Chang et al. |
| 2021/0198369 | A1 | 7/2021 | Chang et al. |
| 2021/0206859 | A1 | 7/2021 | Chang et al. |
| 2021/0214436 | A1 | 7/2021 | Chang et al. |
| 2021/0221894 | A1 | 7/2021 | Bigelow et al. |
| 2021/0238290 | A1 | 8/2021 | Chang et al. |
| 2021/0261668 | A1 | 8/2021 | Chang et al. |
| 2021/0292420 | A1 | 9/2021 | Chang et al. |
| 2021/0317223 | A1 | 10/2021 | Bigelow et al. |
| 2021/0363261 | A1 | 11/2021 | Chang et al. |
| 2022/0025037 | A1 | 1/2022 | Baruah et al. |
| 2022/0089760 | A1 | 3/2022 | Bigelow et al. |
| 2022/0119533 | A1 | 4/2022 | Cheung et al. |
| 2022/0119534 | A1 | 4/2022 | Baruah et al. |
| 2022/0153848 | A1 | 5/2022 | Chang et al. |
| 2022/0195065 | A1 | 6/2022 | Chang et al. |
| 2023/0034186 | A1 | 2/2023 | Cuillerot et al. |
| 2023/0203202 | A1 | 6/2023 | Bigelow et al. |
| 2023/0227562 | A1 | 7/2023 | Chang et al. |
| 2023/0250176 | A1 | 8/2023 | Cheung et al. |
| 2023/0257467 | A1 | 8/2023 | Cheung et al. |
| 2023/0272041 | A1 | 8/2023 | Bigelow et al. |
| 2023/0303702 | A1 | 9/2023 | Chang et al. |
| 2023/0357409 | A1 | 11/2023 | Chang et al. |
| 2023/0391877 | A1 | 12/2023 | Chang et al. |
| 2023/0416402 | A1 | 12/2023 | Cuillerot et al. |

FOREIGN PATENT DOCUMENTS

| | | | |
|---|---|---|---|
| CN | 102378768 | A | 3/2012 |
| CN | 105814084 | | 7/2016 |
| CN | 105906722 | | 8/2016 |
| DE | 102013019352 | | 9/2015 |
| EP | 627940 | | 12/1994 |
| EP | 871673 | | 10/1998 |
| EP | 1124568 | | 8/2001 |
| EP | 1769000 | | 4/2007 |
| EP | 2185595 | | 5/2010 |
| EP | 2222706 | | 9/2010 |
| EP | 2927321 | A1 | 10/2015 |
| EP | 2930188 | | 10/2015 |
| EP | 2942629 | | 11/2015 |
| EP | 2982380 | | 2/2016 |
| EP | 2990416 | A1 | 3/2016 |
| KR | 10-2013-0103325 | | 9/2013 |
| KR | 10-2014-0067944 | | 6/2014 |
| RU | 2588668 | C2 | 7/2016 |
| RU | 2593720 | C2 | 8/2016 |
| RU | 2608504 | C2 | 1/2017 |
| TW | 201305207 | | 2/2013 |
| WO | WO 1988/008854 | | 11/1988 |
| WO | WO 1989/006544 | | 7/1989 |
| WO | WO 1996/027011 | | 9/1996 |
| WO | WO 2001/071005 | | 9/2001 |

(56) References Cited

FOREIGN PATENT DOCUMENTS

WO WO 2004/056873 7/2004
WO WO 2005/003172 1/2005
WO WO 2005/009465 2/2005
WO WO 2005/105849 11/2005
WO WO 2006/037960 4/2006
WO WO 2007/002905 1/2007
WO WO 2007/042573 4/2007
WO WO 2007055926 5/2007
WO WO 2007097812 A2 8/2007
WO WO-2009/007124 A1 1/2009
WO WO 2009/077483 6/2009
WO WO 2009/089004 7/2009
WO WO 2010/017103 A2 2/2010
WO WO 2010/080124 A2 7/2010
WO WO 2011/014659 2/2011
WO WO 2011/075636 6/2011
WO WO 2011/076922 6/2011
WO WO 2011/109400 9/2011
WO WO 2011/131746 10/2011
WO WO 2011/143545 11/2011
WO WO 2012006490 A2 1/2012
WO WO 2012/025530 3/2012
WO WO 2012/032080 3/2012
WO WO 2012/034039 3/2012
WO WO 2012/045752 A1 4/2012
WO WO 2012/058768 5/2012
WO WO 2012/115241 8/2012
WO WO 2012125850 A1 9/2012
WO WO-2012/131555 A2 10/2012
WO WO 2015/150477 10/2012
WO WO 2012158818 A2 11/2012
WO WO 2012162482 A1 11/2012
WO WO 2012/163805 12/2012
WO WO 2013/013700 1/2013
WO WO 2013/036799 3/2013
WO WO 2013/072415 A1 5/2013
WO WO-2013063702 5/2013
WO WO 2013/092001 6/2013
WO WO 2013/113615 A1 8/2013
WO WO 2013/192594 12/2013
WO WO 2014/001324 A1 1/2014
WO WO 2014/012085 1/2014
WO WO 2014/079000 5/2014
WO WO 2014/084607 6/2014
WO WO-2014/110601 A1 7/2014
WO WO 2014/122143 8/2014
WO WO 2014/124326 8/2014
WO WO 2014/144763 9/2014
WO WO 2014131712 A1 9/2014
WO WO 2014145806 A2 9/2014
WO WO 2014/165818 10/2014
WO WO 2014159940 A1 10/2014
WO WO 2014/198748 12/2014
WO WO 2015/009856 1/2015
WO WO 2015/036582 3/2015
WO WO 2015/036606 3/2015
WO WO 2015/063187 5/2015
WO WO 2015/070061 5/2015
WO WO 2015/089344 6/2015
WO WO 2015/095412 6/2015
WO WO 2015/095539 6/2015
WO WO 2015/095972 7/2015
WO WO 2015/150447 10/2015
WO WO 2015/153765 A1 10/2015
WO WO 2015/153912 10/2015
WO WO 2015/158636 10/2015
WO WO 2015/169781 11/2015
WO WO 2015/181282 12/2015
WO WO 2015/184203 12/2015
WO WO 2015/184207 12/2015
WO WO 2015/197582 12/2015
WO WO 2015/197593 12/2015
WO WO 2015/197598 12/2015
WO WO 2016/001810 1/2016
WO WO 2016/011571 1/2016
WO WO 2016/028672 2/2016
WO WO 2016023909 A1 2/2016
WO WO 2016025880 A1 2/2016
WO WO 2016/032334 3/2016
WO WO 2016/070959 5/2016
WO WO 2016/087531 6/2016
WO WO 2016/090278 6/2016
WO WO-2016/094304 A2 6/2016
WO WO 2016/097408 6/2016
WO WO 2016/100533 6/2016
WO WO 2016/109774 7/2016
WO WO 2016/115274 7/2016
WO WO 2016/122701 8/2016
WO WO 2016/134371 8/2016
WO WO 2016/135041 9/2016
WO WO 2016/135066 9/2016
WO WO 2016/142768 9/2016
WO WO 2016/146702 9/2016
WO WO 2016/161390 10/2016
WO WO 2016/164369 10/2016
WO WO 2016/164637 10/2016
WO WO-2016/166139 A1 10/2016
WO WO 2016166629 A1 10/2016
WO WO 2016/184592 11/2016
WO WO 2016/187220 11/2016
WO WO 2016/191305 12/2016
WO WO 2016/196237 12/2016
WO WO 2016/201389 12/2016
WO WO 2016/207273 12/2016
WO WO 2016/207278 12/2016
WO WO 2016201300 A1 12/2016
WO WO 2017/005732 1/2017
WO WO 2017/008169 1/2017
WO WO-2017/011342 A1 1/2017
WO WO 2017/021349 2/2017
WO WO 2017/021450 2/2017
WO WO 2017/048824 3/2017
WO WO 2017/075432 5/2017
WO WO 2017/079694 5/2017
WO WO 2017/081190 5/2017
WO WO 2017/083545 5/2017
WO WO 2017/114694 7/2017
WO WO 2017/124002 7/2017
WO WO 2017/125897 7/2017
WO WO 2017/143406 8/2017
WO WO 2017/165464 9/2017
WO WO 2017/165683 9/2017
WO WO 2017/177337 10/2017
WO WO 2017/180813 10/2017
WO WO 2017/211873 12/2017
WO WO 2017/218707 12/2017
WO WO 2018/045090 3/2018
WO WO 2018/083204 5/2018
WO WO 2018/098365 5/2018
WO WO 2018/119171 6/2018
WO WO 2018/148445 8/2018
WO WO 2018/148447 8/2018
WO WO 2018/148566 8/2018
WO WO 2018/148610 8/2018
WO WO-2018/152516 A1 8/2018
WO WO 2018/152518 8/2018
WO WO 2018/152530 8/2018
WO WO 2018/152547 8/2018
WO WO 2018/157147 8/2018
WO WO 2018/201051 11/2018
WO WO 2018/217799 11/2018
WO WO 2018/217945 11/2018
WO WO 2018/217947 11/2018
WO WO 2019/028027 2/2019
WO WO 2019/035939 2/2019
WO WO 2019/040727 2/2019
WO WO 2019/051308 3/2019
WO WO 2019/055677 3/2019
WO WO 2019/157332 8/2019
WO WO 2019/157366 8/2019
WO WO 2019/164929 8/2019
WO WO 2019/164930 8/2019
WO WO 2019/195408 10/2019
WO WO 2019/195409 10/2019

(56) References Cited

FOREIGN PATENT DOCUMENTS

| | | | |
|---|---|---|---|
| WO | WO 2019/217332 | | 11/2019 |
| WO | WO-2019/217332 | A1 | 11/2019 |
| WO | WO 2019/222449 | | 11/2019 |
| WO | WO 2019/231920 | | 12/2019 |
| WO | WO-2020/033587 | A1 | 2/2020 |
| WO | WO 2020/033630 | | 2/2020 |
| WO | WO-2020/033664 | A1 | 2/2020 |
| WO | WO-2020/033702 | A1 | 2/2020 |
| WO | WO 2020/086758 | | 4/2020 |
| WO | WO 2020/172189 | | 8/2020 |
| WO | WO 2021/041878 | | 3/2021 |
| WO | WO-2021/041878 | A1 | 3/2021 |
| WO | WO-2021/076554 | A1 | 4/2021 |
| WO | WO-2021/076564 | A1 | 4/2021 |
| WO | WO-2021/216916 | A1 | 10/2021 |
| WO | WO-2021/226163 | A2 | 11/2021 |
| WO | WO-2021/226193 | A1 | 11/2021 |
| WO | WO-2022/031935 | A1 | 2/2022 |
| WO | WO-2022/031965 | A1 | 2/2022 |
| WO | WO 2022/187539 | | 9/2022 |
| WO | WO-2022/187539 | A1 | 9/2022 |
| WO | WO-2023/056243 | A1 | 4/2023 |
| WO | WO-2023/056252 | A1 | 4/2023 |
| WO | WO-2023/107954 | A1 | 6/2023 |
| WO | WO-2023/107956 | A1 | 6/2023 |
| WO | WO-2023/154796 | A2 | 8/2023 |
| WO | WO-2023/168384 | A2 | 9/2023 |

OTHER PUBLICATIONS

MacCallum et al.,Antibody-antigen interactions: contact analysis and binding site topography, J. Mol. Biol. 262:732-745, 1996.*

Lamminmaki et al., Chrystal structure of a recombinant anti-estradiol Fab fragment in complex with the 17beta-estradiol, J. Blol. Chem. 276:36687-94, 2001.*

Yan et al., Construction of a synthetic phage-displayed Nanobody library with CDR3 regions randomized by trinucleotide cassettes for diagnostic applications, J. Transl. Med. 12:343, 2014.*

Kranz et al., Restricted reassociation of heavy and light chains from hapten-specific monoclonal antibodies, Proc. Natl. Acad. Sci., USA, 78(9):5807-5811, 1981.*

Trivedi et al., Clinical pharmacology and translational aspects of bispecific antibodies, Clin. Transl. Sci. 10:147-162, 2017.*

Herold et al., Determinants of the assembly and function of antibody variable domains Scientific Reports, 7:12276, DOI: 10.1038/ S41598-017-12519-9, Sep. 2017.*

Novus Biologicals, CD16—Find me on macrophages, neutrophils and NK cells, retrieved online: <URL:https://www.novusbio.com/antibody-news/antibodies/cd16-find-me-on-macrophages-neutrophils-and-nk-cells> [retrieved on Aug. 2, 2023], Jan. 5, 2015.*

Khattar et al., B-Cell Maturation Antigen Is Exclusively Expressed in a Wide Range of B-Cell and Plasma Cell Neoplasm and in a Potential Therapeutic Target for BCMA Directed Therapies, Blood:130(Suppl_1):2755, Abst. 622, Dec. 7, 2017.*

Yang et al., Bispecific Antibodies as a Development Platform for New Concepts and Treatment Strategies, Int. J. Molec. Sci. 18:48, 2017.*

International Search Report and Written Opinion dated Aug. 16, 2018 for International Application No. PCT/US18/17653 (9 pages).

International Search Report and Written Opinion dated Feb. 13, 2020 for PCT/US2019/045632.

International Search Report and Written Opinion dated Aug. 16, 2018 for PCT/US2018/017470.

Ahmad et al., 2012, "scFv antibody: principles and clinical application," Clinical and Developmental Immunology 2012: 1-16.

Anderson et al., 2016, Cancer Research, 76(14):CT034-CT034 (abstract only).

Averdam et al., 2009, "A novel system of polymorphic and diverse NK cell receptors in primates", PLoS Genetics, 5(10): e1000688.

Baek et al., 2014, "Construction of a large synthetic human Fab antibody library on yeast cell surface by optimized yeast mating", Journal of Microbiology and Biotechnology, 24(3):408-420.

Busfield et al., 2014, "Targeting of acute myeloid leukemia in vitro and in vivo with an anti-CD123 mAb engineered for optimal ADCC," Leukemia 28(11):2213-2221.

Cho et al., 2010, "Delivery of NKG2D ligand using an anti-HER2 antibody-NKG2D ligand fusion protein results in an enhanced innate and adaptive antitumor response", Cancer Research, 70(24):10121-10130.

Choi et al., 2015, "Engineering of immunoglobin Fc heterodimers using yeast surface-displayed combinatorial Fc library screening", PloS One, vol. 10, article No. 30145349:1-20.

Chu et al., 2014, "Immunotherapy with Long-Lived Anti-CD123×Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," Blood, 124(21) (5 pages).

Ding et al., 2018, "Fusion proteins of NKG2DL in cancer immunotherapy", International J of Molecular Sciences, 19(1):177.

Elliott et al., 2014, "Antiparallel conformation of knob and hole aglycosylated half-antibody homodimers is mediated by a CH2-CH3 hydrophobic interaction", J. Mol. Biol., 426(9):1947-57.

Epling-Burnette et al., 2004, "Dysregulated NK receptor expression in patients with lymphoproliferative disease of granular lymphocytes", Blood, 13(9):3431-3439.

Felices et al., 2016, "Generation of BiKEs and TriKEs to Improve NK Cell-Mediated Targeting of Tumor Cells" Methods Mol. Biol., vol. 1441:333-346.

Gantke et al., 2016, Trispecific antibodies for selective CD16A-directed NK-cell engagement in multiple myeloma, Blood, 128(22):4513-4513.

Germain et al., 2005, Clinical Cancer Research, Amer. Assoc. for Cancer Research, 11(20):7516-7522.

Glas et al., 1997, "Analysis of rearranged immunoglobulin heavy chain variable region genes obtained from a bone marrow transplant (BMT) recipient," Clinical & Experimental Immunology 107 (2):372-380.

Gleason et al., 2012, "Bispecific and Trispecific Killer Cell Engagers Directly Activate Human NK Cells through CD16 Signaling and Induce Cytotoxicity and Cytokine Production," Molecular Cancer Therapeutics 11 (12): 2674-2684.

Gleason et al., 2014, "CD16×CD33 bispecific killer cell engager (BiKE) activates NK cells against primary MDS and MDSC CD33+ targets.", Blood, 123(19):3016-3026.

Ha et al., 2016, "Immunoglobin Fc heterodimer platform technology: from design to applications in therapeutic antibodies and proteins", Frontiers in Immunology, 7(394):1-16.

Hezareh et al., 2001, "Effector Function Activities of a Panel of Mutants of a Broadly Neutralizing Antibody against Human Immunodeficiency Virus Type 1," Journal of Virology 75 (24):12161-12168.

Jachimowicz et al., 2011, "Induction of In Vitro and In Vivo NK Cell Cytotoxicity Using High-Avidity Immunoligands Targeting Prostate-Specific Membrane Antigen in Prostate Carcinoma," Mol Cancer Thera, 10(6): 1036-1045.

Kellner et al., 2015, "Enhancing natural killer cell-mediated lysis of lymphoma cells by combining therapeutic antibodies with CD20-specific immunoligands engaging NKG2D or NKp30," OncoImmunology 5 (1): e1058459.

Kellner et al., 2013, "Promoting natural killer cell functions by recombinant immunoligands mimicking an induced self phenotype", Oncoimmunology, 2(6):e24481.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," Leukemia 26:830-834.

Kwong et al., 2008, "Generation, affinity maturation, and characterization of a human anti-human NKG2D monoclonal antibody with dual antagonistic and agonistic activity," Journal of Molecular Biology 384 (5): 1143-1156.

(56) References Cited

OTHER PUBLICATIONS

Lin et al., 2014, "CD4(+) NKG2D(+) T cells induce NKG2D down-regulation in natural killer cells in CD86-RAE-1ε transgenic mice", Immunology, 141(3):401-415.
Liu et al., 2017, "Fc engineering for Developing Therapeutic Bispecific Antibodies and Novel Scaffolds," Frontiers in Immunology 8, 38: 1-15.
Madlener et al., 2010, "A Bispecific Protein Targeting the NKG2D Receptor on Natural Killer Cells: In Vitro and In Vivo activity of ULBP2-CEA," Blood 116(21):2095.
Maelig et al., 2016, "NK cells and cancer: you can teach innate cells new tricks" Nature Reviews Cancer, 16(1):7-19.
Nagasaki et al., 2014, "Interleukin-6 released by colon cancer-associated fibroblasts is critical for tumour angiogenesis: anti-interleukin-6 receptor antibody suppressed angiogenesis and inhibited tumour-stroma interaction", British Journal of Cancer, 110(2):469-478.
Petricevic et al., 2013, "Trastuzumab mediates antibody-dependent cell-mediated cytotoxicity and phagocytosis to the same extent in both adjuvant and metastatic HER2/neu breast cancer patients," Journal of Translational Medicine 11 (307).
Raab et al., 2014, "Fc-Optimized NKG2D-Fc Constructs Induce NK Cell Antibody-Dependent Cellular Cytotoxicity Against Breast Cancer Cells Independently of HER2/neu Expession Status," Journal of Immunology 193(8): 4261-72.
Romee et al., 2013, "NK cell CD16 surface expression and function is regulated by a disintegrin and metalloprotease-17 (ADAM17)," Blood 121(18): 3599-608.
Rothe et al., 2013, "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.
Ryan et al. 2007, "Antibody targeting of B-cell maturation antigen on malignant plasma cells", Molecular Cancer Therapeutics, 6(11):3009-3018.
Schuster et al. (2015) "Immunotherapy with the trifunctional anti-CD20×anti-CD3 antibody FBTA05 (Lymphomun) in paediatric high-risk patients with recurrent CD20-positive B cell malignancies," British Journal of Haematology 169 (1):90-102.
Smits et al., 2016, "Designing multivalent proteins based on natural killer cell receptors and their ligands as immunotherapy for cancer", Expert Opinion on Biological Therapy, 16(9):1105-1112.
Spear et all., 2013, "NKG2D ligands as therapeutic targets", Cancer Immunology, 13(8): 14 pages.
Steigerwald et al., 2009, "Human lgG1 antibodies antagonizing activating receptor NKG2D on natural killer cells," mAbs 1(2): 115-127.
Steinbacher et al., 2014, "An Fc-optimized NKG2D-immunoglobulin G fusion protein for induction of natural killer cell reactivity against leukemia," International Journal of Cancer 136(5): 1073-1084.
Strong, 2002, "Asymmetric ligand recognition by the activating natural killer cell receptor NKG2D, a symmetric homodimer," Molecular Immunology 38 (14):1029-1037.
Tay et al., 2016, "TriKEs and BiKEs join CARs on the cancer immunotherapy highway", Human Vaccines and Immunotherapeutics, 12(11):2790-2796.
Vaks et al., 2018, "Design Principles for Bispecific lgGs, Opportunities and Pitfalls of Artificial Disulfide Bonds," Antibodies 7(3): 1-28.
Von Strandmann, 2006, "A novel bispecific protein (ULBP2-BB4) targeting the NKG2D receptor on natural killer (NK) cells and CD138 activates NK cells and has potent antitumor activity against human multiple myeloma in vitro and in vivo," Blood 107(5): 1955-1962.
Wang et al., 2016, "A bispecific protein rG7S-MICA recruits natural killer cells and enhances NKG2D-mediated immunosurveillance against hepatocellular carcinoma," Cancer Letters 372:166-178.
Weiss-Steider et al. (2011) "Expression of MICA, MICB and NKG2D in human leukemic myelomonocytic and cervical cancer cells," Journal of Experimental & Clinical Cancer Research 30 (1):37.
Wranik et al., 2012, "LUZ-Y, a novel platform for the mammalian cell production of full-length IgG-bispecific antibodies", J. Biol. Chem., 287:43331-43339.
Yao et al., 2019, "A VEGFR2-MICA bispecific antibody activates tumor-infiltrating lymphocytes and exhibits potent anti-tumor efficacy in mice," Cancer Immunology Immunotherapy, Springer, Berlin/Heidelberg 68 (9):1429-1441.
Yeap et al., 2016, "CD16 is indispensable for antibodydependent cellular cytotoxicity by human monocytes," Scientific Reports 6:34310.
Young et al., 1995, "Thermal stabilization of a single-chain Fv antibody fragment by introduction of a disulphide bond," FEBS Letters 377 (2): 135-139.
Carpenter et al., "B-cell maturation antigen is a promising target for adoptive T-cell therapy of multiple myeloma." Clinical cancer research 19.8 (2013): 2048-2060.
Chen et al., 2017, "Targeting FLT3 by chimeric antigen receptor T cells for the treatment of acute myeloid leukemia", Leukemia, 31(8): 1830-1834.
Colman et al., "Effects of amino acid sequence changes on antibody-antigen interactions." Research in Immunology 145.1 (1994): 33-36.
Gauthier et al. (2019) "Multifunctional Natural Killer Cell Engagers Targeting NKp46 Trigger Protective Tumor Immunity," Cell 177(7):1701-1713.
Gooden et al. (2012) "Infiltrating CTLs are bothered by HLA-E on tumors," OncoImmunology, 1(1):92-93.
Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.
Maeda et al., "Engineering of functional chimeric protein G-VargulaLuciferase." Analytical biochemistry 249.2 (1997): 147-152.
McWilliams et al. (2015) "Targeting the Tumor Evasion Interaction of NKG2A and Its Ligand HLA-E Increases Natural-Killer Cell Activity in Chronic Lymphocytic Leukemia," Blood 126 (23):1289.
Myers et al. (2021) "Exploring the NK cell platform for cancer immunotherapy," Nature Reviews Clinical Oncology 18(2):85-100.
Nie et al. (2020) "Biology drives the discovery of bispecific antibodies as innovative therapeutics," Antibody Therapeutics 3(1):18-62.
Pakula et al., "Genetic analysis of protein stability and function." Annual review of genetics 23.1 (1989): 289-310.
Safdari et al., "Antibody humanization methods—a review and update." Biotechnology and Genetic Engineering Reviews 29.2 (2013): 175-186.
Shen et al., "Single variable domain-IgG fusion: a novel recombinant approach to Fc domain-containing bispecific antibodies." Journal of Biological Chemistry 281.16 (2006): 10706-10714.
Teplyakov et al., "Antibody modeling assessment II. Structures and models." Proteins: Structure, Function, and Bioinformatics 82.8 (2014): 1563-1582.
Torres et al., "The immunoglobulin constant region contributes to affinity and specificity." Trends in immunology 29.2 (2008): 91-97.
Vyas et al. (2016) "Mono- and dual-targeting triplebodies activate natural killer cells and have anti-tumor activity in vitro and in vivo against chronic lymphocytic leukemia,"Oncoimmunology 5(9): p. e1211220.
Written Opinion for International Application No. PCT/US2019/017330 dated Jun. 11, 2019.
Xu et al. (2019) "A VEGFR2-MICA bispecific antibody activates tumor-infiltrating lymphocytes and exhibits potent anti-tumor efficacy in mice, Cancer Immunology Immunotherapy," 68(9): 1429-1441.
Bendayan et al., 1995, "Possibilities of False Immunocytochemical Results Generated by The Use of Monoclonal Antibodies: The Example of the Anti-proinsulin Antibody," J. Histochem. Cytochem. 43:881-886.

(56) References Cited

OTHER PUBLICATIONS

Bostrom, et al., 2009, "Improving Antibody Binding Affinity and Specificity for Therapeutic Development," Methods and Protocols 525:353-376.
Brinkmann et al. (2017) "The making of bispecific antibodies," MABS 9(2)182-212.
Bryceson et al. (2006) "Synergy among receptors on resting NK cells for the activation of natural cytotoxicity and cytokine secretion," Blood 107(1):159-166.
Cai et al., 2014, "Autonomous stimulation of cancer cell plasticity by the human NKG2D lymphocyte receptor coexpressed with its ligands on cancer cells", PLOS One, 9(10):e108942.
Casset et al. (2003) "A peptide mimetic of an anti-CD4 monoclonal antibody by rational design," Biochemical and Biophysical Research Communications 307:198-205.
Chen X. et al. (2013) "Fusion protein linkers: property, design and functionality" Advanced drug delivery reviews, 65(10):1357-1369.
Davis et al. (1999) "Therapy of B-Cell Lymphoma with Anti-CD20 Antibodies Can Result in the Loss of CD20 Antigen Expression," Clinical Cancer Research 5:611-615.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084.
Dickopf et al. (2020) "Format and geometries matter: Structure-based design defines the functionality of bispecific antibodies," Computational and Structural Biotechnology Journal 18:1221-1227.
Edwards et al. (2003) "The Remarkable Flexibility of the Human Antibody Repertoire; Isolation of Over One Thousand Different Antibodies to a Single Protein, BLyS," J. Mol. Biol. 334:103-118.
Extended European Search Report dated Mar. 18, 2021 for EP App. No. 18840650.8.
Gonzales, et al. (2005) "Minimizing the Immunogenicity of Antibodies for Clinical Application," Tumour Biol. 26(1):31-43.
Henry et al. (2017) "Stability-Diversity Tradeoffs Impose Fundamental Constraints on Selection of Synthetic Human VH/VL Single-Domain Antibodies from In Vitro Display Libraries," Frontiers in Immunology, 8:1-15.
Hoseini et al. (2017) "Acute myeloid leukemia targets for bispecific antibodies," Blood Cancer Journal 7(2):e522-e522.
Junttila et al. (2014) "Antitumor Efficacy of a Bispecific Antibody That Targets HER2 and Activates T Cells," Cancer Research 74(19):5561-5571.
Kennedy et al. (2002) "Incidence and nature of CD20-negative relapses following rituximab therapy in aggressive B-cell non-Hodgkin's lymphoma: a retrospective review," British Journal of Haematology 119:412-416.
Kijanka et al. (2013) "Rapid optical imaging of human breast tumour xenografts using anti-HER2 VHHs site-directly conjugated to IRDye 800CW for image-guided surgery," Eur J Nucl Med Mol Imaging 40:1718-1729.
Kim et al. (2014) "Mutational approaches to improve the biophysical properties of human singledomain antibodies," Biochimica et Biophysica Acta, 1844:1983-2001.
Koerner et al. (2015) "Induction of NK and T Cell Immune Responses Against Leukemia Cells By Bispecific NKG2D-CD16 and -CD3 Fusion Proteins," Blood 126(23):2558, Abstract 606.
Krieg et al. (2005) "Functional Analysis of B and T Lymphocyte Attenuator Engagement on CD4+ and CD8+ T Cells," The Journal of Immunology 175(10):6420-6427.
Lin et al. (2011) "Improved affinity of a chicken single-chain antibody to avian infectious bronchitis virus by site-directed mutagenesis of complementarity-determining region H3," African Journal of Biotechnology 10(79):18294-18302.
Lloyd et al. (2009) "Modelling the human immune response: performance of a 1011 human antibody repertoire against a broad panel of therapeutically relevant antigens," Protein Engineering, Design and Selection 22(3):159-168.
Lund et al. (1996) "Multiple interactions of IgG with its core oligosaccharide can modulate recognition by complement and human Fc gamma receptor I and influence the synthesis of its oligosaccharide chains," J. Immunol 157:4963-4969.
MacCallum et al. (1996) "Antibody-antigen Interactions: Contact Analysis and Binding Site Topography," J. Mol. Biol. 262:732-745.
Maeda et al. (2015) "New antibody modification technology and its application to antibody drugs," Farumashia 51(5):424-428.
Mariuzza et al. (1987) "The Structural Basis of Antigen-Antibody Recognition," Ann. Rev. Biophys. Chem. 16:139:59.
Martindale et al., 1998, "Length of huntingtin and its polyglutamine tract influences localization and frequency of intracellular aggregates," Nature Genetics 18: 150-154.
McCarthy et al. (2001) "Altering the fine specificity of an anti-Legionella single chain antibody by a single amino acid insertion," Journal of Immunological Methods 251:137-149.
Michaelson et al., 2009, "Anti-tumor activity of stability= engineered IgG-like bispecific antibodies targeting TRAIL-R2 and LTβR," mAbs 1(2): 128-141.
Morris (1996) "Epitope Mapping of Protein Antigens by Competition ELISA," The Protein Protocols Handbook, Totowa, NJ, Humana Press, 595-600.
Nonaka et al., 2009, "Truncation and pathogenic mutations facilitate the formation of intracellular aggregates of TDP-43," Human Molecular Genetics 18(18): 3353-3364.
Notice of Opposition for Colombia Patent Application No. NC2020/0010345 dated Dec. 16, 2020.
Padlan et al. (1989) "Structure of an antibody-antigen complex: Crystal structure of the HyHEL-10 Fab-lysozyme complex," Pro. Natl. Acad. Sci. USA 86:5938-5942.
Paul et al. (1993) "Fundamental Immunology," (textbook) 292-295.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," Cancer Research 4 pages.
Roda-Navarro et al. (2020) "Understanding the Spatial Topology of Artificial Immunological Synapses Assembled in T Cell-Redirecting Strategies: A Major Issue in Cancer Immunotherapy," Frontiers in Cell and Developmental Biology 7:1-5.
Rudikoff et al. (1982) "Single amino acid substitution altering antigen-binding specificity," Pro. Natl. Acad. Sci USA 79:1979-1983.
Schroeder et al. (2010) "Structure and Function of Immunoglobulins," J Allergy Clin Immunol 125:S41-S52.
Shum et al. (2002) "Conservation and Variation in Human and Common Chimpanzee CD94 and NKG2 Genes," The Journal of Immunology 168:240-252.
Stamova et al. (2011) "Simultaneous engagement of the activatory receptors NKG2D and CD3 for retargeting of effector cells to CD33-positive malignant cells," Leukemia 25:1053-1056.
Stein et al. (2012) "Natural Killer (NK)- and T-Cell Engaging Antibody-Derived Therapeutics," Antibodies 1:88-123.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," Clin Cancer Res, 22(14):3440-50.
Wang et al. (2018) "IgG Fc engineering to modulate antibody effector functions," Protein Cell 9(1):63-73.
Wu et al. (1999) "Humanization of a Murine Monoclonal Antibody by Simultaneous Optimization of Framework and CDR Residues," J. Mol. Biol. 294:151-162.
Xu et al. (2014) "Production of bispecific antibodies in "knobs-into-holes" using a cell-free expression system," mAbs 7(1)231-242.
Bost et al., 1988, "Antibodies Against a Peptide Sequence Within the HIV Envelope Protein Crossreacts with Human Interleukin-2," Immunological Investigations, 17(6&7): 577-586.
Branca et al., 2018, "Nature Biotechnology's Academic Spinouts of 2017," Nature Biotechnology 36(4): 297-306.

(56) References Cited

OTHER PUBLICATIONS

Brown, et al., 1996, "Tolerance of single, but not multiple, amino acid replacements in antibody VH CDR 2: a means of minimizing B cell wastage from somatic hypermutation?," Journal of Immunology, 156: 3285-3291.
Choi et al. (2013) "A Heterodimeric Fc-Based Bispecific Antibody Simultaneously Targeting VEGFR-2 and Met Exhibits Potent Antitumor Activity," Mol Cancer Ther, 12(12):2748-2759.
Henry et al. (2004) "A Prostate-Specific Membrane Antigen-Targeted Monoclonal Antibody-Chemotherapeutic Conjugate Designed for the Treatment of Prostate Cancer," Cancer Research 64:7995-8001.
Piche-Nicholas et al., 2018, "Changes in complementarity-determining regions significantly alter IgG binding to the neonatal Fc receptor (FcRn) and pharmacokinetics," mAbs 10(1): 81-94.
Portolano et al., 1993, "Lack of promiscuity in autoantigen-specific H and L chain combinations as revealed by human H and L chain 'roulette'," J. Immunol. 15(30):880-887.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Wensveen et al., 2018, "NKG2D: A master regulator of immune cell responsiveness," Frontiers in Immunology 9:441.
Written Opinion for International Application No. PCT/US2019/018751 dated Jul. 1, 2019.
Affimed, Affimed Enters Into Collaboration With Merck To Evaluate AFM13 in Combination With . . . Retreived <URL:https ://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Akbar et al., 2021, "A compact vocabulary of paratope-epitope interactions enables predictability of antibody-antigen binding," *Cell Reports*, 34:108856 21 pages.
Altshuler et al., 2010, "Generation of Recombinant Antibodies and Means for Increasing Their Affinity," *Biochemistry* (Moscow), 75(13):1584-1605.
Atwell et al., 1997, "Stable heterodimers from remodeling the domain interface of a homodimer using a phage display library", J. Mol. Biol., 270(1):26-35.
Berenbaum, 1977, "Synergy, additivism and antagonism in immunosuppression," Clin. Exp. Immunol., 28:1-18.
Berenbaum, 1989, "What is Synergy?" Pharmacological Reviews, 41:93-141.
Boltz, 2011, "Bi-specific Aptamers mediating Tumour Cell Lysis," Dissertation, M.Sc. Molekulare Biotechnologie, Technische Universität Darmstadt, pp. 1-133.
Bowen et al., 2016, "Revisiting the Immunoglobulin Intramolecular Signaling Hypothesis," *Trends Immunol.*, 37(11):721-723.
Bruhns et al., 2009, "Specificity and affinity of human FCg receptors and their polymorphic variants for human IgG subclasses," *Blood* , 113(16):3716-3724.
Chan et al., 2010, "Therapeutic antibodies for autoimmunity and inflammation," Nature Reviews 10:301-316.
Choi et al., 2015, "Crystal structures of immunoglobulin Fc heterodimers reveal the molecular basis for heterodimer formation," Molecular Immunology 65(2):377-83.
Cunningham et al., 1969, "Subgroups of Amino Acid Sequences in the Variable Regions of Immunoglobulin Heavy Chains," Proc Natl Acad Sci USA 64(3):997-1003.
Dahlberg et al., 2015, "Natural Killer Cell-Based Therapies Targeting Cancer: Possible Strategies to Gain and sustain Anti-Tumor Activity" Frontiers In Immunology 6(Article 605):19 pages.
Davis et al., 2010, "SEEDbodies: Fusion Proteins Based on Strand-Exchange Engineered Domain (Seed) CH3 Heterodimers in an Fe Analogue Platform for Asymmetric Binders or Immunofusions and Bispecific Antibodies," Protein Eng Des Sel 23(4):195-202.
Doppalapudi et al., 2010, "Chemical generation of bispecific antibodies," PNAS, 107(52):22611-22616.
El-Amine et al., 2002, "In vivo induction of tolerance by an Ig peptide is not affected by the deletion of FcR or a mutated IgG Fc fragment," *International Immunology* , 14(7):761-766.
Feng et al., 2011, "Design, Expression and Characterization of a Soluble Single-Chain Functional Human Neonatal Fe Receptor," Protein Expr Purif 79(1):66-71.
Germain et al., 2008, "Redirecting NK cells mediated tumor cell lysis by a new recombinant bifunctional protein," *Protein Engineering, Design & Selection* , 21(11):665-672.
Goel et al., 2004, "Plasticity Within the Antigen-Combining Site May Manifest as Molecular Mimicry in the Humoral Immune Response," Journal of Immunology, 173:7358-7367.
Gunasekaran et al., 2010, "Enhancing Antibody Fe Heterodimer Formation through Electrostatic Steering Effects: Applications to Bispecific Molecules and Monovalent lgG," J Biol Chem 285(25):19637-46.
Hasegawa et al., 2017, "Single amino acid substitution in LC-CDR1 induces Russell body phenotype that attenuates cellular protein synthesis through elF2a phosphorylation and thereby downregulates IgG secretion despite operational secretory pathway traffic," *MABS* , 9(5):854-873.
Hlavacek et al., 1999, "Steric Effects on Multivalent Ligand-Receptor Binding: Exclusion of Ligand Sites by Bound Cell Surface Receptors," Biophysical Journal, 76(6): 3031-3043.
Holliger et al., 2005, "Engineered antibody fragments and the rise of single domains," Nat Biotechnol 23(9): 1126-36.
Janeway et al., 1997, "Immunology Third Edition," Garland Publishing, Inc. Ch. 3, Structure of the Antibody Molecule and Immunoglobulin Genes, 3:1-11.
Jonnalagadda et al., 2015, "Chimeric Antigen Receptors With Mutated IgG4 Fc Spacer Avoid Fc Receptor Binding and Improve T Cell Persistence and Antitumor Efficacy," *Molecular Therapy*, 23(4):757-768.
Kanyavuz et al., 2019, "Breaking the Law: Unconventional Strategies for Antibody Diversification, " Nature Review, 19:355-368.
Kaur et al., 2015, "Applications of In Vitro—In Vivo Correlations in Generic Drug Development: Case Studies," *The AAPS Journal* , 17(4):1035-1039; doi: 10.1208/s12248-015-9765-1.
Kjellev et al., 2007, "Inhibition of NKG2D receptor function by antibody therapy attenuates transfer-induced colitis in SCID mice," *Eur. J. Immunol.* , 37:1397-1406.
Klein et al., 2012, "Progress in overcoming the chain association issue in bispecific; heterodimeric lgG antibodies," MaBs 4(6):653-663.
Kunik et al., 2012, "Structural consensus among antibodies defines the antigen binding site," PLoS Comput Biol., 8(2):e1002388. Epub Feb. 23, 2012.
Lewis et al., 2014, "Generation of bispecific IgG antibodies by structure-based design of an orthogonal Fab interface", Nat. Biotechnol., 32(2):198-198.
Lippow et al., 2007, "Computational design of antibody-affinity improvement beyond in vivo maturation," *Nature Biotechnology* , 25(10):1171-1176.
Lo et al., 2021 "Conformational epitope matching and prediction based on protein surface spiral features," *BMC Genomics* , 22(Suppl 2): 116 16 pages.
Mandelboim et al., 1999, "Human CD16 as a lysis receptor mediating direct natural killer cell cytotoxicity," *PNAS USA* , 96(10):5640-5644; doi: 10.1073/pnas.96.10.5640.
Marks et al., 2020, "How repertoire data are changing antibody science," *J. Biol. Chem.*, 295(29):9823-9837.
Merchant et al., 1998, "An efficient route to human bispecific lgG," Nature Biotechnology 16, 677-681 doi : 10.1038/nbt0798-677.
Miller et al., 2003, "Design, Construction, and in Vitro Analyses of Multivalent Antibodies," J Immunol 170(9):4854-61.
Mimoto et al., 2014, "Crystal structure of a novel asymmetrically engineered Fc variant with improved affinity for FcγRs", Mol. Immunol., 58(1):132-138.
Moore et al., 2011, "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.

(56) References Cited

OTHER PUBLICATIONS

Muda et al., 2011, "Therapeutic assessment of SEED: a new engineered antibody platform designed to generate mono- and bispecific antibodies", Protein Eng. Des. Sel., 24(5):447-454.
Muller et al., 2015, "Trastuzumab emtansine (T-DM1) renders HER2+ breast cancer highly susceptible to CTLA-4/PD-1 blockade," Sci. Transl. Med., 7(315):1-14.
Muntasell et al., 2017, "Targeting NK-cell checkpoints for cancer immunotherapy," Current Opinion in Immunology 45:73-81.
Parsons et al., 2016, "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.
Rabia et al., 2018, "Understanding and overcoming trade-offs between antibody affinity, specificity, stability and solubility" Biochem Eng J., 137:365-374.
Raulet, 2003, "Roles of the NKG2D immunoreceptor and its ligands," *Nature: Reviews Immunology*, 3:781-790; doi: 10.1038/nri1199.
Ridgway et al., 1996, "Knobs-into-Holes' engineering of antibody Ch3 domains for heavy chain heterodimerization," Protein Engineering 9(7):617-21.
Roell et al., 2017, "An Introduction to Terminology and Methoodology of Chemical Synergy—Perspectives from Across Disciplines," *Frontiers in Pharmacology: Cancer Molecular Targets and Therapeutics*, 8:1-11.
Rosano et al., 2014, "Recombinant protein expression in *Escherichia coli*: advances and challenges" Frontiers in Microbiology, 5(172):17 pages.
Roskopf, et al., 2016, "Dual-targeting triplebody 33-3-19 mediates selective lyssi of biphenotypic CD19+ CD33+ leukemia cells," Oncotarget, 7(6): 22579-22589.
Sazinsky et al., 2008, "Aglycosylated immunoglobulin $G_1$ variants productively engage activating Fc receptors," *Proceedings of the National Academy of Sciences* , 105(51)20167-20172.
Schmitz et al., 2001, "Pharmacogenomics: implications for laboratory medicine," Clinica Chimica Acta 308:43-53.
Singer et al., 1998, "Genes and Genomes," Moscow, "Mir" 1:63-64.
Sondermann et al., 2000, "The 3.2-Å crystal structure of the human IgG1 Fc fragment-FcγRIII complex," Nature, 406(6793):267-273.
Strop et al., 2012, "Generating Bispecific Human lgG1 and lgG2 Antibodies from Any Antibody Pair," J Mol Biol 420:204-19.
Sulea et al., 2018, "Application of Assisted Design of Antibody and Protein Therapeutics (ADAPT) improves efficacy of a *Clostridium difficile* toxin A single-domain antibody," 8:2260, 11 pages.
Tallarida, 2000, "Drug Synergism and Dose Effect Analysis," Ed. Chapman & Hall pp. 1-71.
Thakur et al., 2018, "Bispecific antibody based therapeutics: Strengths and challenges," Blood Review, 32:339-347.
Vajda et al., 2021, "Progress toward improved understanding of antibody maturation," *Current Opinion in Structural Biology* , 67:226-231.
Vidarsson et al., 2014, "IgG subclasses and allotypes: from structure to effector functions," Front. Immunol. 5:520.
Von Kreudenstein et al., 2013, "Improving Biophysical Properties of a Bispecific Antibody Scaffold to Aid Developability: Quality by Molecular Design," mAbs 5(5):646-54.
Von Kreudenstein et al., 2014, "Protein Engineering and the Use of Molecular Modeling and Simulation: The Case of Heterodimeric Fe Engineering," Methods 65(1):77-94.
Ward et al., 1989, "Binding activities of a epertoire of single immunoglobulin variable domains secreted from *Escherichia coli," Nature* , 341:544-546.
Wark et al., 2006, "Latest technologies for the enhancement of antibody affinity", *Advanced Drug Delivery Reviews*, 58(5-6):657-670.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Written Opinion for International Application No. PCT/US2018/017470 dated Apr. 24, 2018.
U.S. Appl. No. 16/483,330, filed Aug. 2, 2019.
U.S. Appl. No. 16/483,572, filed Aug. 5, 2019.
U.S. Appl. No. 16/967,216, filed Aug. 4, 2020.
U.S. Appl. No. 16/967,218, filed Aug. 4, 2020.
U.S. Appl. No. 17/058,335, filed Nov. 24, 2020.
U.S. Appl. No. 17/266,349, filed Feb. 5, 2021.
U.S. Appl. No. 17/543,628, filed Dec. 6, 2021.
U.S. Appl. No. 17/686,238, filed Mar. 3, 2022.
U.S. Appl. No. 18/149,965, filed Jan. 4, 2023.
U.S. Appl. No. 18/150,040, filed Jan. 4, 2023.
U.S. Appl. No. 18/501,413, filed Nov. 3, 2023.
U.S. Appl. No. 18/501,419, filed Nov. 3, 2023.
U.S. Appl. No. 18/501,427, filed Nov. 3, 2023.
Bartlett et al., 2007, "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S).
Bogen et al., 2021, "Design of a Trispecific Checkpoint Inhibitor and Natural Killer Cell Engager Based on a 2+1 Common Light Chain Antibody Architecture," Frontiers in Immunology 12:16 pages.
Briney et al., 2019, "Commonality despite exceptional diversity in the baseline human antibody repertoire," Nature 566:393 (19 pages).
Dasgupta et al., 2005, "Inhibition of NK Cell Activity through TGF-b1 by Down-Regulation of NKG2D in a Murine Model of Head and Neck Cancer," J Immunol 175(8):5541-5550.
Demaria et al., 2021, "Natural killer cell engagers in cancer immunotherapy: Next generation of immuno-oncology treatments," Eur. J. Immunol. 51:1934-1942.
Farumashia, 2015,v Journal of the Pharmaceutical Society of Japan, 51(5), pp. 424-428 Novel antibody modification technology and its application to antibody drugs.
Feng et al., 2020, "NKG2D-Fc fusion protein promotes antitumor immunity through the depletion of immunosuppressive cells," Cancer Immunol. Immunother. 69(10):2147-2155.
Gao et al., 2020, "Novel immunomodulatory drugs and neo-substrates," Biomarker Research, 8(2).
Giuliani et al., 2017, "Activation of NK cells and disruption of PD-L1/PD-1 axis: two different ways for lenalidomide to block myeloma progression," Oncotarget 8(14):24031-24044.
Hansen et al., 2020, "Discovery of CRBN E3 Ligase Modulator CC-92480 for the Treatment of Relapsed and Refractory Multiple Myeloma," Journal of Medicinal Chemistry, 63(13): 6648-6676.
International Search Report and Written Opinion dated Dec. 22, 2021 for Int'l App. No. PCT/EP2021/075012.
Katano et al., 2015, "Predominant Development of Mature and Functional Human NK Cells in a Novel Human IL-2-Producing Transgenic NOG Mouse" J. Immunol. 194(7):3513-3525.
Khan et al., 2014, "Adjustable Locks and Flexible Keys: Plasticity of Epitope-Paratope Interactions in Germline Antibodies," J. Immunol 192:5398-5405.
Miller et al,. 2019, "Natural Killer Cells in Cancer Immunotherapy," Ann. Rev. Cancer Biol. 3:77-103.
Poosaria et al., 2017, "Computational de novo Design of Antibodies binding to a Peptide with High Affinity," 114(6):1331-1342.
Spiess et al., 2015, "Alternative molecular formats and therapeutic applications for bispecific antibodies," Molecular Immunology 67:95-106.
Watanabe et al., 2014, NKG2D functions as an activating receptor on natural killer cells in the common marmoset (*Callithrix jacchus*), Int. Immunol., 26(11): 597-606.
Whalen et al., 2023, "Engaging natural killer cells for cancer therapy via NKG2D, CD16A and other receptors," 15(1) 15 pages.
Wu et al., 2011, "Lenalidomide enhances antibody-dependent cellular cytotoxicity of solid tumor cells in vitro: influence of host immune and tumor markers," Cancer Immunology, Immunotherapy, Springer, 60(1): 61-73.
Xie et al., 2015, "VEGFR2 targeted antibody fused with MICA stimultes NKG2D mediated immunosurveillance and exhibits potent anti-tumor activity against breast cancer," Oncotarget 7(13):16455-16471.

(56) References Cited

OTHER PUBLICATIONS

Yang et al., 2016, "Bispecific Antibodies as a Development Platform for New Concepts and Treatment Strategies" Int. J. Mol. Sci. 18(48) 21 pages.
U.S. Appl. No. 18/482,629, filed Oct. 6, 2023.
U.S. Appl. No. 16/486,921, filed Aug. 19, 2019.
U.S. Appl. No. 16/486,569, filed Aug. 16, 2019, U.S. Pat. No. 11,884,732, Jan. 30, 2024.
U.S. Appl. No. 18/541,475, filed Dec. 15, 2023.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,261, filed Nov. 20, 2019.
U.S. Appl. No. 16/635,079 filed, Jan. 29, 2020.
U.S. Appl. No. 16/639,150, filed Feb. 14, 2020.
U.S. Appl. No. 18/108,961, filed Feb. 13, 2023.
U.S. Appl. No. 16/645,613, filed Mar. 9, 2020.
U.S. Appl. No. 17/045,015, filed Oct. 2, 2020.
U.S. Appl. No. 17/055,792, filed Nov. 16, 2020.
U.S. Appl. No. 17/265,876, filed Feb. 4, 2021.
U.S. Appl. No. 17/265,879, filed Feb. 4, 2021.
U.S. Appl. No. 17/266,966, filed Feb. 8, 2021.
U.S. Appl. No. 17/929,282, filed Sep. 1, 2022.
U.S. Appl. No. 17/287,849, filed Apr. 22, 2021.
U.S. Appl. No. 16/971,104, filed Aug. 19, 2020.
U.S. Appl. No. 17/682,367, filed Feb. 28, 2022.
U.S. Appl. No. 17/769,160, filed Apr. 14, 2022.
U.S. Appl. No. 18/003,308, filed Dec. 23, 2022.
U.S. Appl. No. 17/920,174 filed, Oct. 20, 2022.
U.S. Appl. No. 17/308,691, filed May 5, 2021.
U.S. Appl. No. 18/166,769, filed Feb. 9, 2023.
U.S. Appl. No. 18/177,847, filed Mar. 3, 2023.
U.S. Appl. No. 18/366,876, filed Aug. 8, 2023.
Chen et al. (1999) "Selection and Analysis of an Optimized Anti-VEGF Antibody: Crystal Structure of an Affinity-matured Fab in Complex with Antigen," J. Mol. Biol. 293:865-881.
Hilpert et al. (2012) "Comprehensive analysis of NKG2D ligand expression and release in leukemia: implications for NKG2D-mediated NK cell responses," J Immunol. 189(3):1360-71.
Jorge Flavio Mendoza Rincón (2014) "El receptor NKG2D en la frontera de la inmunovigilancia y la carcinogénesis," Publicación Científica en Ciencias Biomédicas 2(21):237-43.
Kim et al. (1995) "Evidence That the Hinge Region Plays a Role in Maintaining Serum Levels of the Murine IgG1 Molecule," Molecular Immunology 32(7):467-475.
Long et al. (2013) "Controlling NK Cell Responses: Integration of Signals for Activation and Inhibition," Annu Rev Immunol. 2013 ; 31: 10.1146/annurev-immunol-020711-075005.
Van de Winkel et al. (1993) "Human IgG Fc receptor heterogeneity: molecular aspects and clinical implications," Immunology Today 14(5):215-221.
Watzl et al. (2010) "Signal Transduction During Activation and Inhibition of Natural Killer Cells", Curr Protoc Immunol., 90(1):11.9B1-11.9B.17.
Xie et al. (2005) "A new format of bispecific antibody: highly efficient heterodimerization, expression and tumor cell lysis," J Immunol Methods 296(1):95-101.
Yang et al. (2017) "Enhancing NK cell-mediated cytotoxicity to cisplatin-resistant lung cancer cells via MEK/Erk signaling inhibition," Nature Scientific Reports, 7:7958 (13 pages).
Zhang et al. (2021) "Bispecific antibody-mediated redirection of NKG2D-CAR natural killer cells facilitates dual targeting and enhances antitumor activity," *Journal for Immuno Therapy of Cancer*; 9:e002980 (24 pages). doi:10.1136/jitc-2021-002980.
Zhou et al. (1995) "Characterization of human homologue of 4-1BB and its ligand," Immunology Letters 45:67-73.
Absolute Antibody, 2023, Anti-NKG2D [ADI-27749 (A49)] Standard Size Ab03079-3.0, 1 page. Retreived online:<URL:https://absoluteantibody.com/product/anti-nkg2d-adi-27749-a48/Ab03079-3.0_mouse_igg2b/standard>, 2023.
Anderson et al. (2012) "CD137 Is Expressed in Follicular Dendritic Cell Tumors and in Classical Hodgkin and T-Cell Lymphomas," Am. J Pathol. 181(3):795-803.
Billadeau et al. (2003) "NKG2D-DAP10 triggers human NK cell-mediated killing via a Syk-independent regulatory pathway," Nat. Immunol. 4(6):557-64.
Bryceson et al. (2006) "Activation, coactivation, and costimulation of resting human natural killer cells Immunological Reviews," 214:73-91.
Campbell et al. (2004) "NKp44 Triggers NK Cell Activation through DAP12 Association That Is Not Influenced by a Putative Cytoplasmic Inhibitory Sequence," Journal of Immunol. 172(2):899-906.
Davis et al. (2017) "Natural killer cells unleashed: Checkpoint receptor blockade and BIKE/TriKE utilization in NK-mediated anti-tumor immunotherapy," Seminars in Immunology 31:64-75.
Eruslanov et al. (2013) "Expansion of CCR8+ Inflammatory Myeloid Cells in Cancer Patients with Urothelial and Renal Carcinomas," Clinical Cancer Research 19(7):1670-1680.
Fasbender et al. (2017) "Differential requirements for src-Family Kinases in SYK or ZAP70-Mediated SLP-76 Phosphorylation in lymphocytes," Front. Immunol. 8:789.
Kontermann et al. (2015) "Bispecific antibodies," Drug Discovery Today 20(7):838-847 (12 pages).
Liu et al. (2020) "Fc-Engineering for Modulated Effector Functions-Improving Antibodies for Cancer Treatment," Antibodies 9(64):34 pages.
Love et al. (2010) "ITAM-mediated Signaling by the T-Cell Antigen Receptor," Cold Spring Harb Perspect Biol. 2(6):a00248.
Morvan et al. (2016)."NK cells and cancer: you can teach innate cells new tricks" Nat Rev Cancer 16(1):7-19.
Nersesian et al (2020) "N K cell infiltration is associated with improved overall survival in solid cancers: A systematic review and meta-analysis," Translational Oncology 14 (20 pages).
Plitas et al. (2016) "Regulatory T Cells Exhibit Distinct Features in Human Breast Cancer," Immunity 45(5):1122-1134.
Raynaud et al. (2021) "Anti-NKG2D single domain-based antibodies for the modulation of anti-tumor immune response," Oncoimmunology 10(1):e1854529-1-e1854529-14.
Stallard (2016) "New Approach Could Boost Immunotherapy for Breast Cancer," Memorial Sloan Kettering Cancer Center 1-5.
Weatherill et al. (2012) "Towards a universal disulphide stabilised single chain Fv format: importance of interchain disulphide bond location and vL-vH orientation," Protein Engineering, Design, and Selection, 25(7):321-329.
Hale (2024) "Living in LALA land? Forty years of attenuating Fc effector functions," Immunol. Rev. 328(1):422-37.
Ho et al. (2002) "Costimulation of multiple NK cell activation receptors by NKG2D," Journal of Immunology 169(7):3667-3675.
Middelburg et al. (2021) "Overcoming Challenges for CD3-Bispecific Antibody Therapy in Solid Tumors," Cancers 13(2):287 (25 pages).
Muyldermans (2013) "Nanobodies: Natural Single-Domain Antibodies," Annual Review of Biochemistry 82(1):775-797.

* cited by examiner

MULTI-SPECIFIC BINDING PROTEINS BINDING BCMA, NKG2D AND CD16 AND METHODS OF USE

CROSS-REFERENCE TO RELATED APPLICATIONS

This application is a 371 national stage application of international application Serial No. PCT/US2018/017653 filed Feb. 9, 2018, which claims the benefit of and priority to U.S. Provisional Patent Application No. 62/457,780, filed Feb. 10, 2017, the entire contents of which are incorporated by reference herein for all purposes.

SEQUENCE LISTING

The instant application contains a Sequence Listing which has been submitted electronically in ASCII format and is hereby incorporated by reference in its entirety. Said ASCII copy, created on Feb. 8, 2018, is named DFY-003PC_SL.txt and is 91,310 bytes in size.

FIELD OF THE INVENTION

The invention relates to multi-specific binding proteins that bind to B-cell maturation antigen (BCMA), the NKG2D receptor, and CD16.

BACKGROUND

Cancer continues to be a significant health problem despite the substantial research efforts and scientific advances reported in the literature for treating this disease. Blood and bone marrow cancers are frequently diagnosed cancer types, including multiple myelomas, leukemia, and lymphomas. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. Antibodies that bind to certain tumor-associated antigens and to certain immune cells have been described in the literature. See, for example WO 2016/134371 and WO 2015/095412.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-gamma and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g. NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

BCMA is a transmembrane protein belonging to the TNF-receptor superfamily. It specifically binds to the tumor necrosis factor (ligand) superfamily, member 13b (TNFSF13B/TALL-1/BAFF), leading to NF-κB and MAPK8/JNK activation. Its expression is restricted to the B-cell lineage and has been shown to be important for B cell development and autoimmune response. BCMA also binds to various TRAF family members, and thus may transduce signals for cell survival and proliferation. BCMA is implicated in a variety of cancers, such as multiple myeloma, lymphoma and leukemia. The present invention provides certain advantages to improve treatments for BCMA-expressing cancers.

SUMMARY

The invention provides multi-specific binding proteins that bind to BCMA on a cancer cell and the NKG2D receptor and CD16 receptor on natural killer cells. Such proteins can engage more than one kind of NK activating receptor, and may block the binding of natural ligands to NKG2D. In certain embodiments, the proteins can agonize NK cells in humans, and in other species such as rodents and cynomolgus monkeys. Various aspects and embodiments of the invention are described in further detail below.

Accordingly, one aspect of the invention provides a protein that incorporates a first antigen-binding site that binds NKG2D; a second antigen-binding site that binds to BCMA; and an antibody Fc domain, a portion thereof sufficient to bind CD16, or a third antigen-binding site that binds CD16. The antigen-binding sites may each incorporate an antibody heavy chain variable domain and an antibody light chain variable domain (e.g. arranged as in an antibody, or fused together to from an scFv), or one or more of the antigen-binding sites may be a single domain antibody, such as a $V_HH$ antibody like a camelid antibody or a $V_{NAR}$ antibody like those found in cartilaginous fish.

The first antigen-binding site that binds to NKG2D, in one embodiment, can incorporate a heavy chain variable domain related to SEQ ID NO:1, such as by having an amino acid sequence at least 90%, at least 95%, or 100% identical to SEQ ID NO:1, and/or incorporating amino acid sequences identical to the CDR1 (SEQ ID NO:64), CDR2 (SEQ ID NO:65), and CDR3 (SEQ ID NO:66) sequences of SEQ ID NO:1. Alternatively, the first antigen-binding site can incorporate a heavy chain variable domain related to SEQ ID NO:41 and a light chain variable domain related to SEQ ID NO:42. For example, the heavy chain variable domain of the first antigen-binding site can be at least 90%, at least 95%, or 100% identical to SEQ ID NO:41, and/or incorporate amino acid sequences identical to the CDR1 (SEQ ID NO:67), CDR2 (SEQ ID NO:68), and CDR3 (SEQ ID NO:69) sequences of SEQ ID NO:41. Similarly, the light chain variable domain of the second antigen-binding site can be at least 90%, at least 95%, or 100% identical to SEQ ID NO:42, and/or incorporate amino acid sequences identical to the CDR1 (SEQ ID NO:70), CDR2 (SEQ ID NO:71), and CDR3 (SEQ ID NO:72) sequences of SEQ ID NO:42. In other embodiments, the first antigen-binding site can incorporate a heavy chain variable domain related to SEQ ID NO:43 and a light chain variable domain related to SEQ ID NO:44. For example, the heavy chain variable domain of the first antigen-binding site can be at least 90%, at least 95%, or 100% identical to SEQ ID NO:43, and/or incorporate amino acid sequences identical to the CDR1 (SEQ ID NO:73), CDR2 (SEQ ID NO:74), and CDR3 (SEQ ID NO:75) sequences of SEQ ID NO:43. Similarly, the light chain variable domain of the second antigen-binding site can be at least 90%, at least 95%, or 100% identical to SEQ ID NO:44, and/or incorporate amino acid sequences identical to the CDR1 (SEQ ID NO:76), CDR2 (SEQ ID NO:77), and CDR3 (SEQ ID NO:78) sequences of SEQ ID NO:44.

Alternatively, the first antigen-binding site can incorporate a heavy chain variable domain related to SEQ ID NO:45 and a light chain variable domain related to SEQ ID NO:46, such as by having amino acid sequences at least 90%, at least 95%, or 100% identical to SEQ ID NO:45 and SEQ ID NO:46 respectively. In another embodiment, the first antigen-binding site can incorporate a heavy chain variable domain related to SEQ ID NO:47 and a light chain variable domain related to SEQ ID NO:48, such as by having amino acid sequences at least 90%, at least 95%, or 100% identical to SEQ ID NO:47 and SEQ ID NO:48 respectively.

The second antigen-binding site can optionally incorporate a heavy chain variable domain related to SEQ ID NO:49 and a light chain variable domain related to SEQ ID NO:53 or SEQ ID NO:54. For example, the heavy chain variable domain of the second antigen-binding site can be at least 90%, at least 95%, or 100% identical to SEQ ID NO:49, and/or incorporate amino acid sequences identical to the CDR1 (SEQ ID NO:50), CDR2 (SEQ ID NO:51), and CDR3 (SEQ ID NO:52) sequences of SEQ ID NO:49. Similarly, the light chain variable domain of the second antigen-binding site can be at least 90%, at least 95%, or 100% identical to SEQ ID NO:53 and/or incorporate amino acid sequences identical to the CDR1 (SEQ ID NO:55), CDR2 (SEQ ID NO:56), and CDR3 (SEQ ID NO:57) sequences of SEQ ID NO:53. Alternatively, the light chain variable domain of the second antigen-binding site can be at least 90%, at least 95%, or 100% identical to SEQ ID NO:54 and/or incorporate amino acid sequences identical to the CDR1 (SEQ ID NO:55), CDR2 (SEQ ID NO:56), and CDR3 (SEQ ID NO:58) sequences of SEQ ID NO:54.

Alternatively, the second antigen-binding site can incorporate a heavy chain variable domain related to SEQ ID NO:59 and a light chain variable domain related to SEQ ID NO:60. For example, the heavy chain variable domain of the second antigen-binding site can be at least 90%, at least 95%, or 100% identical to SEQ ID NO:59, and/or incorporate amino acid sequences identical to the CDR1 (SEQ ID NO:79), CDR2 (SEQ ID NO:80), and CDR3 (SEQ ID NO:81) sequences of SEQ ID NO:59. Similarly, the light chain variable domain of the second antigen-binding site can be at least 90%, at least 95%, or 100% identical to SEQ ID NO:60, and/or incorporate amino acid sequences identical to the CDR1 (SEQ ID NO:82), CDR2 (SEQ ID NO:83), and CDR3 (SEQ ID NO:84) sequences of SEQ ID NO:60.

In another embodiment, the second antigen-binding site can incorporate a heavy chain variable domain related to SEQ ID NO:61 and a light chain variable domain related to SEQ ID NO:62. For example, the heavy chain variable domain of the second antigen-binding site can be at least 90%, at least 95%, or 100% identical to SEQ ID NO:61, and/or incorporate amino acid sequences identical to the CDR1 (SEQ ID NO:85), CDR2 (SEQ ID NO:86), and CDR3 (SEQ ID NO:87) sequences of SEQ ID NO:61. Similarly, the light chain variable domain of the second antigen-binding site can be at least 90%, at least 95%, or 100% identical to SEQ ID NO:62, and/or incorporate amino acid sequences identical to the CDR1 (SEQ ID NO:88), CDR2 (SEQ ID NO:89), and CDR3 (SEQ ID NO:90) sequences of SEQ ID NO:62.

In some embodiments, the second antigen-binding site incorporates a light chain variable domain having an amino acid sequence identical to the amino acid sequence of the light chain variable domain present in the first antigen-binding site.

In some embodiments, the protein incorporates a portion of an antibody Fc domain sufficient to bind CD16, wherein the antibody Fc domain comprises hinge and CH2 domains, and/or amino acid sequences at least 90% identical to amino acid sequence 234-332 of a human IgG antibody.

Formulations containing one of these proteins; cells containing one or more nucleic acids expressing these proteins, and methods of enhancing tumor cell death using these proteins are also provided.

Another aspect of the invention provides a method of treating cancer in a patient. The method comprises administering to a patient in need thereof a therapeutically effective amount of the multi-specific binding protein described herein. Exemplary cancers for treatment using the multi-specific binding proteins include, for example, multiple myeloma, acute myelomonocytic leukemia, T cell lymphoma, acute monocytic leukemia, and follicular lymphoma.

BRIEF DESCRIPTION OF THE DRAWINGS

FIG. 13A is an exemplary representation of one form of a κλ-Body; FIG. 13B is an exemplary representation of another κλ-Body.

FIG. 34A demonstrates levels of CD107a; FIG. 34B demonstrates levels of IFNγ; FIG. 34C demonstrates levels of CD107a and IFNγ. Graphs indicate the mean (n=2)±SD. Data are representative of five independent experiments using five different healthy donors.

DETAILED DESCRIPTION

Figure 1:
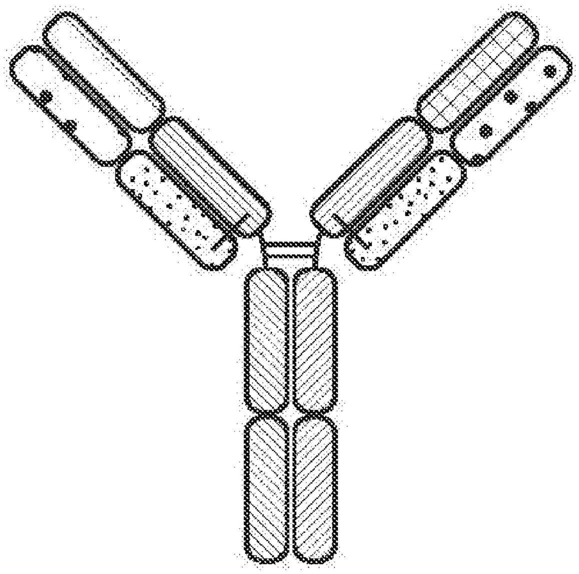
FIG. 1 is a representation of a heterodimeric, multi-specific antibody. NKG2D-binding domain (right arm): tumor antigen-binding domain (left arm). The light chains that are common are represented with the same shade or pattern in the drawing.

The invention provides multi-specific binding proteins that bind BCMA on a cancer cell and the NKG2D receptor and CD16 receptor on natural killer cells to activate the natural killer cell, pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen-binding. In human antibodies, the antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide.

The term "tumor associated antigen" as used herein means any antigen including but not limited to a protein, glycoprotein, ganglioside, carbohydrate, lipid that is associated with cancer. Such antigen can be expressed on malignant cells or in the tumor microenvironment such as on tumor-associated blood vessels, extracellular matrix, mesenchymal stroma, or immune infiltrates.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Proteins

The invention provides multi-specific binding proteins that bind BCMA on a cancer cell and the NKG2D receptor and CD16 receptor on natural killer cells to activate the natural killer cell. The multi-specific binding proteins are useful in the pharmaceutical compositions and therapeutic methods described herein. Binding of the multi-specific binding protein to the NKG2D receptor and CD16 receptor on natural killer cell enhances the activity of the natural killer cell toward destruction of a cancer cell. Binding of the multi-specific binding protein to BCMA on a cancer cell brings the cancer cell into proximity to the natural killer cell, which facilitates direct and indirect destruction of the cancer cell by the natural killer cell. Further description of exemplary multi-specific binding proteins is provided below.

The first component of the multi-specific binding proteins binds to NKG2D receptor-expressing cells, which can include but are not limited to NK cells, γδ T cells and $CD8^+$ αβ T cells. Upon NKG2D-binding, the multi-specific binding proteins may block natural ligands, such as ULBP6 and MICA, from binding to NKG2D.

The second component of the multi-specific binding proteins binds to BCMA-expressing cells, which can include but are not limited to multiple myeloma, acute myelomonocytic leukemia, T cell lymphoma, acute monocytic leukemia, and follicular lymphoma.

The third component for the multi-specific binding proteins binds to cells expressing CD16, an Fc receptor on the surface of leukocytes including natural killer cells, macrophages, neutrophils, eosinophils, mast cells, and follicular dendritic cells.

The multi-specific binding proteins can take several formats as shown in but not limited to the examples below. One format is a heterodimeric, multi-specific antibody that includes a first immunoglobulin heavy chain, a second immunoglobulin heavy chain and an immunoglobulin light chain. The first immunoglobulin heavy chain includes a first Fc (hinge-CH2-CH3) domain, a first variable heavy chain domain and an optional first CH1 heavy chain domain. The immunoglobulin light chain includes a variable light chain domain and a constant light chain domain; together with the first immunoglobulin heavy chain, the immunoglobulin light chain forms an antigen-binding site that binds NKG2D. The second immunoglobulin heavy chain comprises a second Fc (hinge-CH2-CH3) domain, a second variable heavy chain domain and a second CH1 heavy chain domain that may pair with an immunoglobulin light chain identical to the one that pairs with the first immunoglobulin heavy chain, except that when immunoglobulin light chain is paired with the second immunoglobulin heavy chain, the resulting antigen-binding site binds to BCMA. The first Fc domain and second Fc domain together are able to bind to CD16 (FIG. 1).

Figure 2:
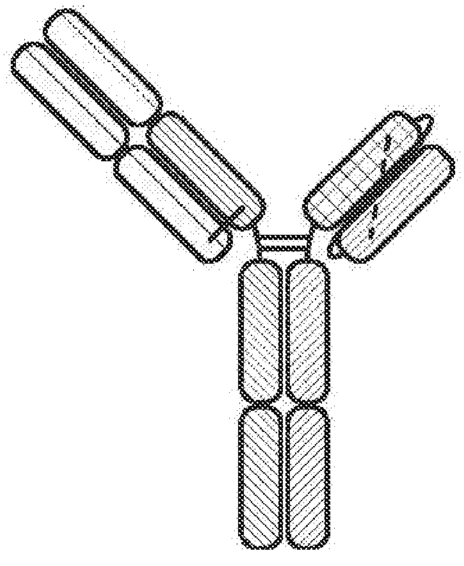
FIG. 2 is a representation of a heterodimeric, multi-specific antibody. NKG2D-binding domain—scFv (right arm); tumor antigen-binding domain (left arm).

Another exemplary format involves a heterodimeric, multi-specific antibody that includes a first immunoglobulin heavy chain, an immunoglobulin light chain and a second immunoglobulin heavy chain. The first immunoglobulin heavy chain includes a first Fc (hinge-CH2-CH3) domain fused via either a linker or an antibody hinge to a single chain Fv (scFv) that binds NKG2D. A variety of linkers could be used for linking the scFv to the first Fc domain or within the scFv itself. In addition, the scFv can incorporate mutations that enable the formation of a disulfide bond to stabilize the overall scFv structure. The scFv can also incorporate mutations to modify the isoelectric point of the overall first immunoglobulin heavy chain and/or to enable more facile downstream purification. The second immunoglobulin heavy chain includes a second Fc (hinge-CH2-CH3) domain and a second variable heavy chain domain and a second optional CH1 heavy chain domain. The immunoglobulin light chain includes a variable light chain domain and a constant light chain domain. The second immunoglobulin heavy chain pairs with the immunoglobulin light chain and binds to BCMA. The first Fc domain and the second Fc domain together are able to bind to CD16 (FIG. 2).

One or more additional binding motifs may be fused to the C-terminus of the constant region CH3 domain, optionally via a linker sequence. In certain embodiments, the antigen-binding site could be a single-chain or disulfide-stabilized variable region (scFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (i.e., $T366W_{CH3A}$ in EU numbering). To accommodate the "knob," a complementary "hole" surface was created on the other CH3 domain (CH3B) by replacing the closest neighboring residues to the knob with smaller ones (i.e., T366S/L368A/$Y407V_{CH3B}$). The "hole" mutation was optimized by structured-guided phage library screening (Atwell S, Ridgway J B, Wells J A, Carter P. Stable heterodimers from remodeling the domain interface of a homodimer using a phage display library. J Mol Biol (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. J Mol Biol (2014) 426(9):1947-57; Mimoto F, Kadono S, Katada H, Igawa T, Kamikawa T, Hattori K. Crystal structure of a novel asymmetrically engineered Fc variant with improved affinity for FcgammaRs. Mol Immunol (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multi-specific binding protein is in the Orthogonal Fab interface (Ortho-Fab) form. In ortho-Fab IgG approach (Lewis S M, Wu X, Pustilnik A, Sereno A, Huang F, Rick H L, et al. Generation of bispecific IgG antibodies by structure-based design of an orthogonal Fab interface. Nat. Biotechnol. (2014) 32(2):191-8), structure-based regional design introduces complementary mutations at the LC and $HC_{VH-CH1}$ interface in only one Fab, without any changes being made to the other Fab.

Figure 13A:
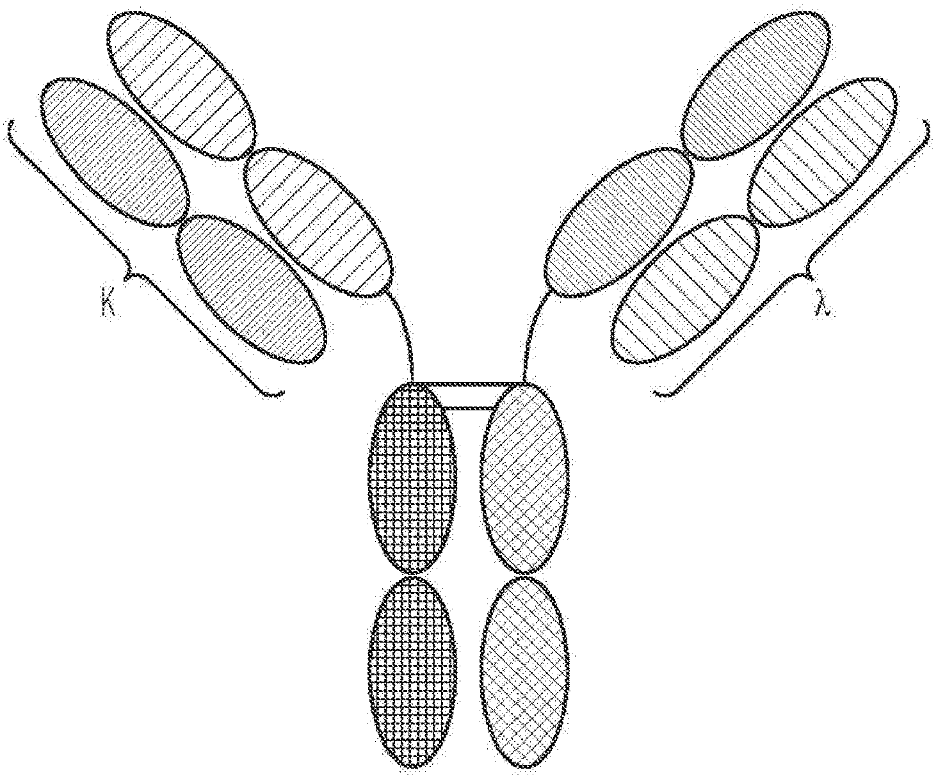
FIGS. 13A-13B are representations of TriNKETs in the κλ-Body forms, which are an heterodimeric constructs with two different Fabs fused to Fc stabilized by heterodimerization mutations: Fab1 targeting antigen 1 contains kappa LC, while second Fab targeting antigen 2 contains lambda LC.
Figure 13B:
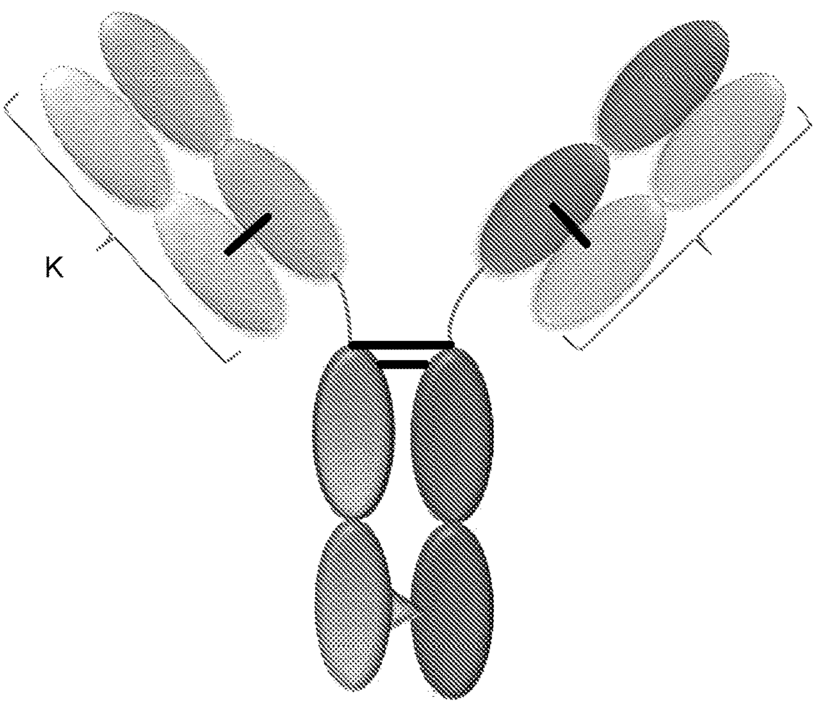

In some embodiments, the multi-specific binding protein is in the 2 in-1 Ig format. In some embodiments, the multi-specific binding protein is in the ES form, which is an heterodimeric construct containing two different Fabs binding to targets 1 and target 2 fused to the $F_C$. Heterodimerization is ensured by electrostatic steering mutations in the Fc. In some embodiments, the multi-specific binding protein is in the κλ-Body form, which is an heterodimeric constructs with two different Fabs fused to Fc stabilized by heterodimerization mutations: Fab1 targeting antigen 1 contains kappa LC, while second Fab targeting antigen 2 contains lambda LC. FIG. 13A is an exemplary representation of one form of a κλ-Body; FIG. 13B is an exemplary representation of another κλ-Body.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies). In some embodiments, the multi-specific binding protein is in the SEED Body form. The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., *Protein Eng. Des. Sel.* (2011, 24(5):447-54)). In some embodiments, the multi-specific binding protein is in the LuZ-Y form, in which leucine zipper is used to induce heterodimerization of two different HCs. (Wranik, B J. et al., *J. Biol. Chem.* (2012), 287:43331-9).

In some embodiments, the multi-specific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., *PNAS* (2010), 107(52); 22611-22616).

In some embodiments, the multi-specific binding protein is in an Oasc-Fab heterodimeric form that includes Fab binding to target 1, and scFab binding to target 2 fused to Fc. Heterodimerization is ensured by mutations in the $F_C$.

In some embodiments, the multi-specific binding protein is in a DuetMab form, which is an heterodimeric construct containing two different Fabs binding to antigens 1 and 2, and $F_C$ stabilized by heterodimerization mutations. Fab 1 and 2 contain differential S—S bridges that ensure correct LC and HC pairing.

In some embodiments, the multi-specific binding protein is in a CrossmAb form, which is an heterodimeric construct with two different Fabs binding to targets 1 and 2, fused to Fc stabilized by heterodimerization. CL and CH1 domains and VH and VL domains are switched, e.g., CH1 is fused in-line with VL, while CL is fused in-line with VH.

In some embodiments, the multi-specific binding protein is in a Fit-Ig form, which is an homodimeric constructs where Fab binding to antigen 2 is fused to the N terminus of HC of Fab that binds to antigen 1. The construct contains wild-type Fc.

Table 1 lists peptide sequences of heavy chain variable domains and light chain variable domains that, in combination, can bind to NKG2D.

TABLE 1

| Clones | Heavy chain variable region amino acid sequence | Light chain variable region amino acid sequence |
|---|---|---|
| ADI-27705 | QVQLQQWGAGLLKPSETLSLTCAVY<br>GGSFSGYYWSWIRQPPGKGLEWIGEI<br>DHSGSTNYNPSLKSRVTISVDTSKNQ<br>FSLKLS SVTAADTAVYYCARARGPW<br>SFDPWGQGTLVTVSS<br>(SEQ ID NO: 1)<br>CDR1 (SEQ ID NO: 64)-GSFSGYYWS<br>CDR2 (SEQ ID NO: 65)-<br>EIDHSGSTNYNPSLKS<br>CDR3 (SEQ ID NO: 66)-<br>ARARGPWSFDP | DIQMTQSPSTLSASVGDRVTITCR<br>ASQSISSWLAWYQQKPGKAPKLL<br>IYKASSLESGVPSRFSGSGSGTEFT<br>LTISSLQPDDFATYYCQQYNSYPI<br>TFGGGTKVEIK<br>(SEQ ID NO: 2) |
| ADI-27724 | QVQLQQWGAGLLKPSETLSLTCAVY<br>GGSFSGYYWSWIRQPPGKGLEWIGEI<br>DHSGSTNYNPSLKSRVTISVDTSKNQ<br>FSLKLSSVTAADTAVYYCARARGPW<br>SFDPWGQGTLVTVSS<br>(SEQ ID NO: 3) | EIVLTQSPGTLSLSPGERATLSCRA<br>SQSVSSSYLAWYQQKPGQAPRLL<br>IYGASSRATGIPDRFSGSGSGTDFT<br>LTISRLEPEDFAVYYCQQYGSSPIT<br>FGGGTKVEIK<br>(SEQ ID NO: 4) |
| ADI-27740<br>(A40) | QVQLQQWGAGLLKPSETLSLTCAVY<br>GGSFSGYYWSWIRQPPGKGLEWIGEI<br>DHSGSTNYNPSLKSRVTISVDTSKNQ<br>FSLKLS SVTAADTAVYYCARARGPW<br>SFDPWGQGTLVTVSS<br>(SEQ ID NO: 5) | DIQMTQSPSTLSASVGDRVTITCR<br>ASQSIGSWLAWYQQKPGKAPKLL<br>IYKASSLESGVPSRFSGSGSGTEFT<br>LTISSLQPDDFATYYCQQYHSFYT<br>FGGGTKVEIK<br>(SEQ ID NO: 6) |
| ADI-27741 | QVQLQQWGAGLLKPSETLSLTCAVY<br>GGSFSGYYWSWIRQPPGKGLEWIGEI<br>DHSGSTNYNPSLKSRVTISVDTSKNQ<br>FSLKLSSVTAADTAVYYCARARGPW<br>SFDPWGQGTLVTVSS<br>(SEQ ID NO: 7) | DIQMTQSPSTLSASVGDRVTITCR<br>ASQSIGSWLAWYQQKPGKAPKLL<br>IYKASSLESGVPSRFSGSGSGTEFT<br>LTISSLQPDDFATYYCQQSNSYYT<br>FGGGTKVEIK<br>(SEQ ID NO: 8) |
| ADI-27743 | QVQLQQWGAGLLKPSETLSLTCAVY<br>GGSFSGYYWSWIRQPPGKGLEWIGEI<br>DHSGSTNYNPSLKSRVTISVDTSKNQ<br>FSLKLSSVTAADTAVYYCARARGPW<br>SFDPWGQGTLVTVSS<br>(SEQ ID NO: 9) | DIQMTQSPSTLSASVGDRVTITCR<br>ASQSISSWLAWYQQKPGKAPKLL<br>IYKASSLESGVPSRFSGSGSGTEFT<br>LTISSLQPDDFATYYCQQYNSYPT<br>FGGGTKVEIK<br>(SEQ ID NO: 10) |

TABLE 1-continued

| Clones | Heavy chain variable region amino acid sequence | Light chain variable region amino acid sequence |
|---|---|---|
| ADI-28153 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWGFDPWGQGTLVTVSS (SEQ ID NO: 11) | ELQMTQSPSSLSASVGDRVTITCRTSQSISSYLNWYQQKPGQPPKLLIYWASTRESGVPDRFSGSGSGTDFTLTISSLQPEDSATYYCQQSYDIPYTFGQGTKLEIK (SEQ ID NO: 12) |
| ADI-28226 (C26) | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 13) | DIQMTQSPSTLSASVGDRVTITCRASQSISSWLAWYQQKPGKAPKLLIYKASSLESGVPSRFSGSGSGTEFTLTISSLQPDDFATYYCQQYGSFPITFGGGTKVEIK (SEQ ID NO: 14) |
| ADI-28154 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 15) | DIQMTQSPSTLSASVGDRVTITCRASQSISSWLAWYQQKPGKAPKLLIYKASSLESGVPSRFSGSGSGTDFTLTISSLQPDDFATYYCQQSKEVPWTFGQGTKVEIK (SEQ ID NO: 16) |
| ADI-29399 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 17) | DIQMTQSPSTLSASVGDRVTITCRASQSISSWLAWYQQKPGKAPKLLIYKASSLESGVPSRFSGSGSGTEFTLTISSLQPDDFATYYCQQYNSFPTFGGGTKVEIK (SEQ ID NO: 18) |
| ADI-29401 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 19) | DIQMTQSPSTLSASVGDRVTITCRASQSIGSWLAWYQQKPGKAPKLLIYKASSLESGVPSRFSGSGSGTEFTLTISSLQPDDFATYYCQQYDIYPTFGGGTKVEIK (SEQ ID NO: 20) |
| ADI-29403 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 21) | DIQMTQSPSTLSASVGDRVTITCRASQSISSWLAWYQQKPGKAPKLLIYKASSLESGVPSRFSGSGSGTEFTLTISSLQPDDFATYYCQQYDSYPTFGGGTKVEIK (SEQ ID NO: 22) |
| ADI-29405 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 23) | DIQMTQSPSTLSASVGDRVTITCRASQSISSWLAWYQQKPGKAPKLLIYKASSLESGVPSRFSGSGSGTEFTLTISSLQPDDFATYYCQQYGSFPTFGGGTKVEIK (SEQ ID NO: 24) |
| ADI-29407 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 25) | DIQMTQSPSTLSASVGDRVTITCRASQSISSWLAWYQQKPGKAPKLLIYKASSLESGVPSRFSGSGSGTEFTLTISSLQPDDFATYYCQQYQSFPTFGGGTKVEIK (SEQ ID NO: 26) |
| ADI-29419 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 27) | DIQMTQSPSTLSASVGDRVTITCRASQSISSWLAWYQQKPGKAPKLLIYKASSLESGVPSRFSGSGSGTEFTLTISSLQPDDFATYYCQQYSSFSTFGGGTKVEIK (SEQ ID NO: 28) |
| ADI-29421 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 29) | DIQMTQSPSTLSASVGDRVTITCRASQSISSWLAWYQQKPGKAPKLLIYKASSLESGVPSRFSGSGSGTEFTLTISSLQPDDFATYYCQQYESYSTFGGGTKVEIK (SEQ ID NO: 30) |
| ADI-29424 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS (SEQ ID NO: 31) | DIQMTQSPSTLSASVGDRVTITCRASQSISSWLAWYQQKPGKAPKLLIYKASSLESGVPSRFSGSGSGTEFTLTISSLQPDDFATYYCQQYDSFITFGGGTKVEIK (SEQ ID NO: 32) |

TABLE 1-continued

| Clones | Heavy chain variable region amino acid sequence | Light chain variable region amino acid sequence |
|---|---|---|
| ADI-29425 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 33) | DIQMTQSPSTLSASVGDRVTITCR ASQSISSWLAWYQQKPGKAPKLL IYKASSLESGVPSRFSGSGSGTEFT LTISSLQPDDFATYYCQQYQSYPT FGGGTKVEIK (SEQ ID NO: 34) |
| ADI-29426 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 35) | DIQMTQSPSTLSASVGDRVTITCR ASQSIGSWLAWYQQKPGKAPKLL IYKASSLESGVPSRFSGSGSGTEFT LTISSLQPDDFATYYCQQYHSFPT FGGGTKVEIK (SEQ ID NO: 36) |
| ADI-29429 | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 37) | DIQMTQSPSTLSASVGDRVTITCR ASQSIGSWLAWYQQKPGKAPKLL IYKASSLESGVPSRFSGSGSGTEFT LTISSLQPDDFATYYCQQYELYSY TFGGGTKVEIK (SEQ ID NO: 38) |
| ADI-29447 (F47) | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 39) | DIQMTQSPSTLSASVGDRVTITCR ASQSISSWLAWYQQKPGKAPKLL IYKASSLESGVPSRFSGSGSGTEFT LTISSLQPDDFATYYCQQYDTFITF GGGTKVEIK (SEQ ID NO: 40) |
| ADI-27727 | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARGDSSI RHAYYYYGMDVWGQGTTVTVSS (SEQ ID NO: 41) CDR1 (SEQ ID NO: 67)- GTFSSYAIS CDR2 (SEQ ID NO: 68)- GIIPIFGTANYAQKFQG CDR3 (SEQ ID NO: 69)- ARGDSSIRHAYYYYGMDV | DIVMTQSPDSLAVSLGERATINCK SSQSVLYSSNNKNYLAWYQQKP GQPPKLLIYWASTRESGVPDRFSG SGSGTDFTLTISSLQAEDVAVYYC QQYYSTPITFGGGTKVEIK (SEQ ID NO: 42) CDR1 (SEQ ID NO: 70)- KSSQSVLYSSNNKNYLA CDR2 (SEQ ID NO: 71)- WASTRES CDR3 (SEQ ID NO: 72)- QQYYSTPIT |
| ADI-29443 (F43) | QLQLQESGPGLVKPSETLSLTCTVSG GSISSSSYYWGWIRQPPGKGLEWIGSI YYSGSTYYNPSLKSRVTISVDTSKNQ FSLKLSSVTAADTAVYYCARGSDRF HPYFDYWGQGTLVTVSS (SEQ ID NO: 43) CDR1 (SEQ ID NO: 73)- GSISSSSYYWG CDR2 (SEQ ID NO: 74)- SIYYSGSTYYNPSLKS CDR3 (SEQ ID NO: 75)- ARGSDRFHPYFDY | EIVLTQSPATLSLSPGERATLSCRA SQSVSRYLAWYQQKPGQAPRLLI YDASNRATGIPARFSGSGSGTDFT LTISSLEPEDFAVYYCQQFDTWPP TFGGGTKVEIK (SEQ ID NO: 44) CDR1 (SEQ ID NO: 76)- RASQSVSRYLA CDR2 (SEQ ID NO: 77)- DASNRAT CDR3 (SEQ ID NO: 78)- QQFDTWPPT |
| ADI-29404 (F04) | QVQLQQWGAGLLKPSETLSLTCAVY GGSFSGYYWSWIRQPPGKGLEWIGEI DHSGSTNYNPSLKSRVTISVDTSKNQ FSLKLSSVTAADTAVYYCARARGPW SFDPWGQGTLVTVSS (SEQ ID NO: 95) | DIQMTQSPSTLSASVGDRVTITCR ASQSISSWLAWYQQKPGKAPKLL IYKASSLESGVPSRFSGSGSGTEFT LTISSLQPDDFATYYCEQYDSYPT FGGGTKVEIK (SEQ ID NO: 96) |
| ADI-28200 | QVQLVQSGAEVKKPGSSVKVSCKAS GGTFSSYAISWVRQAPGQGLEWMGG IIPIFGTANYAQKFQGRVTITADESTS TAYMELSSLRSEDTAVYYCARRGRK ASGSFYYYYGMDVWGQGTTVTVSS (SEQ ID NO: 97) | DIVMTQSPDSLAVSLGERATINCE SSQSLLNSGNQKNYLTWYQQKPG QPPKPLIYWASTRESGVPDRFSGS GSGTDFTLTISSLQAEDVAVYYCQ NDYSYPYTFGQGTKLEIK (SEQ ID NO: 98) |
| ADI-27744 (A44) | EVQLLESGGGLVQPGGSLRLSCAASG FTFSSYAMSWVRQAPGKGLEWVSAI SGSGGSTYYADSVKGRFTISRDNSKN TLYLQMNSLRAEDTAVYYCAKDGG YYDSGAGDYWGQGTLVTVSS (SEQ ID NO: 99) CDR1 (SEQ ID NO: 105)-FTFSSYAMS CDR2 (SEQ ID NO: 106)- | DIQMTQSPSSVSASVGDRVTITCR ASQGIDSWLAWYQQKPGKAPKL LIYAASSLQSGVPSRFSGSGSGTD FTLTISSLQPEDFATYYCQQGVSY PRTFGGGTKVEIK (SEQ ID NO: 100) CDR1 (SEQ ID NO: 108)- RASQGIDSWLA |

TABLE 1-continued

| Clones | Heavy chain variable region amino acid sequence | Light chain variable region amino acid sequence |
|---|---|---|
| | AISGSGGSTYYADSVKG<br>CDR3 (SEQ ID NO: 107)-<br>AKDGGYYDSGAGDY | CDR2 (SEQ ID NO: 109)-AASSLQS<br>CDR3 (SEQ ID NO: 110)-<br>QQGVSYPRT |
| ADI-27749<br>(A49) | EVQLVESGGGLVKPGGSLRLSCAAS<br>GFTFSSYSMNWVRQAPGKGLEWVSS<br>ISSSSSYIYYADSVKGRFTISRDNAKN<br>SLYLQMNSLRAEDTAVYYCARGAP<br>MGAAAGWFDPWGQGTLVTVSS<br>(SEQ ID NO: 101)<br>CDR1 (SEQ ID NO: 111)-FTFSSYSMN<br>CDR2 (SEQ ID NO: 112)-<br>SISSSSSYIYYADSVKG<br>CDR3 (SEQ ID NO: 113)-<br>ARGAPMGAAAGWFDP | DIQMTQSPSSVSASVGDRVTITCR<br>ASQGISSWLAWYQQKPGKAPKLL<br>IYAASSLQSGVPSRFSGSGSGTDF<br>TLTISSLQPEDFATYYCQQGVSFP<br>RTFGGGTKVEIK<br>(SEQ ID NO: 102)<br>CDR1 (SEQ ID NO: 114)-<br>RASQGISSWLA<br>CDR2 (SEQ ID NO: 115)-AASSLQS<br>CDR3 (SEQ ID NO: 116)-<br>QQGVSFPRT |
| ADI-29463<br>(F63) | QVQLVQSGAEVKKPGASVKVSCKAS<br>GYTFTGYYMHWVRQAPGQGLEWM<br>GWINPNSGGTNYAQKFQGRVTMTR<br>DTSISTAYMELSRLRSDDTAVYYCAR<br>DTGEYYDTDDHGMDVWGQGTTVTV<br>SS<br>(SEQ ID NO: 103)<br>CDR1 (SEQ ID NO: 117)-<br>YTFTGYYMH<br>CDR2 (SEQ ID NO: 118)-<br>WINPNSGGTNYAQKFQG<br>CDR3 (SEQ ID NO: 119)-<br>ARDTGEYYDTDDHGMDV | EIVLTQSPGTLSLSPGERATLSCRA<br>SQSVSSNLAWYQQKPGQAPRLLI<br>YGASTRATGIPARFSGSGSGTEFT<br>LTISSLQSEDFAVYYCQQDDYWP<br>PTFGGGTKVEIK<br>(SEQ ID NO: 104)<br>CDR1 (SEQ ID NO: 120)-<br>RASQSVSSNLA<br>CDR2 (SEQ ID NO: 121)-GASTRAT<br>CDR3 (SEQ ID NO: 122)-<br>QQDDYWPPT |

Alternatively, a heavy chain variable domain defined by SEQ ID NO:45 can be paired with a light chain variable domain defined by SEQ ID NO:46 to form an antigen-binding site that can bind to NKG2D, as illustrated in U.S. Pat. No. 9,273,136.

(SEQ ID NO: 45)
QVQLVESGGGLVKPGGSLRLSCAASGFTFSSYGMHWVRQAPGKGLEWVAF

IRYDGSNKYYADSVKGRFTISRDNSKNTLYLQMNSLRAEDTAVYYCAKDR

GLGDGTYPDYWGQGTTVTVSS (SEQ ID NO: 46)
QSALTQPASVSGSPGQSITISCSGSSSNIGNNAVNWYQQLPGKAPKLLIY

YDDLLPSGVSDRFSGSKSGTSAFLAISGLQSEDEADYYCAAWDDSLNGPV

FGGGTKLTVL

Alternatively, a heavy chain variable domain defined by SEQ ID NO:47 can be paired with light chain variable domain defined by SEQ ID NO:48 to form an antigen-binding site that can bind to NKG2D, as illustrated in U.S. Pat. No. 7,879,985.

(SEQ ID NO: 47)
QVHLQESGPGLVKPSETLSLTCTVSDDSISSYYWSWIRQPPGKGLEWIGH

ISYSGSANYNPSLKSRVTISVDTSKNQFSLKLSSVTAADTAVYYCANWDD

AFNIWGQGTMVTVSS (SEQ ID NO: 48)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK

Table 2 lists peptide sequences of heavy chain variable domains and light chain variable domains that, in combination, can bind to BCMA.

TABLE 2

| Clones | Heavy chain variable domain peptide sequence | Light chain variable domain peptide sequence |
|---|---|---|
| 1<br>(US14,776,649) | QVQLVQSGAEVKKPGASVKVSC<br>KASGYSFPDYYINWVRQAPGQG<br>LEWMGWIYFASGNSEYNQKFTG<br>RVTMTRDTSSSTAYMELSSLRSE<br>DTAVYFCASLYDYDWYFDVWG<br>QGTMVTVSS<br>(SEQ ID NO: 49)<br>CDR1 (SEQ ID NO: 50)-DYYIN<br>CDR2 (SEQ ID NO: 51)-<br>WIYFASGNSEYNQKFTG<br>CDR3 (SEQ ID NO: 52)-<br>LYDYDWYFDV | DIVMTQTPLSLSVTPGEPASISCK<br>SSQSLVHSNGNTYLHWYLQKPG<br>QSPQLLIYKVSNRFSGVPDRFSG<br>SGSGADFTLKISRVEAEDVGVY<br>YCAETSHVPWTFGQGTKLEIK<br>(SEQ ID NO: 53)<br>or<br>DIVMTQTPLSLSVTPGQPASISC<br>KSSQSLVHSNGNTYLHWYLQKP<br>GQSPQLLIYKVSNRFSGVPDRFS<br>GSGSGTDFTLKISRVEAEDVGIY<br>YCSQSSIYPWTFGQGTKLEIK<br>(SEQ ID NO: 54)<br>CDR1 (SEQ ID NO: 55)- |

TABLE 2-continued

| Clones | Heavy chain variable domain peptide sequence | Light chain variable domain peptide sequence |
|---|---|---|
| | | KSSQSLVHSNGNTYLH<br>CDR2 (SEQ ID NO: 56)-<br>KVSNRFS<br>CDR3-AETSHVPWT (SEQ ID NO: 57) or SQSSIYPWT (SEQ ID NO: 58) |
| 2<br>(PCT/US15/64269) | QIQLVQSGPELKKPGETVKISCK ASGYTFTDYSINWVKRAPGKGL KWMGWINTETREPAYAYDFRGR FAFSLETSASTAYLQINNLKYEDT ATYFCALDYSYAMDYWGQGTS VTVSS<br>(SEQ ID NO: 59)<br>CDR1 (SEQ ID NO: 79-DYSIN<br>CDR2 (SEQ ID NO: 80)-<br>WINTETREPAYAYDFR<br>CDR3 (SEQ ID NO: 81)-<br>DYSYAMDY | DIVLTQSPPSLAMSLGKRATISC RASESVTILGSHLIHWYQQKPG QPPTLLIQLASNVQTGVPARFSG SGSRTDFTLTIDPVEEDDVAVYY CLQSRTIPRTFGGGTKLEIK<br>(SEQ ID NO: 60)<br>CDR1 (SEQ ID NO: 82)-<br>RASESVTILGSHLIH<br>CDR2 (SEQ ID NO: 83)-<br>LASNVQT<br>CDR3 (SEQ ID NO: 84)-<br>LQSRTIPRT |
| 3<br>(US14,122,391) | QVQLVQSGAEVKKPGSSVKVSC KASGGTFSNYWMHWVRQAPGQ GLEWMGATYRGHSDTYYNQKF KGRVTITADKSTSTAYMELSSLR SEDTAVYYCARGAIYNGYDVLD NWGQGTLVTVSS<br>(SEQ ID NO: 61)<br>CDR1 (SEQ ID NO: 85)-NYWMH<br>CDR2 (SEQ ID NO: 86)-<br>ATYRGHSDTYYNQKFKG<br>CDR3 (SEQ ID NO: 87)-<br>GAIYNGYDVLDN | DIQMTQSPSSLSASVGDRVTITC SASQDISNYLNWYQQKPGKAPK LLIYYTSNLHSGVPSRFSGSGSG TDFTLTISSLQPEDFATYYCQQY RKLPWTFGQGTKLEIKR<br>(SEQ ID NO: 62)<br>CDR1 (SEQ ID NO: 88)-<br>SASQDISNYLN<br>CDR2 (SEQ ID NO: 89)-<br>YTSNLHS<br>CDR3 (SEQ ID NO: 90)-<br>QQYRKLPWT |
| 4<br>(US20170051068) | QLQLQESGPGLVKPSETLSLTCT VSGGSISSSSYFWGWIRQPPGKG LEWIGSIYYSGITYYNPSLKSRVT ISVDTSKNQFSLKLSSVTAADTA VYYCARHDGATAGLFDYWGQG TLVTVSS (SEQ ID NO: 123)<br>CDR1: SSSYFWG (SEQ ID NO: 125)<br>CDR2: SIYYSGITYYNPSLKS (SEQ ID NO: 126)<br>CDR3: HDGATAGLFDY (SEQ ID NO: 127) | SYVLTQPPSVSVAPGQTARITCG GNNIGSKSVHWYQQPPGQAPV VVVYDDSDRPSGIPER FSGSNSGNTA TLTISRVEAGDEAVYYCQVW DSSSDHVVFGGGTKLTVL<br>(SEQ ID NO: 124)<br>CDR1: GGNNIGSKSVH (SEQ ID NO: 128)<br>CDR2: DDSDRPS (SEQ ID NO: 129)<br>CDR3: QVWDSSSDHVV (SEQ ID NO: 130) |
| 5<br>(WO2017021450) | EVQLLESGGGLVQPGGSLRLSCA ASGFTFSDNAMGWVRQAPGKGL EWVSAISGPGSSTYYADSVKGRF TISRDNSKNTLYLQMNSLRAEDT AVYYCAKVLGWFDYWGQGTLV TVSS (SEQ ID NO: 93)<br>CDR1: DNAMG (SEQ ID NO: 131) or SGFTFSDNAMG (SEQ ID NO: 143)<br>CDR2: AISGPGSSTYYADSVK (SEQ ID NO: 132)<br>CDR3: VLGWFDY (SEQ ID NO: 133) | EIVLTQSPGTLSLSPGERATLSCR ASQSVSDEYLSWYQQKPGQAPR LLIHSASTRATGIPDRFSGSGSGT DFTLAISRLEPEDFAVYYCQQY GYPPDFTFGQGTKVEIK (SEQ ID NO: 94)<br>CDR1: RASQSVSDEYLS (SEQ ID NO: 134)<br>CDR2: SASTRAT (SEQ ID NO: 135)<br>CDR3: QQYGYPPDFT (SEQ ID NO: 136) |
| 6<br>(WO2017021450) | EVQLLESGGGLVQPGGSLRLS CAASGFTFSSYAMSWVRQAP GKGLEWVSAISGSGGSTYYA DSVKGRFTISRDNSKNTLYLQ MNSLRAEDTAVYYCAKVLG WFDYWGQGTLVTVSS (SEQ ID NO: 91)<br>CDR1: SYAMS (SEQ ID NO: 137)<br>CDR2: AISGSGGSTYYADSVK G (SEQ ID NO: 138)<br>CDR3: VLGWFDY (SEQ ID NO: 139) | EIVLTQSPGTLSLSPGERATLS CRASQSVSSSYLAWYQQKPG QAPRLLIYGASSRATGIPDRFS GSGSGTDFTLTISRLEPEDFAV YYCQQYGYPPDFTFGQGTKV EIK (SEQ ID NO: 92)<br>CDR1: RASQSVSSSYLA (SEQ ID NO: 140)<br>CDR2: GASSRAT (SEQ ID NO: 141)<br>CDR3: QQYGYPPDFT (SEQ ID NO: 142) |

Alternatively, novel antigen-binding sites that can bind to BCMA can be identified by screening for binding to the amino acid sequence defined by SEQ ID NO:63.

SEQ ID NO: 63

```
MLQMAGQCSQNEYFDSLLHACIPCQLRCSSNTPPLTCQRYCNASVTNSVK

GTNAILWTCLGLSLIISLAVFVLMFLLRKINSEPLKDEFKNTGSGLLGMA

NIDLEKSRTGDEIILPRGLEYTVEECTCEDCIKSKPKVDSDHCFPLPAME

EGATILVTTKTNDYCKSLPAALSATEIEKSISAR
```

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al, Nature, 406(6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without CH1 domain. In some embodiments, the amino acid sequence of the constant region is at least 90% identical to a human antibody constant region, such as an human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Amino acid substitutions could be selected from the following sets of substitutions shown in Table 3.

TABLE 3

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 4.

TABLE 4

| | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 5.

TABLE 5

| | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |

TABLE 5-continued

| | First Polypeptide | Second Polypeptide |
|---|---|---|
| Set 5 | T366K/L351K | L351D/Y349D/L368E |
| Set 6 | E356K/D399K | K392D/K409D |

Alternatively, at least one amino acid substitution in each polypeptide chain could be selected from Table 6.

TABLE 6

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitution could be selected from the following set of substitutions in Table 7, where the position(s) indicated in the First Polypeptide column is replaced by any known negatively-charged amino acid, and the position(s) indicated in the Second Polypeptide Column is replaced by any known positively-charged amino acid.

TABLE 7

| First Polypeptide | Second Polypeptide |
|---|---|
| K392, K370, K409, or K439 | D399, E356, or E357 |

Alternatively, at least one amino acid substitution could be selected from the following set of in Table 8, where the position(s) indicated in the First Polypeptide column is replaced by any known positively-charged amino acid, and the position(s) indicated in the Second Polypeptide Column is replaced by any known negatively-charged amino acid.

TABLE 8

| First Polypeptide | Second Polypeptide |
|---|---|
| D399, E356, or E357 | K409, K439, K370, or K392 |

Alternatively, or in addition, the structural stability of a heteromultimer protein may be increased by introducing S354C on either of the first or second polypeptide chain, and Y349C on the opposing polypeptide chain, which forms an artificial disulfide bridge within the interface of the two polypeptides.

The multispecific proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; the first, second, and third expression vectors can be stably transfected together into host cells to produce the multimeric proteins.

To achieve the highest yield of the multi-specific protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific protein. The multispecific proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

II. Characteristics of TriNKETs

In certain embodiments, TriNKETs described herein, which include an NKG2D-binding domain and a binding domain for a tumor associated antigen, bind to cells expressing human NKG2D. In certain embodiments, TriNKETs, which include an NKG2D-binding domain and a binding domain for a tumor associated antigen, bind to the tumor associated antigen at a comparable level to that of a monoclonal antibody having the same tumor associated antigen-binding domain.

The TriNKETs described herein are more effective in reducing tumor growth and killing cancer cells.

In certain embodiments, TriNKETs described herein, which include an NKG2D-binding domain and a binding domain for tumor associated antigen, activate primary human NK cells when culturing with tumor cells expressing the antigen. NK cell activation is marked by the increase in CD107a degranulation and IFNγ cytokine production. Furthermore, compared to a monoclonal antibody that includes the tumor associated antigen-binding domain, TriNKETs show superior activation of human NK cells in the presence of tumor cells expressing the antigen. For example, compared to an anti-BCMA monoclonal antibody, TriNKETs of the present disclosure having a BCMA-binding domain, have a superior activation of human NK cells in the presence of BCMA-expressing cancer cells.

In certain embodiments, TriNKETs described herein, which include an NKG2D-binding domain and a binding domain for a tumor associated antigen, enhance the activity of rested and IL-2-activated human NK cells in the presence of tumor cells expressing the antigen. Rested NK cells showed less background IFNγ production and CD107a degranulation than IL-2-activated NK cells. In certain embodiments, rested NK cells show a greater change in IFNγ production and CD107a degranulation compared to IL-2-activated NK cells. In certain embodiments, IL-2-activated NK cells show a greater percentage of cells becoming IFNγ+; CD107a+ after stimulation with TriNKETs.

In certain embodiments, TriNKETs described herein, which include an NKG2D-binding domain and a binding domain for tumor associated antigen BCMA, enhance the cytotoxic activity of rested and IL-2-activated human NK cells in the presence of tumor cells expressing the antigen. Furthermore, TriNKETs (e.g., A40-TriNKET, A44-TriNKET, A49-TriNKET, C26-TriNKET, F04-TriNKET, F43-TriNKET, F47-TriNKET, and F63-TriNKET), which include a binding domain for tumor associated antigen BCMA more potently direct activated and rested NK cell responses against the tumor cells, compared to a monoclonal antibody that includes the same tumor associated antigen-binding site. In certain embodiments, TriNKETs offer advantage against tumor cells expressing medium and low BCMA compared to monoclonal antibodies that include the BCMA-binding site. Therefore, a therapy including TriNKETs can be superior to an anti-BCMA monoclonal antibody therapy.

In certain embodiments, compared to monoclonal antibodies, TriNKETs described herein (e.g., A40-TriNKET, A44-TriNKET, A49-TriNKET, C26-TriNKET, F04-TriNKET, F43-TriNKET, F47-TriNKET, and F63-TriNKET), which include a binding domain for tumor associated antigen BCMA are advantageous in treating cancers with high expression of Fc receptor (FcR), or cancers residing in a tumor microenvironment with high levels of FcR. Monoclonal antibodies exert their effects on tumor growth through multiple mechanisms including ADCC, CDC, phagocytosis, and signal blockade amongst others. Amongst FcγRs, CD16 has the lowest affinity for IgG Fc; FcγRI (CD64) is the high-affinity FcR, which binds about 1000 times more strongly to IgG Fc than CD16. CD64 is normally expressed on many hematopoietic lineages such as the myeloid lineage, and can be expressed on tumors derived from these cell types, such as acute myeloid leukemia (AML). Immune cells infiltrating into the tumor, such as MDSCs and monocytes, also express CD64 and are known to infiltrate the tumor microenvironment. Expression of CD64 by the tumor or in the tumor microenvironment can have a detrimental effect on monoclonal antibody therapy. Expression of CD64 in the tumor microenvironment makes it difficult for these antibodies to engage CD16 on the surface of NK cells, as the antibodies prefer to bind the high-affinity receptor. TriNKETs, through targeting two activating receptors on the surface of NK cells, can overcome the detrimental effect of CD64 expression (either on tumor or tumor microenvironment) on monoclonal antibody therapy. Regardless of CD64 expression on the tumor cells, TriNKETs are able to mediate human NK cell responses against all tumor cells, because dual targeting of two activating receptors on NK cells provides stronger specific binding to NK cells.

In some embodiments, TriNKETs described herein (e.g., A40-TriNKET, A44-TriNKET, A49-TriNKET, C26-TriNKET, F04-TriNKET, F43-TriNKET, F47-TriNKET, and F63-TriNKET), which include a binding domain for tumor associated antigen BCMA, provide a better safety profile through reduced on-target off-tumor side effects. Natural killer cells and CD8 T cells are both able to directly lyse tumor cells, although the mechanisms through which NK cells and CD8 T cell recognize normal self from tumor cells differ. The activity of NK cells is regulated by the balance of signals from activating (NCRs, NKG2D, CD16, etc.) and inhibitory (KIRs, NKG2A, etc.) receptors. The balance of these activating and inhibitory signals allow NK cells to determine healthy self-cells from stressed, virally infected, or transformed self-cells. This 'built-in' mechanism of self-tolerance will help protect normal healthy tissue from NK cell responses. To extend this principle, the self-tolerance of NK cells will allow TriNKETs to target antigens expressed both on self and tumor without off tumor side effects, or with an increased therapeutic window. Unlike natural killer cells, T cells require recognition of a specific peptide presented by MHC molecules for activation and effector functions. T cells have been the primary target of immunotherapy, and many strategies have been developed to redirect T cell responses against the tumor. T cell bispecifics, checkpoint inhibitors, and CAR-T cells have all been approved by the FDA, but often suffer from dose-limiting toxicities. T cell bispecifics and CAR-T cells work around the TCR-MHC recognition system by using binding domains to target antigens on the surface of tumor cells, and using engineered signaling domains to transduce the activation signals into the effector cell. Although effective at eliciting an anti-tumor immune response these therapies are often coupled with cytokine release syndrome (CRS), and on-target off-tumor side effects. TriNKETs are unique in this context as they will not 'override' the natural systems of NK cell activation and inhibition. Instead, TriNKETs are designed to sway the balance, and provide additional activation signals to the NK cells, while maintaining NK tolerance to healthy self.

In some embodiments, TriNKETs described herein including an NKG2D-binding domain (e.g., A40-TriNKET, A44-TriNKET, A49-TriNKET, C26-TriNKET, F04-TriNKET, F43-TriNKET, F47-TriNKET, and F63-TriNKET and a binding domain for tumor associated antigen BCMA delay progression of the tumor more effectively than monoclonal antibodies that include the same tumor antigen-binding domain. In some embodiments, TriNKETs including an NKG2D-binding domain and tumor antigen BCMA-binding domain are more effective against cancer metastases than monoclonal antibodies that include the anti-BCMA-binding domain.

III. Therapeutic Applications

The invention provides methods for treating cancer using a multi-specific binding protein described herein and/or a pharmaceutical composition described herein. The methods may be used to treat a variety of cancers which express BCMA by administering to a patient in need thereof a therapeutically effective amount of a multi-specific binding protein described herein.

The therapeutic method can be characterized according to the cancer to be treated. For example, in certain embodiments, the cancers are blood or bone marrow derived. Exemplary ones include multiple myeloma, acute myelomonocytic leukemia, T cell lymphoma, acute monocytic leukemia and follicular lymphoma. T-cell lymphomas can include precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

In certain embodiments, the cancer is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma.

In certain other embodiments, the cancer is a solid tumor, such as brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

The cancer to be treated can be characterized according to the presence of a particular antigen expressed on the surface of the cancer cell. In certain embodiments, the cancer cell can expresses one or more of the following in addition to BCMA: CD2, CD19, CD20, CD30, CD38, CD40, CD52, CD70, EGFR/ERBB1, IGF1R, HER3/ERBB3, HER4/ERBB4, MUC1, cMET, SLAMF7, PSCA, MICA, MICB, TRAILR1, TRAILR2, MAGE-A3, B7.1, B7.2, CTLA4, and PD1.

IV. Combination Therapy

Another aspect of the invention provides for combination therapy. Multi-specific binding proteins described herein be used in combination with additional therapeutic agents to treat the cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxyadenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

The intravenous drug delivery formulation of the present disclosure may be contained in a bag, a pen, or a syringe. In certain embodiments, the bag may be connected to a channel comprising a tube and/or a needle. In certain embodiments, the formulation may be a lyophilized formulation or a liquid formulation. In certain embodiments, the formulation may freeze-dried (lyophilized) and contained in about 12-60 vials. In certain embodiments, the formulation may be freeze-dried and 45 mg of the freeze-dried formulation may be contained in one vial. In certain embodiments, the about 40 mg-about 100 mg of freeze-dried formulation may be contained in one vial. In certain embodiments, freeze dried formulation from 12, 27, or 45 vials are combined to obtained a therapeutic dose of the protein in the intravenous drug formulation. In certain embodiments, the formulation may be a liquid formulation and stored as about 250 mg/vial to about 1000 mg/vial. In certain embodiments, the formulation may be a liquid formulation and stored as about 600 mg/vial. In certain embodiments, the formulation may be a liquid formulation and stored as about 250 mg/vial.

This present disclosure could exist in a liquid aqueous pharmaceutical formulation including a therapeutically effective amount of the protein in a buffered solution forming a formulation.

These compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents. The composition in solid form can also be packaged in a container for a flexible quantity.

In certain embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

In certain embodiments, an aqueous formulation is prepared including the protein of the present disclosure in a pH-buffered solution. The buffer of this invention may have a pH ranging from about 4 to about 8, e.g., from about 4.5 to about 6.0, or from about 4.8 to about 5.5, or may have a pH of about 5.0 to about 5.2. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g. sodium acetate), succinate (such as sodium succinate), gluconate, histidine, citrate and other organic acid buffers.

In certain embodiments, the formulation includes a buffer system which contains citrate and phosphate to maintain the pH in a range of about 4 to about 8. In certain embodiments the pH range may be from about 4.5 to about 6.0, or from about pH 4.8 to about 5.5, or in a pH range of about 5.0 to about 5.2. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/ml of citric acid (e.g., 1.305 mg/ml), about 0.3 mg/ml of sodium citrate (e.g., 0.305 mg/ml), about 1.5 mg/ml of disodium phosphate dihydrate (e.g. 1.53 mg/ml), about 0.9 mg/ml of sodium dihydrogen phosphate dihydrate (e.g., 0.86), and about 6.2 mg/ml of sodium chloride (e.g., 6.165 mg/ml). In certain embodiments, the buffer system includes 1-1.5 mg/ml of citric acid, 0.25 to 0.5 mg/ml of sodium citrate, 1.25 to 1.75 mg/ml of disodium phosphate dihydrate, 0.7 to 1.1 mg/ml of sodium dihydrogen phosphate dihydrate, and 6.0 to 6.4 mg/ml of sodium chloride. In certain embodiments, the pH of the formulation is adjusted with sodium hydroxide.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g. mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/ml. In certain embodiments, the concentration of mannitol may be about 7.5 to 15 mg/ml. In certain embodiments, the concentration of mannitol may be about 10-14 mg/ml. In certain embodiments, the concentration of mannitol may be about 12 mg/ml. In certain embodiments, the polyol sorbitol may be included in the formulation.

A detergent or surfactant may also be added to the formulation. Exemplary detergents include nonionic detergents such as polysorbates (e.g. polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or Tween 80. Tween 80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In embodiments, the protein product of the present disclosure is formulated as a liquid formulation. The liquid formulation may be presented at a 10 mg/mL concentration in either a USP/Ph Eur type I 50R vial closed with a rubber stopper and sealed with an aluminum crimp seal closure. The stopper may be made of elastomer complying with USP and Ph Eur. In certain embodiments vials may be filled with 61.2 mL of the protein product solution in order to allow an extractable volume of 60 mL. In certain embodiments, the liquid formulation may be diluted with 0.9% saline solution.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative.

In certain embodiments, the pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In addition to aggregation, deamidation is a common product variant of peptides and proteins that may occur during fermentation, harvest/cell clarification, purification, drug substance/drug product storage and during sample analysis. Deamidation is the loss of $NH_3$ from a protein forming a succinimide intermediate that can undergo hydrolysis. The succinimide intermediate results in a 17 u mass decrease of the parent peptide. The subsequent hydrolysis results in an 18 u mass increase. Isolation of the succinimide intermediate is difficult due to instability under aqueous conditions. As such, deamidation is typically detectable as 1 u mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation.

In certain embodiments, the liquid formulation of the present disclosure may be preserved under conditions of pH and humidity to prevent deamination of the protein product.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

A preservative may be optionally added to the formulations herein to reduce bacterial action. The addition of a preservative may, for example, facilitate the production of a multi-use (multiple-dose) formulation.

Intravenous (IV) formulations may be the preferred administration route in particular instances, such as when a patient is in the hospital after transplantation receiving all drugs via the IV route. In certain embodiments, the liquid formulation is diluted with 0.9% Sodium Chloride solution before administration. In certain embodiments, the diluted drug product for injection is isotonic and suitable for administration by intravenous infusion.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

A preservative may be optionally added to the formulations herein to reduce bacterial action. The addition of a preservative may, for example, facilitate the production of a multi-use (multiple-dose) formulation.

The aqueous carrier of interest herein is one which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g. phosphate-buffered saline), sterile saline solution, Ringer's solution or dextrose solution.

This present disclosure could exist in a lyophilized formulation including the proteins and a lyoprotectant. The lyoprotectant may be sugar, e.g., disaccharides. In certain embodiments, the lycoprotectant may be sucrose or maltose. The lyophilized formulation may also include one or more of a buffering agent, a surfactant, a bulking agent, and/or a preservative.

The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide.

Before lyophilization, the pH of the solution containing the protein of the present disclosure may be adjusted between 6 to 8. In certain embodiments, the pH range for the lyophilized drug product may be from 7 to 8.

In certain embodiments, a salt or buffer components may be added in an amount of 10 mM-200 mM. The salts and/or buffers are pharmaceutically acceptable and are derived from various known acids (inorganic and organic) with "base forming" metals or amines. In certain embodiments, the buffer may be phosphate buffer. In certain embodiments, the buffer may be glycinate, carbonate, citrate buffers, in which case, sodium, potassium or ammonium ions can serve as counterion.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

A preservative may be optionally added to the formulations herein to reduce bacterial action. The addition of a preservative may, for example, facilitate the production of a multi-use (multiple-dose) formulation.

In certain embodiments, the lyophilized drug product may be constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g. phosphate-buffered saline), sterile saline solution, Ringer's solution or dextrose solution.

In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution.

In certain embodiments, the lyophilized protein product of the instant disclosure is constituted to about 4.5 mL water for injection and diluted with 0.9% saline solution (sodium chloride solution).

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308: 33-41, 2001).

In general, dosages based on body weight are from about 0.01 μg to about 100 mg per kg of body weight, such as about 0.01 μg to about 100 mg/kg of body weight, about 0.01 μg to about 50 mg/kg of body weight, about 0.01 μg to about 10 mg/kg of body weight, about 0.01 μg to about 1 mg/kg of body weight, about 0.01 μg to about 100 μg/kg of body weight, about 0.01 μg to about 50 μg/kg of body weight, about 0.01 μg to about 10 μg/kg of body weight, about 0.01 μg to about 1 μg/kg of body weight, about 0.01 μg to about 0.1 μg/kg of body weight, about 0.1 μg to about 100 mg/kg of body weight, about 0.1 μg to about 50 mg/kg of body weight, about 0.1 μg to about 10 mg/kg of body weight, about 0.1 μg to about 1 mg/kg of body weight, about 0.1 μg to about 100 μg/kg of body weight, about 0.1 μg to about 10 μg/kg of body weight, about 0.1 μg to about 1 μg/kg of body weight, about 1 μg to about 100 mg/kg of body weight, about 1 μg to about 50 mg/kg of body weight, about 1 μg to about 10 mg/kg of body weight, about 1 μg to about 1 mg/kg of body weight, about 1 μg to about 100 μg/kg of body weight, about 1 μg to about 50 μg/kg of body weight, about 1 μg to about 10 μg/kg of body weight, about 10 μg to about 100 mg/kg of body weight, about 10 μg to about 50 mg/kg of body weight, about 10 μg to about 10 mg/kg of body weight, about 10 μg to about 1 mg/kg of body weight, about 10 μg to about 100 μg/kg of body weight, about 10 μg to about 50 μg/kg of body weight, about 50 μg to about 100 mg/kg of body weight, about 50 μg to about 50 mg/kg of body weight, about 50 μg to about 10 mg/kg of body weight, about 50 μg to about 1 mg/kg of body weight, about 50 μg to about 100 μg/kg of body weight, about 100 μg to about 100 mg/kg of body weight, about 100 μg to about 50 mg/kg of body weight, about 100 μg to about 10 mg/kg of body weight, about 100 μg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight.

Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

EXAMPLES

The invention now being generally described, will be more readily understood by reference to the following examples, which are included merely for purposes of illustration of certain aspects and embodiments of the present invention, and is not intended to limit the invention.

Example 1—NKG2D-Binding Domains Bind to NKG2D

NKG2D-Binding Domains Bind to Purified Recombinant NKG2D

The nucleic acid sequences of human, mouse or cynomolgus NKG2D ectodomains were fused with nucleic acid sequences encoding human IgG1 Fc domains and introduced into mammalian cells to be expressed. After purification, NKG2D-Fc fusion proteins were adsorbed to wells of microplates. After blocking the wells with bovine serum albumin to prevent non-specific binding, NKG2D-binding domains were titrated and added to the wells pre-adsorbed with NKG2D-Fc fusion proteins. Primary antibody binding was detected using a secondary antibody which was conjugated to horseradish peroxidase and specifically recognizes a human kappa light chain to avoid Fc cross-reactivity. 3,3',5,5'-Tetramethylbenzidine (TMB), a substrate for horseradish peroxidase, was added to the wells to visualize the binding signal, whose absorbance was measured at 450 nM and corrected at 540 nM. An NKG2D-binding domain clone, an isotype control or a positive control (selected from SEQ ID NO: 45-48, or anti-mouse NKG2D clones MI-6 and CX-5 available at eBioscience) was added to each well.

Figure 14:
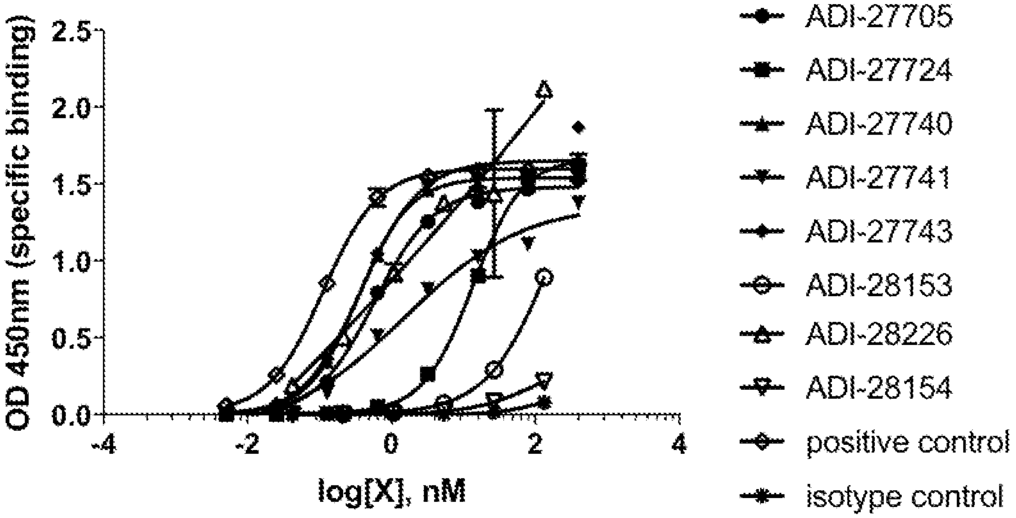
FIG. 14 are line graphs demonstrating the binding affinity of NKG2D-binding domains (listed as clones) to human recombinant NKG2D in an ELISA assay.
Figure 15:
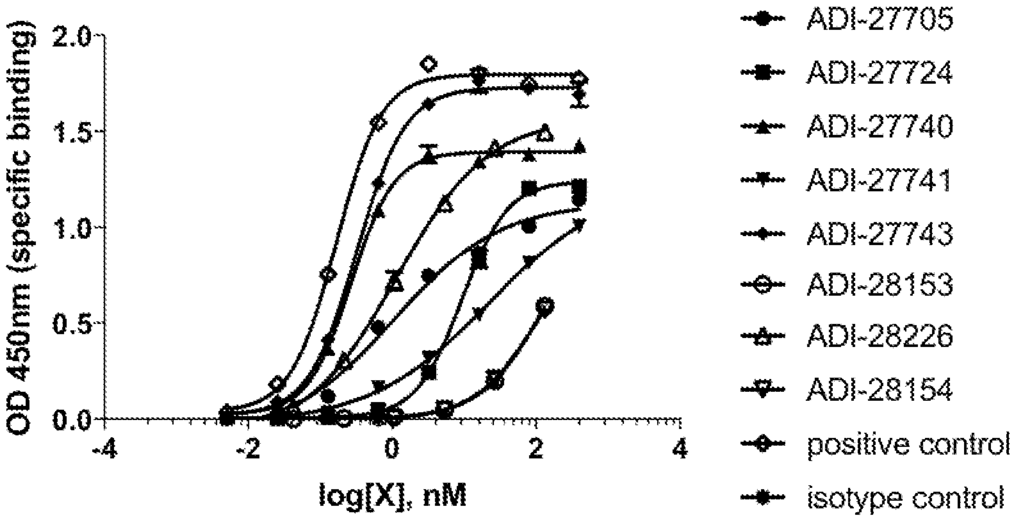
FIG. 15 are line graphs demonstrating the binding affinity of NKG2D-binding domains (listed as clones) to cynomolgus recombinant NKG2D in an ELISA assay.
Figure 16:
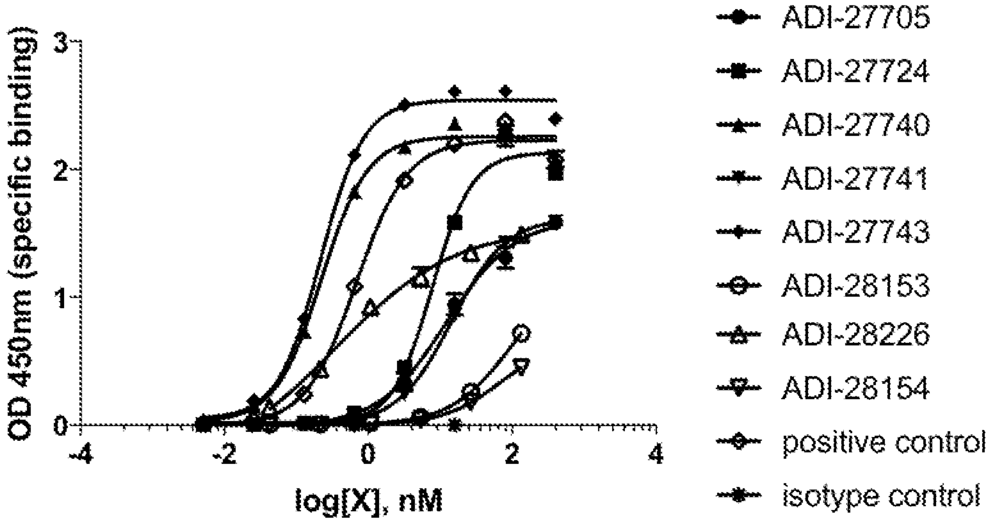
FIG. 16 are line graphs demonstrating the binding affinity of NKG2D-binding domains (listed as clones) to mouse recombinant NKG2D in an ELISA assay.

The isotype control showed minimal binding to recombinant NKG2D-Fc proteins, while the positive control bound strongest to the recombinant antigens. NKG2D-binding domains produced by all clones demonstrated binding across human (FIG. 14), mouse (FIG. 16), and cynomolgus (FIG. 15) recombinant NKG2D-Fc proteins, although with varying affinities from clone to clone. Generally, each anti-NKG2D clone bound to human (FIG. 14) and cynomolgus (FIG. 15) recombinant NKG2D-Fc with similar affinity, but with lower affinity to mouse (FIG. 16) recombinant NKG2D-Fc.

NKG2D-Binding Domains Bind to Cells Expressing NKG2D

EL4 mouse lymphoma cell lines were engineered to express human or mouse NKG2D-CD3 zeta signaling domain chimeric antigen receptors. An NKG2D-binding clone, an isotype control or a positive control was used at a 100 nM concentration to stain extracellular NKG2D expressed on the EL4 cells. The antibody binding was detected using fluorophore conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

Figure 17:
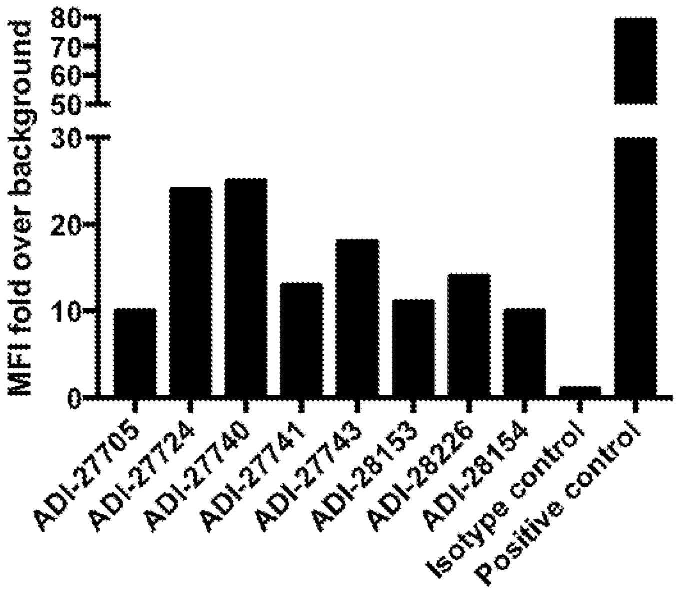
FIG. 17 are bar graphs demonstrating the binding of NKG2D-binding domains (listed as clones) to EL4 cells expressing human NKG2D by flow cytometry showing mean fluorescence intensity (MFI) fold over background.
Figure 18:
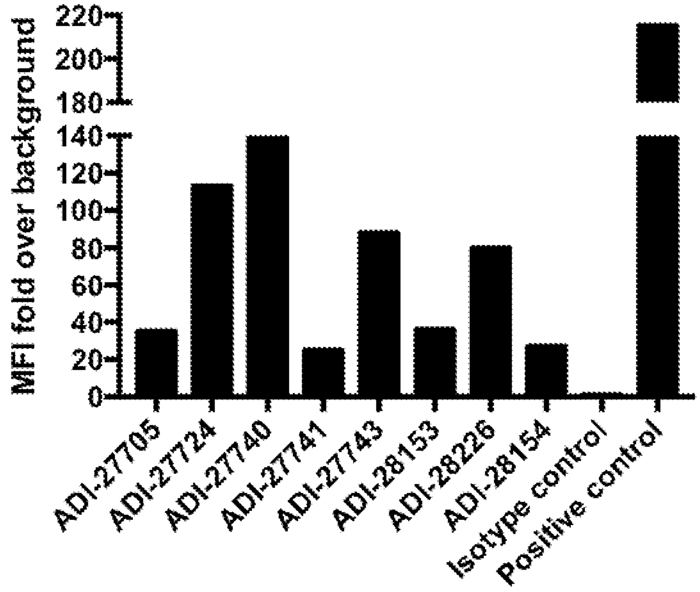
FIG. 18 are bar graphs demonstrating the binding of NKG2D-binding domains (listed as clones) to EL4 cells expressing mouse NKG2D by flow cytometry showing mean fluorescence intensity (MFI) fold over background.

NKG2D-binding domains produced by all clones bound to EL4 cells expressing human and mouse NKG2D. Positive control antibodies (selected from SEQ ID NO:45-48, or anti-mouse NKG2D clones MI-6 and CX-5 available at eBioscience) gave the best FOB binding signal. The NKG2D binding affinity for each clone was similar between cells expressing human NKG2D (FIG. 17) and mouse NKG2D (FIG. 18).

Example 2—NKG2D-Binding Domains Block Natural Ligand Binding to NKG2D

Competition with ULBP-6

Figure 19:
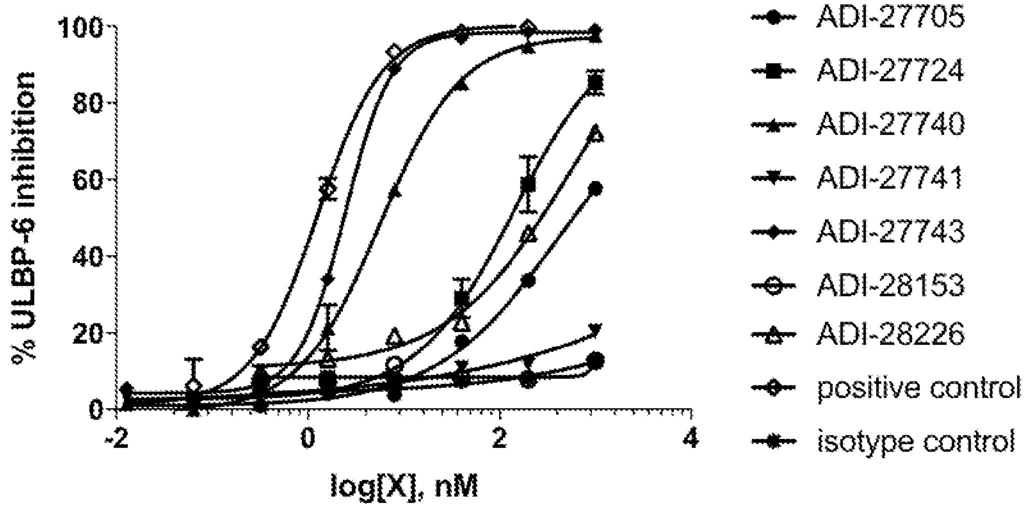
FIG. 19 are line graphs demonstrating specific binding affinity of NKG2D-binding domains (listed as clones) to recombinant human NKG2D-Fc by competing with natural ligand ULBP-6.

Recombinant human NKG2D-Fc proteins were adsorbed to wells of a microplate, and the wells were blocked with bovine serum albumin reduce non-specific binding. A saturating concentration of ULBP-6-His-biotin was added to the wells, followed by addition of the NKG2D-binding domain clones. After a 2-hour incubation, wells were washed and ULBP-6-His-biotin that remained bound to the NKG2D-Fc coated wells was detected by streptavidin conjugated to horseradish peroxidase and TMB substrate. Absorbance was measured at 450 nM and corrected at 540 nM. After subtracting background, specific binding of NKG2D-binding domains to the NKG2D-Fc proteins was calculated from the percentage of ULBP-6-His-biotin that was blocked from binding to the NKG2D-Fc proteins in wells. The positive control antibody (selected from SEQ ID NO:45-48) and various NKG2D-binding domains blocked ULBP-6 binding to NKG2D, while isotype control showed little competition with ULBP-6 (FIG. 19).

Competition with MICA

Figure 20:
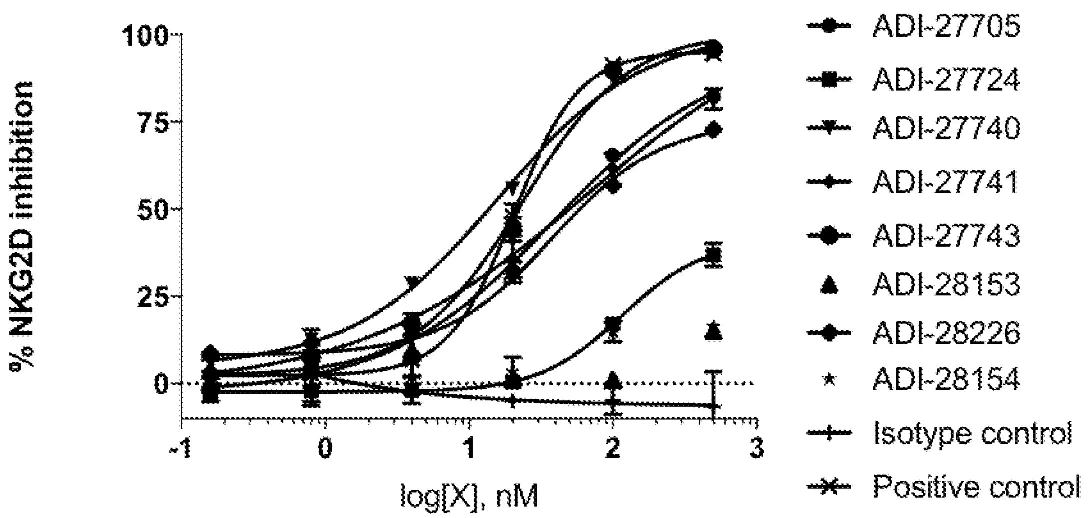
FIG. 20 are line graphs demonstrating specific binding affinity of NKG2D-binding domains (listed as clones) to recombinant human NKG2D-Fc by competing with natural ligand MICA.

Recombinant human MICA-Fc proteins were adsorbed to wells of a microplate, and the wells were blocked with bovine serum albumin to reduce non-specific binding. NKG2D-Fc-biotin was added to wells followed by NKG2D-binding domains. After incubation and washing, NKG2D-Fc-biotin that remained bound to MICA-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the MICA-Fc coated wells. The positive control antibody (selected from SEQ ID NO:45-48) and various NKG2D-binding domains blocked MICA binding to NKG2D, while isotype control showed little competition with MICA (FIG. 20).

Competition with Rae-1 Delta

Figure 21:
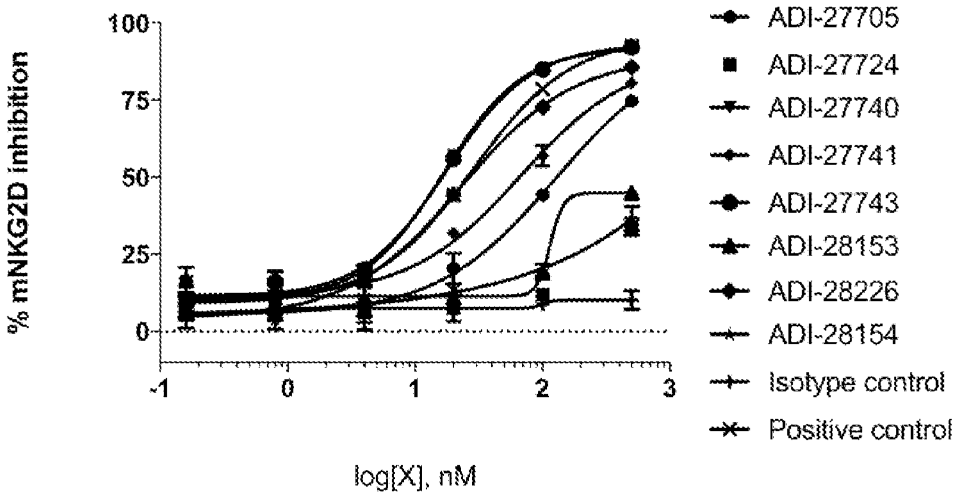
FIG. 21 are line graphs demonstrating specific binding affinity of NKG2D-binding domains (listed as clones) to recombinant mouse NKG2D-Fc by competing with natural ligand Rae-1 delta.

Recombinant mouse Rae-1delta-Fc (purchased from R&D Systems) was adsorbed to wells of a microplate, and the wells were blocked with bovine serum albumin to reduce non-specific binding. Mouse NKG2D-Fc-biotin was added to the wells followed by NKG2D-binding domains. After incubation and washing, NKG2D-Fc-biotin that remained bound to Rae-1delta-Fc coated wells was detected using streptavidin-HRP and TMB substrate. Absorbance was measured at 450 nM and corrected at 540 nM. After subtracting background, specific binding of NKG2D-binding domains to the NKG2D-Fc proteins was calculated from the percentage of NKG2D-Fc-biotin that was blocked from binding to the Rae-1delta-Fc coated wells. The positive control (selected from SEQ ID NO: 45-48, or anti-mouse NKG2D clones MI-6 and CX-5 available at eBioscience) and various NKG2D-binding domain clones blocked Rae-1delta binding to mouse NKG2D, while the isotype control antibody showed little competition with Rae-1delta (FIG. 21).

Example 3—NKG2D-Binding Domain Clones Activate NKG2D

Nucleic acid sequences of human and mouse NKG2D were fused to nucleic acid sequences encoding a CD3 zeta signaling domain to obtain chimeric antigen receptor (CAR) constructs. The NKG2D-CAR constructs were then cloned into a retrovirus vector using Gibson assembly and transfected into expi293 cells for retrovirus production. EL4 cells were infected with viruses containing NKG2D-CAR together with 8 μg/mL polybrene. 24 hours after infection, the expression levels of NKG2D-CAR in the EL4 cells were analyzed by flow cytometry, and clones which express high levels of the NKG2D-CAR on the cell surface were selected.

Figure 22:
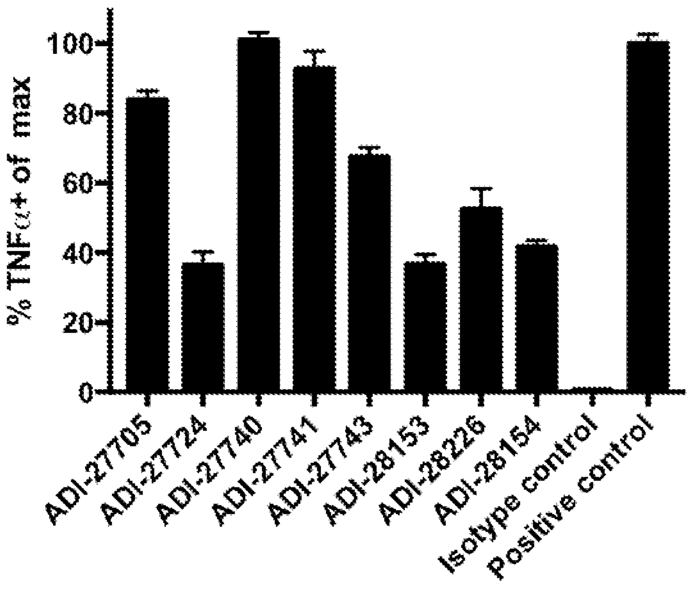
FIG. 22 are bar graphs showing activation of human NKG2D by NKG2D-binding domains (listed as clones) by quantifying the percentage of TNF-alpha positive cells, which express human NKG2D-CD3 zeta fusion proteins.
Figure 23:
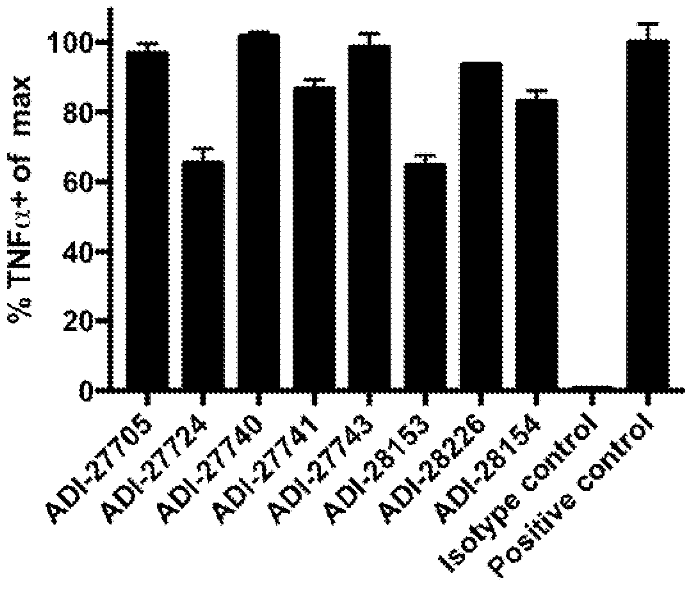
FIG. 23 are bar graphs showing activation of mouse NKG2D by NKG2D-binding domains (listed as clones) by quantifying the percentage of TNF-alpha positive cells, which express mouse NKG2D-CD3 zeta fusion proteins.

To determine whether NKG2D-binding domains activate NKG2D, they were adsorbed to wells of a microplate, and NKG2D-CAR EL4 cells were cultured on the antibody fragment-coated wells for 4 hours in the presence of brefeldin-A and monensin. Intracellular TNF-alpha production, an indicator for NKG2D activation, was assayed by flow cytometry. The percentage of TNF-alpha positive cells was normalized to the cells treated with the positive control. All NKG2D-binding domains activated both human NKG2D (FIG. 22) and mouse (FIG. 23) NKG2D.

Example 4—NKG2D-Binding Domains Activate NK Cells

Primary Human NK Cells

Figure 24:
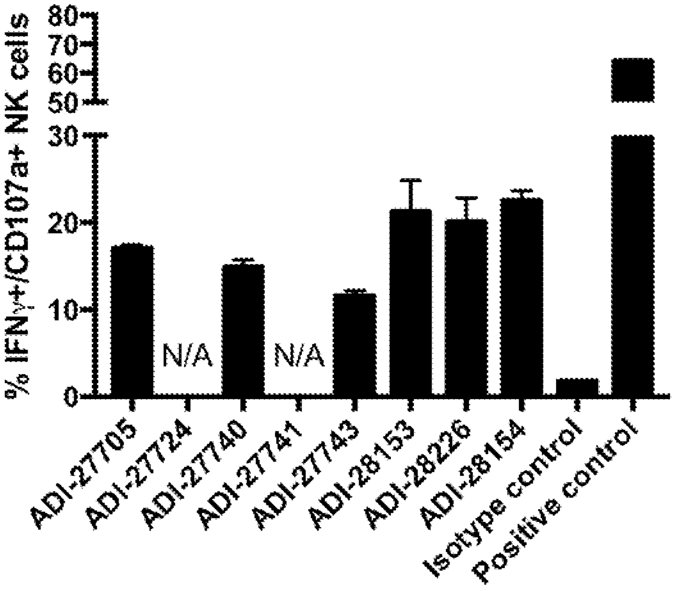
FIG. 24 are bar graphs showing activation of human NK cells by NKG2D-binding domains (listed as clones).
Figure 25:
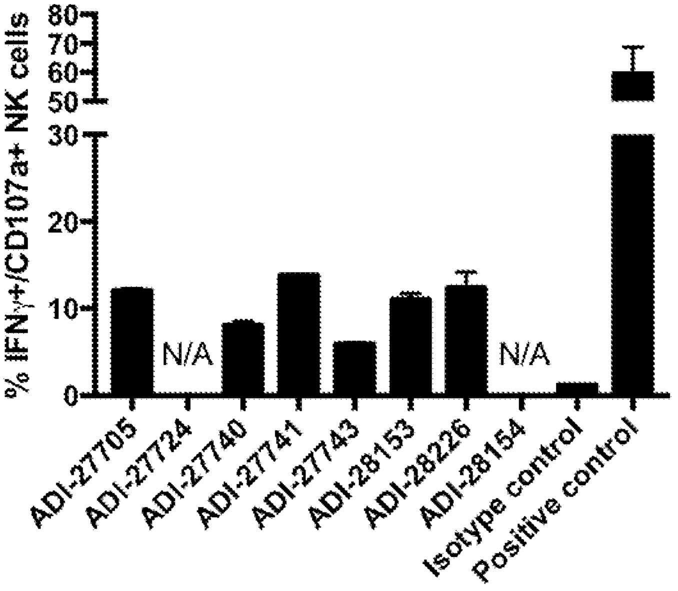
FIG. 25 are bar graphs showing activation of human NK cells by NKG2D-binding domains (listed as clones).

Peripheral blood mononuclear cells (PBMCs) were isolated from human peripheral blood buffy coats using density gradient centrifugation. NK cells ($CD3^-CD56^+$) were isolated using negative selection with magnetic beads from PBMCs, and the purity of the isolated NK cells was typically >95%. Isolated NK cells were then cultured in media containing 100 ng/mL IL-2 for 24-48 hours before they were transferred to the wells of a microplate to which the NKG2D-binding domains were adsorbed, and cultured in the media containing fluorophore-conjugated anti-CD107a antibody, brefeldin-A, and monensin. Following culture, NK cells were assayed by flow cytometry using fluorophore-conjugated antibodies against CD3, CD56 and IFN-gamma. CD107a and IFN-gamma staining were analyzed in $CD3^-CD56^+$ cells to assess NK cell activation. The increase in CD107a/IFN-gamma double-positive cells is indicative of better NK cell activation through engagement of two activating receptors rather than one receptor. NKG2D-binding domains and the positive control (selected from SEQ ID NO:45-48) showed a higher percentage of NK cells becoming $CD107a^+$ and IFN-$gamma^+$ than the isotype control (FIG. 24 & FIG. 25 represent data from two independent experiments, each using a different donor's PBMC for NK cell preparation).

Primary Mouse NK Cells

Figure 26:
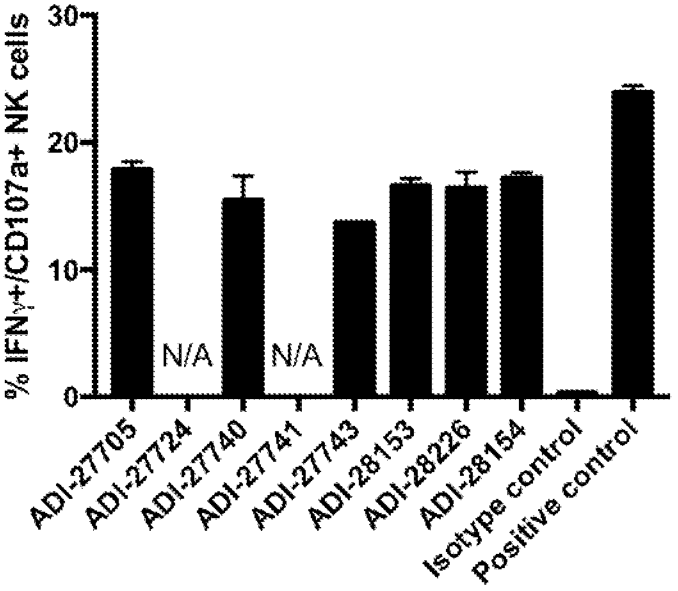
FIG. 26 are bar graphs showing activation of mouse NK cells by NKG2D-binding domains (listed as clones).
Figure 27:
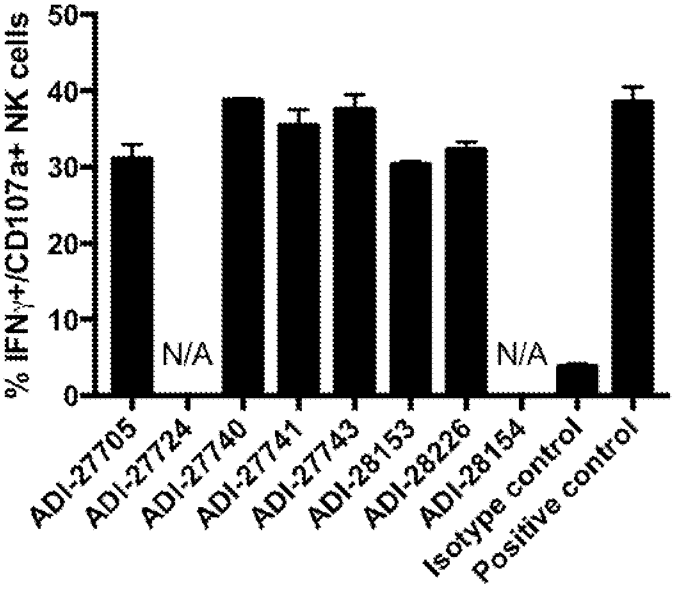
FIG. 27 are bar graphs showing activation of mouse NK cells by NKG2D-binding domains (listed as clones).

Spleens were obtained from C57Bl/6 mice and crushed through a 70 am cell strainer to obtain single cell suspension. Cells were pelleted and resuspended in ACK lysis buffer (purchased from Thermo Fisher Scientific #A1049201; 155 mM ammonium chloride, 10 mM potassium bicarbonate, 0.01 mM EDTA) to remove red blood cells. The remaining cells were cultured with 100 ng/mL hIL-2 for 72 hours before being harvested and prepared for NK cell isolation. NK cells ($CD3^-NK1.1^+$) were then isolated from spleen cells using a negative depletion technique with magnetic beads with typically >90% purity. Purified NK cells were cultured in media containing 100 ng/mL mIL-15 for 48 hours before they were transferred to the wells of a microplate to which the NKG2D-binding domains were adsorbed, and cultured in the media containing fluorophore-conjugated anti-CD107a antibody, brefeldin-A, and monensin. Following culture in NKG2D-binding domain-coated wells, NK cells were assayed by flow cytometry using fluorophore-conjugated antibodies against CD3, NK1.1 and IFN-gamma. CD107a and IFN-gamma staining were analyzed in $CD3^-$ $NK1.1^+$ cells to assess NK cell activation. The increase in CD107a/IFN-gamma double-positive cells is indicative of better NK cell activation through engagement of two activating receptors rather than one receptor. NKG2D-binding domains and the positive control (selected from anti-mouse NKG2D clones MI-6 and CX-5 available at eBioscience) showed a higher percentage of NK cells becoming $CD107a^+$ and IFN-gamma$^+$ than the isotype control (FIG. 26 & FIG. 27 represent data from two independent experiments, each using a different mouse for NK cell preparation).

Example 5—NKG2D-Binding Domains Enable Cytotoxicity of Target Tumor Cells

Human and mouse primary NK cell activation assays demonstrate increased cytotoxicity markers on NK cells after incubation with NKG2D-binding domains. To address whether this translates into increased tumor cell lysis, a cell-based assay was utilized where each NKG2D-binding domain was developed into a monospecific antibody. The Fc region was used as one targeting arm, while the Fab region (NKG2D-binding domain) acted as another targeting arm to activate NK cells. THP-1 cells, which are of human origin and express high levels of Fc receptors, were used as a tumor target and a Perkin Elmer DELFIA Cytotoxicity Kit was used. THP-1 cells were labeled with BATDA reagent, and resuspended at $10^5$/mL in culture media. Labeled THP-1 cells were then combined with NKG2D antibodies and isolated mouse NK cells in wells of a microtiter plate at 37° C. for 3 hours. After incubation, 20 μl of the culture supernatant was removed, mixed with 200 μl of Europium solution and incubated with shaking for 15 minutes in the dark. Fluorescence was measured over time by a PheraStar plate reader equipped with a time-resolved fluorescence module (Excitation 337 nm, Emission 620 nm) and specific lysis was calculated according to the kit instructions.

Figure 28:
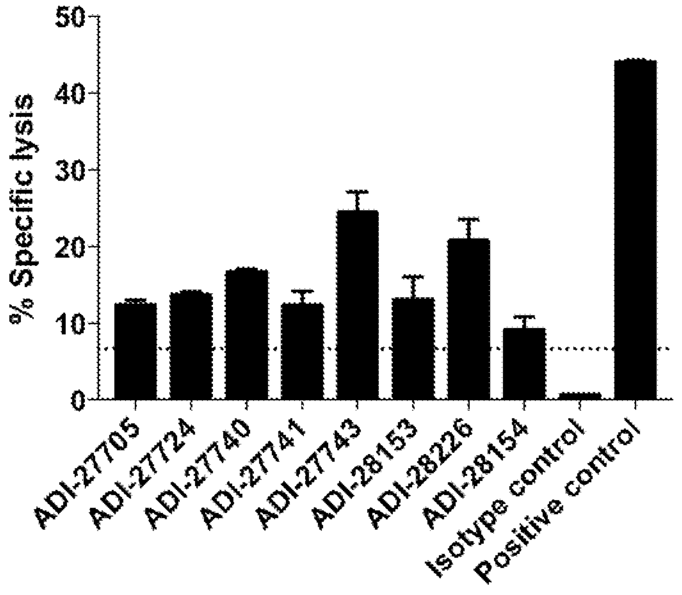
FIG. 28 are bar graphs showing the cytotoxic effect of NKG2D-binding domains (listed as clones) on tumor cells.

The positive control, ULBP-6—a natural ligand for NKG2D, showed increased specific lysis of THP-1 target cells by mouse NK cells. NKG2D antibodies also increased specific lysis of THP-1 target cells, while isotype control antibody showed reduced specific lysis. The dotted line indicates specific lysis of THP-1 cells by mouse NK cells without antibody added (FIG. 28).

Example 6—NKG2D Antibodies Show High Thermostability

Figure 29:
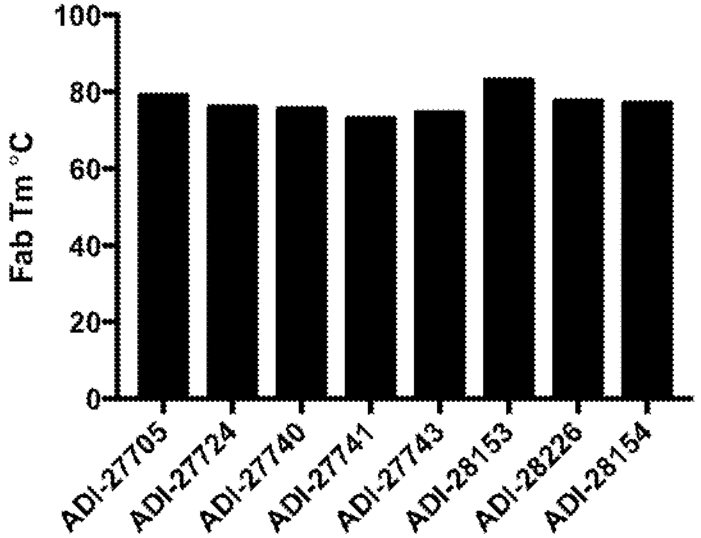
FIG. 29 are bar graphs showing the melting temperature of NKG2D-binding domains (listed as clones) measured by differential scanning fluorimetry.
Figure 30:
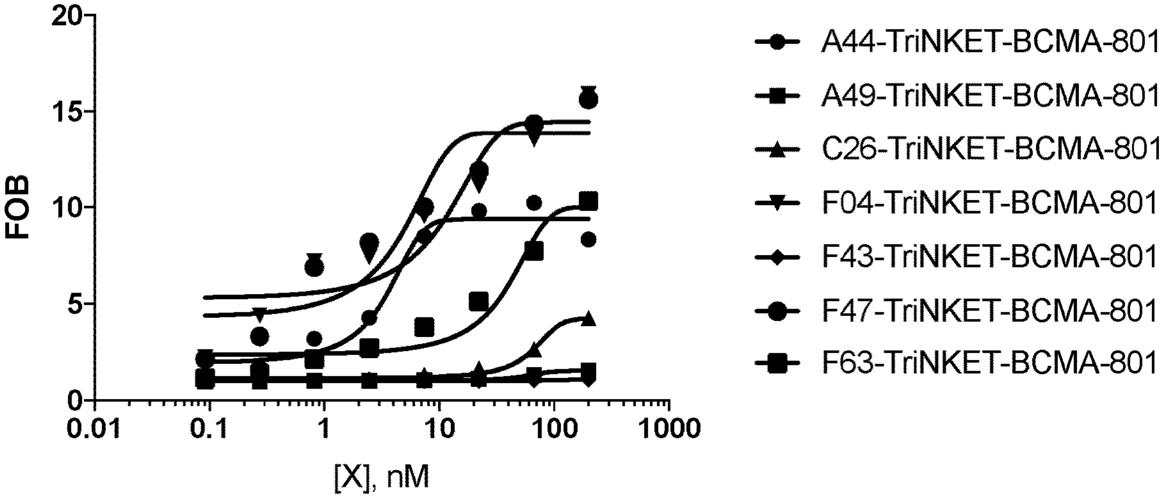
FIG. 30 are line graphs showing binding profile of BCMA-targeting TriNKETs to NKG2D expressed on EL4 cells.

Melting temperatures of NKG2D-binding domains were assayed using differential scanning fluorimetry. The extrapolated apparent melting temperatures are high relative to typical IgG1 antibodies (FIG. 29).

Example 7—Multi-Specific Binding Proteins Bind to NKG2D

EL4 mouse lymphoma cell lines were engineered to express human NKG2D. Trispecific binding proteins (TriNKETs) that each contain an NKG2D-binding domain, a tumor-associated antigen-binding domain (BCMA-binding domain), and an Fc domain that binds to CD16 as shown in FIG. 1, were tested for their affinity to extracellular NKG2D expressed on EL4 cells. The binding of the multi-specific binding proteins to NKG2D was detected using fluorophore-conjugated anti-human IgG secondary antibodies. Cells were analyzed by flow cytometry, and fold-over-background (FOB) was calculated using the mean fluorescence intensity (MFI) of NKG2D-expressing cells compared to parental EL4 cells.

TriNKETs tested include BCMA-TriNKET-C26 (ADI-28226 and a BCMA-binding domain), BCMA-TriNKET-F04 (ADI-29404 and a BCMA-binding domain), BCMA-TriNKET-F43 (ADI-29443 and a BCMA-binding domain), and BCMA-TriNKET-F47 (ADI-29447 and a BCMA-binding domain).

The BCMA-binding domain used in the tested molecules was composed of a heavy chain variable domain and light chain variable domain as listed below.

```
EM-801 heavy chain variable domain (SEQ ID NO: 91):
EVQLLESGGGLVQPGGSLRLSCAASGFTFSSYAMSWVRQAPGKGLEWVSAISGSGG
                              -----              ------
                              CDR1                 CDR2

STYYADSVKGRFTISRDNSKNTLYLQMNSLRAEDTAVYYCAKVLGWFDYWGQGTLVTVSS
----------                                -------
                                            CDR3

EM-801 light chain variable domain (SEQ ID NO: 92):
EIVLTQSPGTLSLSPGERATLSCRASQSVSSSYLAWYQQKPGQAPRLLIYGASSRATGI
                       ------------               -------
                          CDR1                      CDR2

PDRFSGSGSGTDFTLTISRLEPEDFAVYYCQQYGYPPDFTFGQGTKVEIK
                              ----------
                                 CDR3

EM-901 heavy chain variable domain (SEQ ID NO: 93)
EVQLLESGGGLVQPGGSLRLSCAASGFTFSDNAMGWVRQAPGKGLEWVSAISGPGSST
                         ----------              --------
                            CDR1                   CDR2

YYADSVKGRFTISRDNSKNTLYLQMNSLRAEDTAVYYCAKVLGWFDYWGQGTLVT
--------                                -------
                                          CDR3
```

-continued

EM-901 light chain variable domain (SEQ ID NO: 94)

```
EIVLTQSPGTLSLSPGERATLSCRASQSVSDEYLSWYQQKPGQAPRLLIHSASTRATGIPD
                       CDR1                        CDR2

RFSGSGSGTDFTLAISRLEPEDFAVYYCQQYGYPPDFTFGQGTKVEIK
                            CDR3
```

Example 8—Multi-Specific Binding Proteins Bind to Human Tumor Antigens

Trispecific Binding Proteins Bind to BCMA

Figure 31:
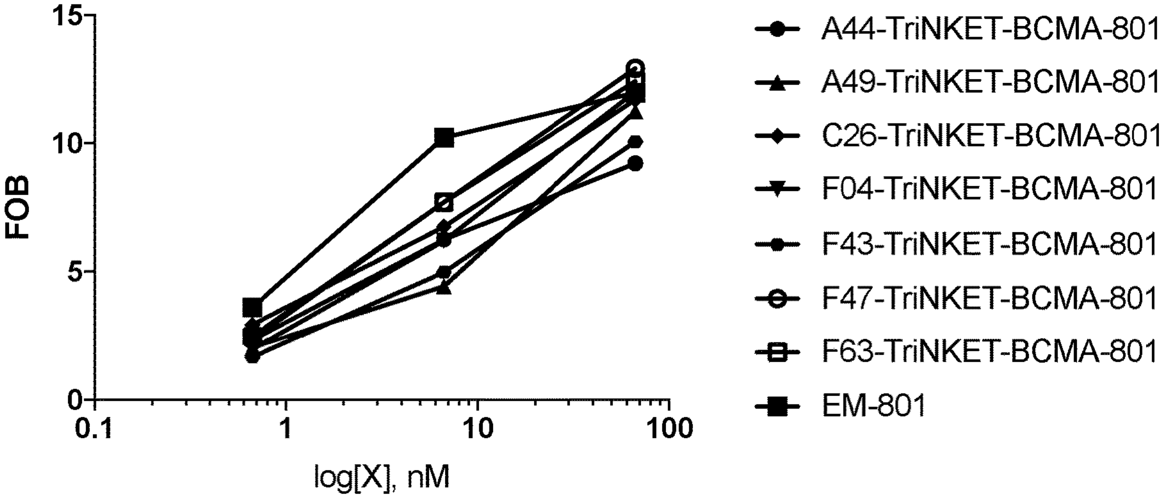
FIG. 31 are line graphs showing binding profile of BCMA-targeting TriNKETs to BCMA expressed on MM.1S human myeloma cells.

MM.1S human myeloma cells expressing BCMA were used to assay the binding of TriNKETs to the tumor associated antigen BCMA. TriNKETs were diluted, and were incubated with the respective cells. TriNKETs and optionally the parental anti-BCMA monoclonal antibody (EM-801) were incubated with the cells, and the binding was detected using fluorophore-conjugated anti-human IgG secondary antibodies. Cells were analyzed by flow cytometry, and fold-over-background (FOB) was calculated using the mean fluorescence intensity (MFI) from TriNKETs and EM-801 normalized to secondary antibody controls. C26-TriNKET-BCMA, F04-TriNKET-BCMA, F43-TriNKET-BCMA, and F47-TriNKET-BCMA show comparable levels of binding to BCMA expressed on MM.1S cells as compared with EM-801 (FIG. 31).

Example 9—Multi-Specific Binding Proteins Activate NK Cells

Figure 32:
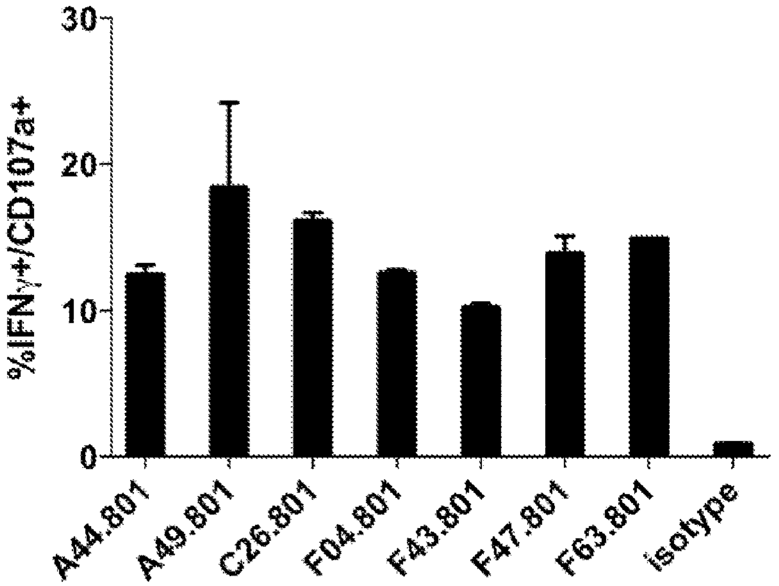
FIG. 32 are bar graphs showing human NK activation in culture with BCMA-positive MM.1S human myeloma cells.

Primary Human NK Cells are Activated by TriNKETs in Co-Culture with Target Expressing Human Cancer Cell Lines Co-culturing primary human NK cells with BCMA-positive MM.1S myeloma cells resulted in TriNKET-mediated activation of the primary human NK cells. TriNKETs targeting BCMA (e.g., C26-TriNKET-BCMA and F04-TriNKET-BCMA) mediated activation of human NK cells co-cultured with MM.1S myeloma cells, as indicated by an increase in CD107a degranulation and IFNγ cytokine production (FIG. 32). Compared to isotype TriNKET, TriNKETs targeting BCMA (e.g., A44-TriNKET-BCMA, A49-TriNKET-BCMA, C26-TriNKET-BCMA, F04-TriNKET-BCMA, F43-TriNKET-BCMA, F43-TriNKET-BCMA, F47-TriNKET-BMCA, and F63-TriNKET-BCMA) showed increased NK cell activity (FIG. 32).

Example 10—Trispecific Binding Proteins Enable Cytotoxicity of Target Cancer Cells Peripheral blood mononuclear cells (PBMCs) were isolated from human peripheral blood buffy coats using density gradient centrifugation. NK cells ($CD3^{-}CD56^{+}$) were isolated using negative selection with magnetic beads from PBMCs, and the purity of the isolated NK cells was typically >90%. Isolated NK cells were cultured in media containing 100 ng/mL IL-2 for activation or rested overnight without cytokine. IL-2-activated or rested NK cells were used the following day in cytotoxicity assays.

DELFIA Cytotoxicity Assay:

Human cancer cell lines expressing a target of interest were harvested from culture, cells were washed with PBS, and were resuspended in growth media at $10^6$/mL for labeling with BATDA reagent (Perkin Elmer AD0116). Manufacturer instructions were followed for labeling of the target cells. After labeling cells were washed 3× with PBS, and were resuspended at 0.5-1.0×$10^5$/mL in culture media. To prepare the background wells an aliquot of the labeled cells was put aside, and the cells were spun out of the media. 100 μl of the media was carefully added to wells in triplicate to avoid disturbing the pelleted cells. 100 μl of BATDA labeled cells were added to each well of the 96-well plate. Wells were saved for spontaneous release from target cells, and wells were prepared for max lysis of target cells by addition of 1% Triton-X. Monoclonal antibodies or TriNKETs against the tumor target of interest were diluted in culture media, 50 μl of diluted mAb or TriNKET was added to each well. Rested and/or activated NK cells were harvested from culture, cells were washed, and were resuspended at 10-2.0×$10^6$/mL in culture media depending on the desired E:T ratio. 50 μl of NK cells was added to each well of the plate to make a total of 200 μl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 μl of culture supernatant was transferred to a clean microplate provided from the manufacturer and 200 μl of room temperature europium solution was added to each well. The plate was protected from the light and incubated on a plate shaker at 250 rpm for 15 minutes. The plate was read using either Victor 3 or SpectraMax i3X instruments. % Specific lysis was calculated as follows: % Specific lysis=((Experimental release−Spontaneous release)/(Maximum release−Spontaneous release))*100%.

Figure 39:
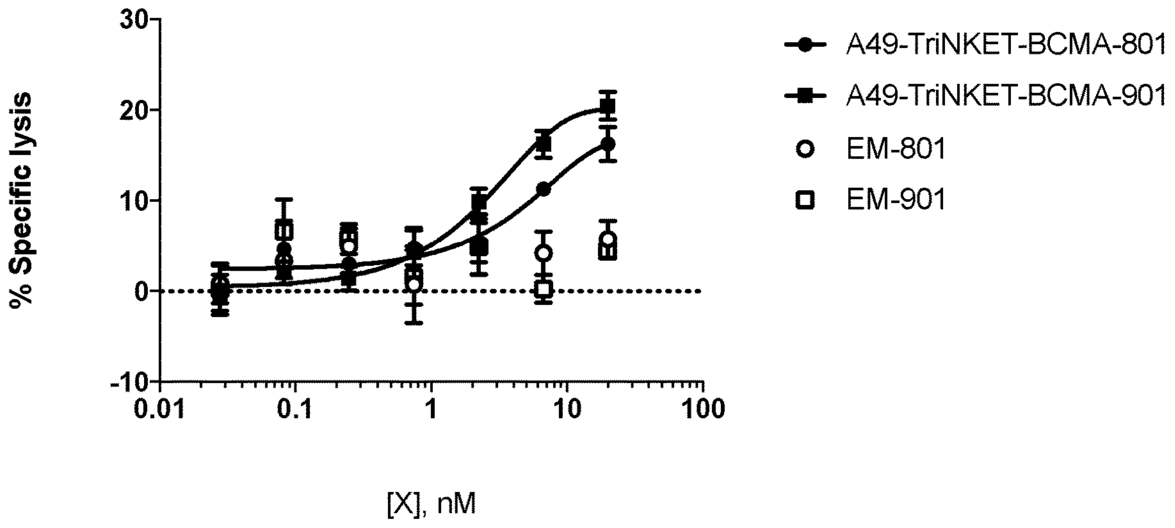
FIG. 39 is a graph showing that TriNKETs enhance human NK cell lysis of KMS12-PE myeloma cells.

TriNKET-mediated lysis of BCMA-positive myeloma cells was assayed. FIG. 39 shows TriNKET-mediated lysis of BCMA-positive KMS12-PE myeloma cells by rested human NK effector cells. Two TriNKETs (cFAE-A49.801 and cFAE-A49.901) using the same NKG2D-binding domain (A49), but different BCMA targeting domains were tested for efficacy in vitro. Both TriNKETs enhanced NK cell lysis of KMS12-PE cells to a similar extent, but TriNKETs using the EM-901 targeting domain provided increased potency (FIG. 39).

Figure 33:
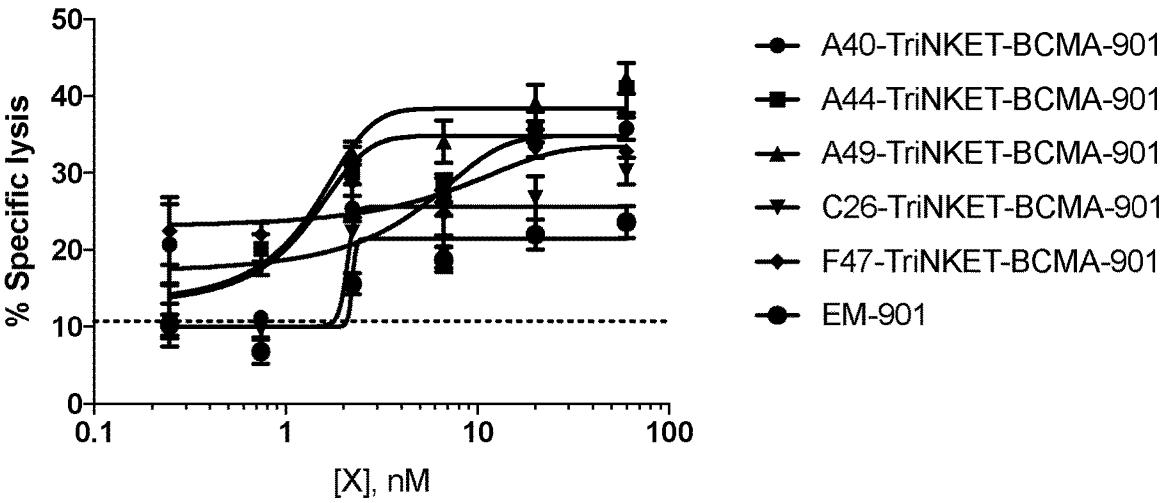
FIG. 33 are line graphs showing that BCMA targeting TriNKETs with different NKG2D-binding domains enhance human NK cell lysis of KMS12-PE myeloma cells.

FIG. 33 shows cytotoxic activity of several TriNKETs using different NKG2D-binding domains (A40, A44, A49, C26, and F47), but the same BCMA targeting domain. Changing the NKG2D-binding domain of the BCMA-targeted TriNKET produced variations in maximal killing as well as potency of the TriNKETs. All TriNKETs demonstrated increased killing of KMS12-PE target cells compared to EM-901 monoclonal antibody (FIG. 33).

Example 11

Synergistic activation of human NK cells by cross-linking NKG2D and CD16 was investigated.

Primary Human NK Cell Activation Assay

Peripheral blood mononuclear cells (PBMCs) were isolated from peripheral human blood buffy coats using density gradient centrifugation. NK cells were purified from PBMCs using negative magnetic beads (StemCell #17955). NK cells were >90% $CD3\text{-}CD56^{+}$ as determined by flow cytometry.

Cells were then expanded 48 hours in media containing 100 ng/mL hIL-2 (Peprotech #200-02) before use in activation assays. Antibodies were coated onto a 96-well flat-bottom plate at a concentration of 2 μg/ml (anti-CD16, Biolegend #302013) and 5 jag/mL (anti-NKG2D, R&D #MAB 139) in 100 μl sterile PBS overnight at 4° C. followed by washing the wells thoroughly to remove excess antibody. For the assessment of degranulation IL-2-activated NK cells were resuspended at $5\times10^5$ cells/ml in culture media supplemented with 100 ng/mL hIL2 and 1 μg/mL APC-conjugated anti-CD107a mAb (Biolegend #328619). $1\times10^5$ cells/well were then added onto antibody coated plates. The protein transport inhibitors Brefeldin A (BFA, Biolegend #420601) and Monensin (Biolegend #420701) were added at a final dilution of 1:1000 and 1:270 respectively. Plated cells were incubated for 4 hours at 37° C. in 5% $CO_2$. For intracellular staining of IFN-γ NK cells were labeled with anti-CD3 (Biolegend #300452) and anti-CD56 mAb (Biolegend #318328) and subsequently fixed and permeabilized and labeled with anti-IFN-γ mAb (Biolegend #506507). NK cells were analyzed for expression of CD107a and IFN-γ by flow cytometry after gating on live CD56+CD3-cells.

Figure 3:
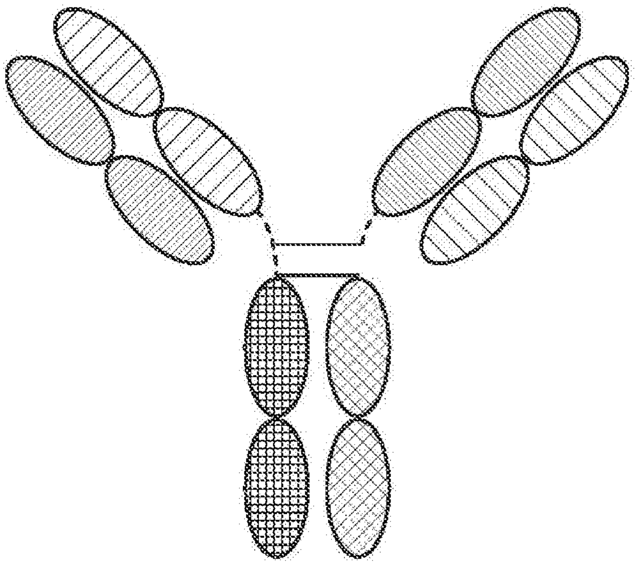
FIG. 3 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be an heterodimeric construct containing ½ of rat antibody and ½ of mouse antibody.
Figure 4:
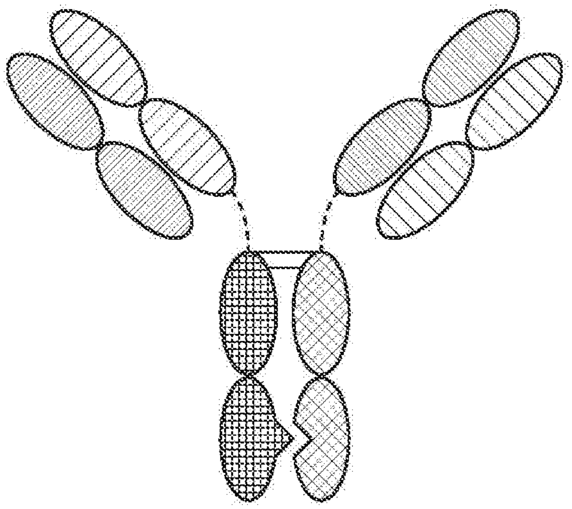
FIG. 4 is a representation of a TriNKET in the KiH Common Light Chain (LC) form, which involves the knobs-into-holes (KIHs) technology. KiH is a heterodimer containing 2 Fabs binding to target 1 and 2, and an $F_C$ stabilized by heterodimerization mutations. TriNKET in the KiH format may be an heterodimeric construct with 2 fabs binding to target 1 and target 2, containing two different heavy chains and a common light chain that pairs with both heavy chains.
Figure 5:
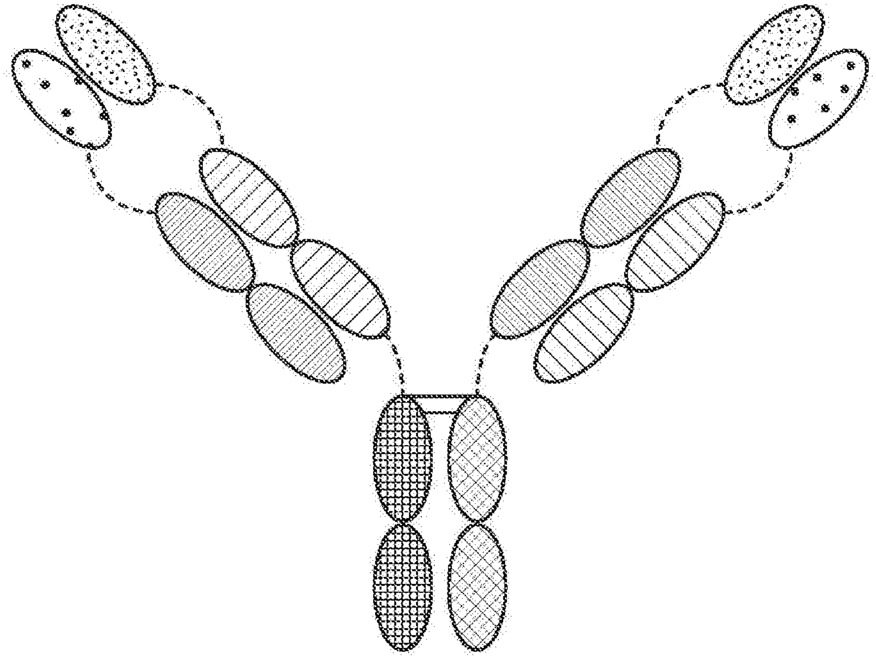
FIG. 5 is a representation of a TriNKET in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is an homodimeric construct where variable domain targeting antigen 2 is fused to the N terminus of variable domain of Fab targeting antigen 1 Construct contains normal Fc.
Figure 6:
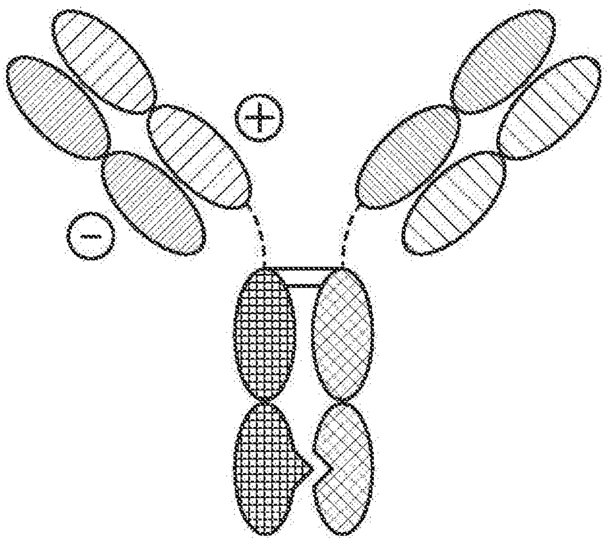
FIG. 6 is a representation of a TriNKET in the Orthogonal Fab interface (Ortho-Fab) form, which is an heterodimeric construct that contains 2 Fabs binding to target1 and target 2 fused to Fc. LC-HC pairing is ensured by orthogonal interface. Heterodimerization is ensured by mutations in the $F_C$.
Figure 7:
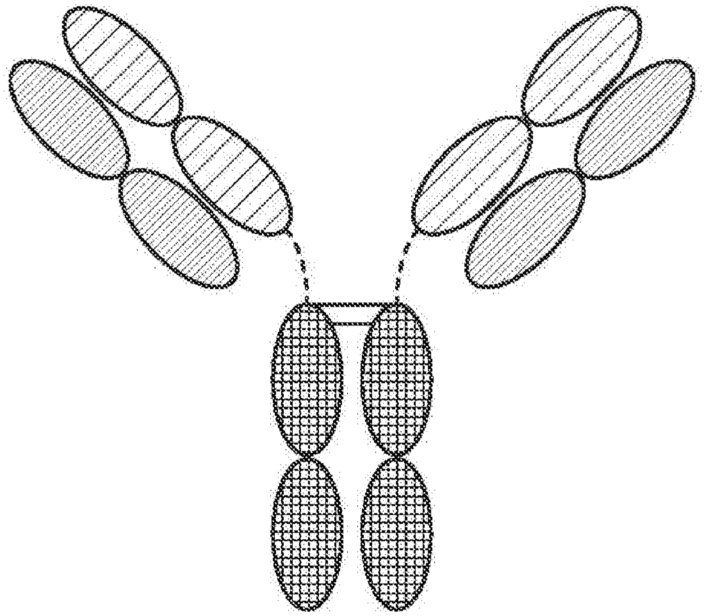
FIG. 7 is a representation of a TrinKET in the 2 in-1 Ig format.
Figure 8:
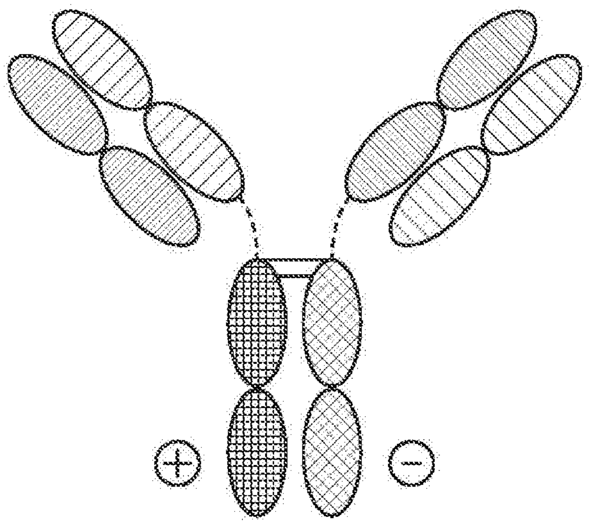
FIG. 8 is a representation of a TriNKET in the ES form, which is an heterodimeric construct containing two different Fabs binding to target 1 and target 2 fused to the $F_C$. Heterodimerization is ensured by electrostatic steering mutations in the Fc.
Figure 9:
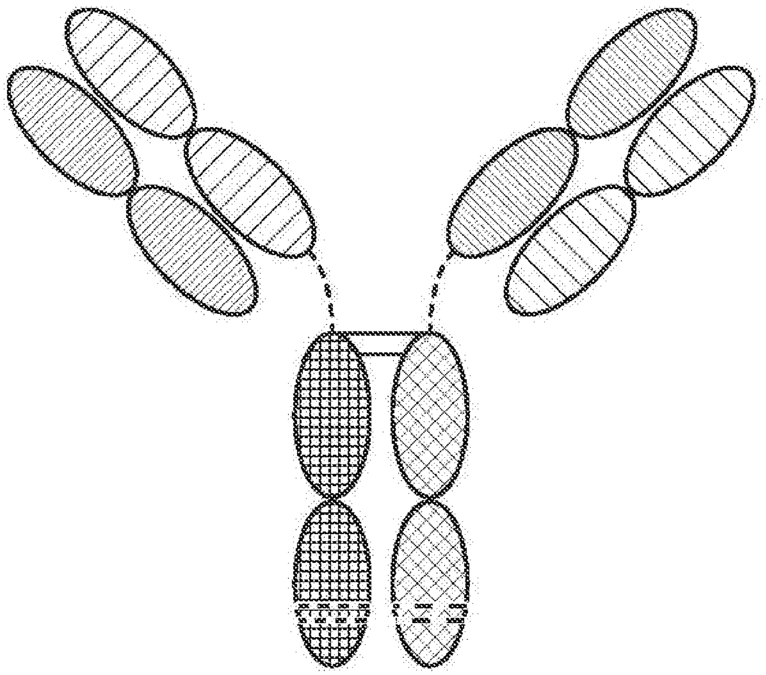
FIG. 9 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an $F_C$ stabilized by heterodimerization mutations.
Figure 10:
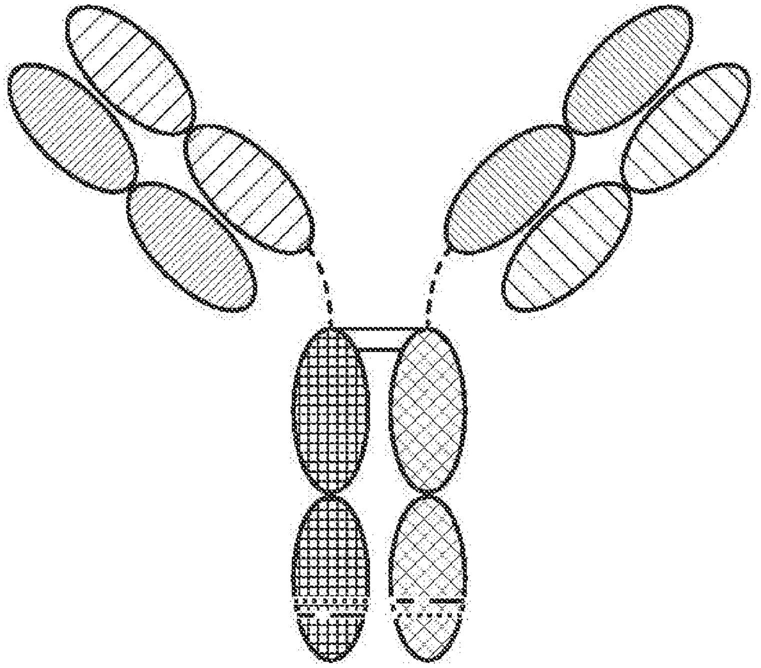
FIG. 10 is a representation of a TriNKET in the SEED Body form, which is an heterodimer containing 2 Fabs binding to target 1 and 2, and an $F_C$ stabilized by heterodimerization mutations.
Figure 11:
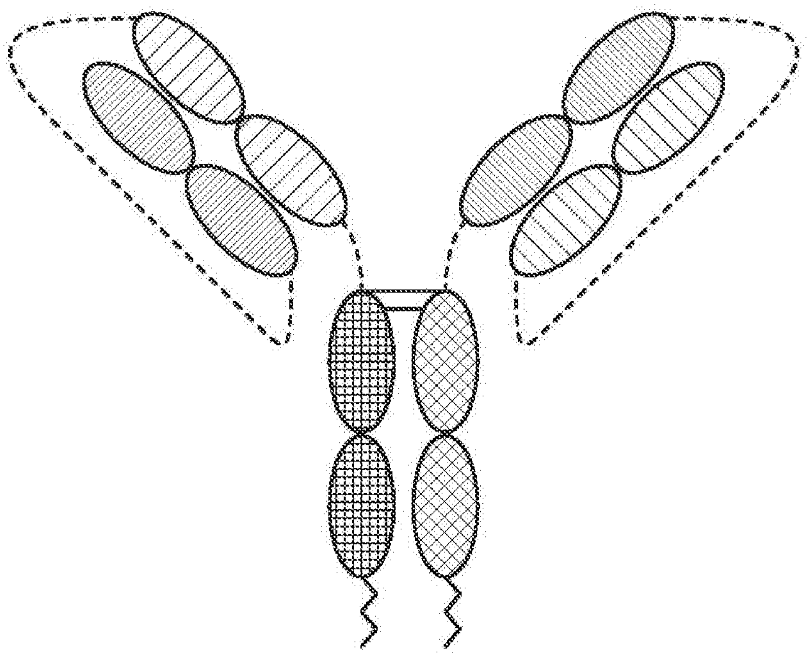
FIG. 11 is a representation of a TriNKET in the LuZ-Y form, in which leucine zipper is used to induce heterodimerization of two different HCs. LuZ-Y form is a heterodimer containing two different scFabs binding to target 1 and 2, fused to $F_C$. Heterodimerization is ensured through leucine zipper motifs fused to C-terminus of $F_C$.
Figure 12:
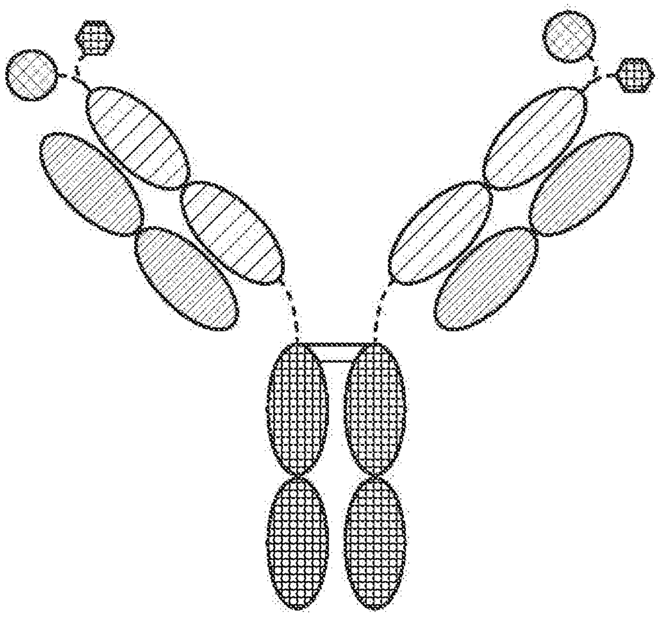
FIG. 12 is a representation of a TriNKET in the Cov-X-Body form.
Figure 34A:
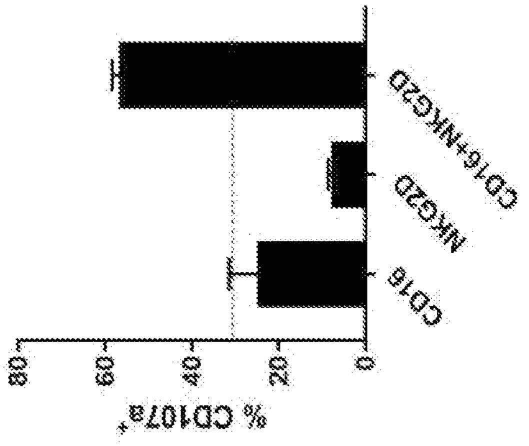
FIGS. 34A-34C are bar graphs of synergistic activation of NK cells using CD16 and NKG2D.
Figure 34B:
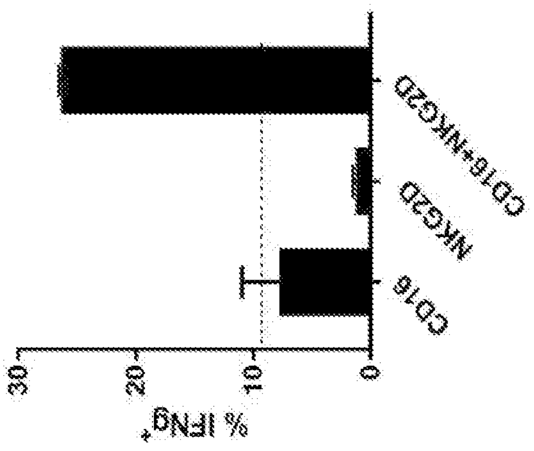

To investigate the relative potency of receptor combination, crosslinking of NKG2D or CD16 and co-crosslinking of both receptors by plate-bound stimulation was performed. As shown in FIG. 34 (FIGS. 34A-3C), combined stimulation of CD16 and NKG2D resulted in highly elevated levels of CD107a (degranulation) (FIG. 3A) and/or IFN-γ production (FIG. 34B). Dotted lines represent an additive effect of individual stimulations of each receptor.

Figure 34C:
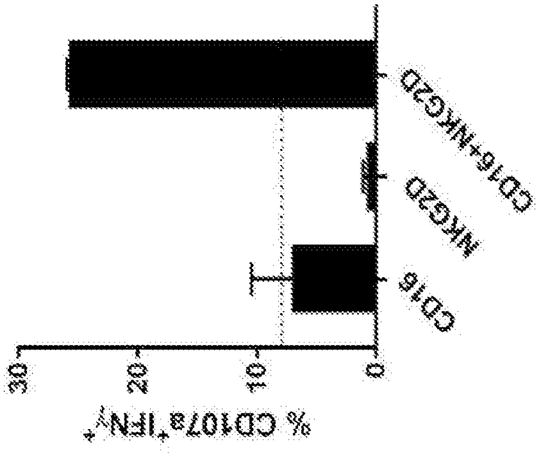
Figure 35:
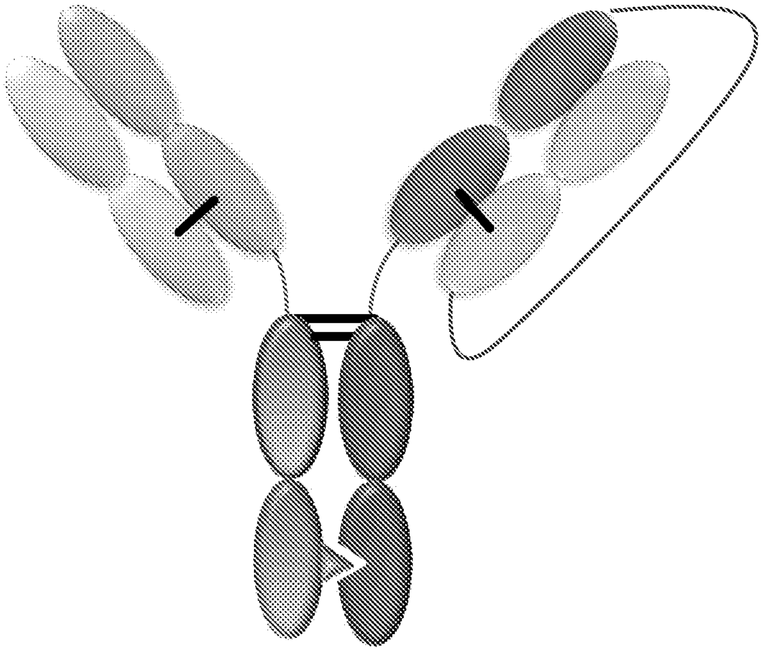
FIG. 35 is an Oasc-Fab heterodimeric construct that includes Fab binding to target 1 and scFab binding to target 2 fused to Fc. Heterodimerization is ensured by mutations in the $F_C$.
Figure 36:
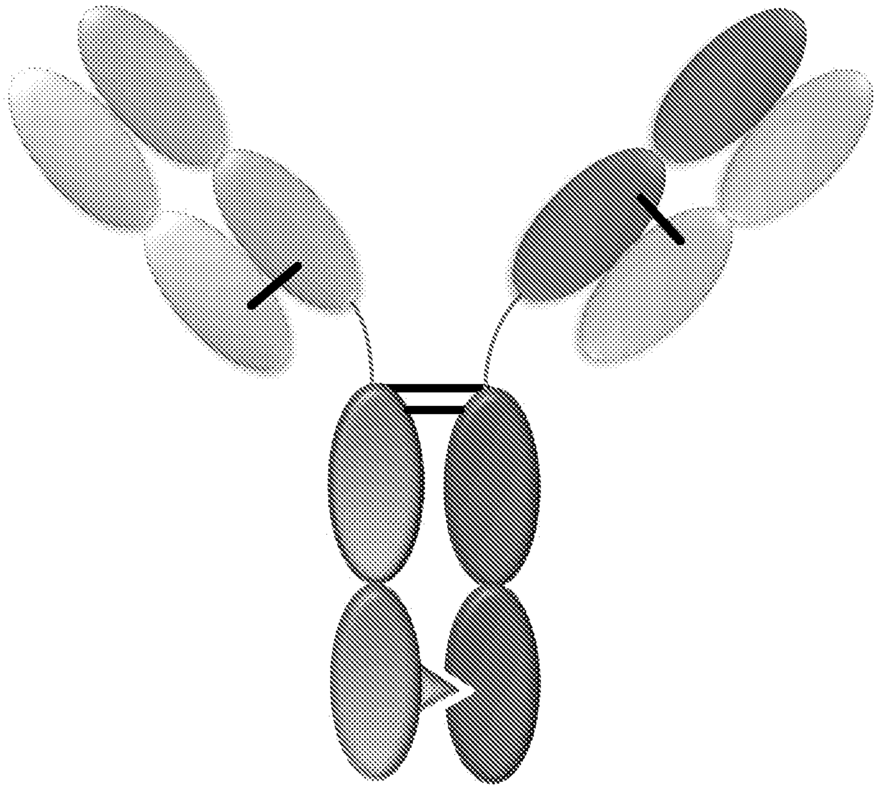
FIG. 36 is a DuetMab, which is an heterodimeric construct containing two different Fabs binding to antigens 1 and 2, and $F_C$ stabilized by heterodimerization mutations. Fab 1 and 2 contain differential S—S bridges that ensure correct light chain (LC) and heavy chain (HC) pairing.
Figure 37:
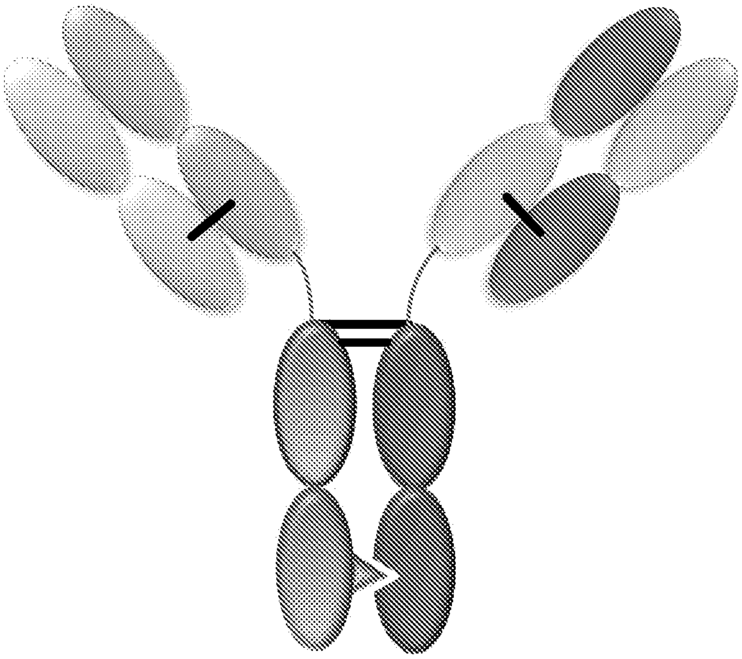
FIG. 37 is a CrossmAb, which is an heterodimeric construct with two different Fabs binding to targets 1 and 2 fused to Fc stabilized by heterodimerization. CL and CH1 domains and VH and VL domains are switched, e.g., CH1 is fused in-line with VL, while CL is fused in-line with VH.
Figure 38:
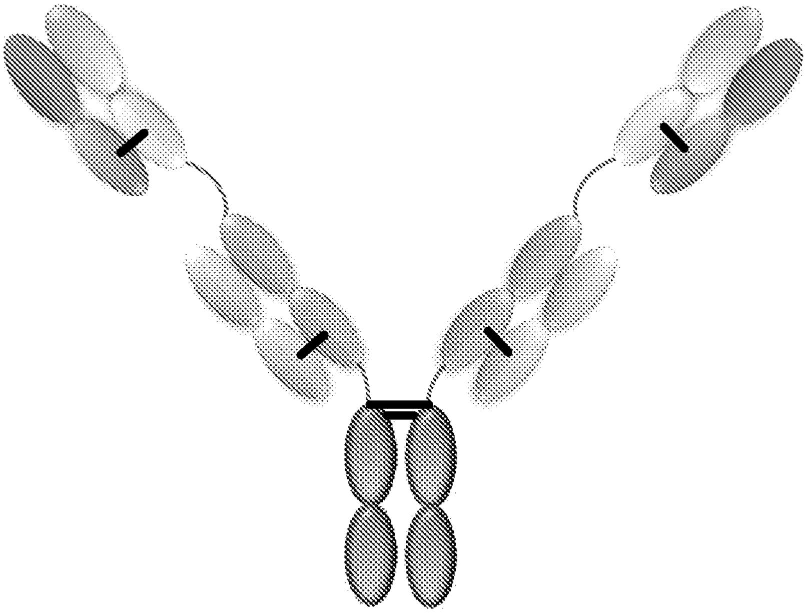
FIG. 38 is a Fit-Ig, which is an homodimeric constructs where Fab binding to antigen 2 is fused to the N terminus of HC of Fab that binds to antigen 1. The construct contains wild-type Fc.

CD107a levels and intracellular IFN-γ production of IL-2-activated NK cells were analyzed after 4 hours of plate-bound stimulation with anti-CD16, anti-NKG2D or a combination of both monoclonal antibodies. Graphs indicate the mean (n=2)±SD. FIG. 34A demonstrates levels of CD107a; FIG. 34B demonstrates levels of IFNγ; FIG. 34C demonstrates levels of CD107a. Data shown in FIGS. 34A-34C are representative of five independent experiments using five different healthy donors.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A multi-specific binding protein comprising:

(a) a first antigen-binding site that binds and activates human NKG2D;

(b) a second antigen-binding site that binds BCMA; and (c) a first antibody Fc domain of human IgG1 and a second antibody Fc domain of human IgG1 that together are sufficient to bind CD16, wherein the first and second antibody Fc domains comprise different amino acid mutations to promote heterodimerization, and the first and second antibody Fc domains each comprise an N-terminus;

wherein the first antigen-binding site is linked to the N-terminus of the first antibody Fc domain, and the second antigen-binding site is linked to the N-terminus of the second antibody Fc domain;

wherein each of the first and second human IgG1 antibody Fc domains comprises hinge and CH2 domains, and wherein the first antigen-binding site comprises a heavy chain variable domain and a light chain variable domain, and wherein the heavy chain variable domain and the light chain variable domain are present on the same polypeptide.

2. The multi-specific binding protein of claim 1, wherein the first antigen-binding site comprises a heavy chain CDR1 sequence identical to the amino acid sequence of SEQ ID NO:64; a heavy chain CDR2 sequence identical to the amino acid sequence of SEQ ID NO:65; and a heavy chain CDR3 sequence identical to the amino acid sequence of SEQ ID NO:66; the light chain CDR1, CDR2, and CDR3 sequences by Kabat numbering of a light chain variable domain comprising the amino acid sequence of SEQ ID NO:2, SEQ ID NO: 4, SEQ ID NO:6, SEQ ID NO:8, SEQ ID NO: 10, SEQ ID NO: 14, SEQ ID NO: 16, SEQ ID NO: 18, SEQ ID NO:20, SEQ ID NO:22, SEQ ID NO:24, SEQ ID NO:26, SEQ ID NO:28, SEQ ID NO: 30, SEQ ID NO:32, SEQ ID NO:34, SEQ ID NO:36, SEQ ID NO:38, SEQ ID NO:40, or SEQ ID NO:96.

3. The multi-specific binding protein according to claim 1, wherein the first antigen-binding site comprises:

(i) a heavy chain CDR1 sequence identical to the amino acid sequence of SEQ ID NO: 67; a heavy chain CDR2 sequence identical to the amino acid sequence of SEQ ID NO:68; a heavy chain CDR3 sequence identical to the amino acid sequence of SEQ ID NO:69; a light chain CDR1 sequence identical to the amino acid sequence of SEQ ID NO:70; a light chain CDR2 sequence identical to the amino acid sequence of SEQ ID NO:71; and a light chain CDR3 sequence identical to the amino acid sequence of SEQ ID NO:72;

(ii) a heavy chain CDR1 sequence identical to the amino acid sequence of SEQ ID NO: 73; a heavy chain CDR2 sequence identical to the amino acid sequence of SEQ ID NO:74; a heavy chain CDR3 sequence identical to the amino acid sequence of SEQ ID NO:75; a light chain CDR1 sequence identical to the amino acid sequence of SEQ ID NO:76; a light chain CDR2 sequence identical to the amino acid sequence of SEQ ID NO:77; and a light chain CDR3 sequence identical to the amino acid sequence of SEQ ID NO:78;

(iii) a heavy chain CDR1, CDR2, and CDR3 identical to the CDR1, CDR2, and CDR3 amino acid sequences of SEQ ID NO:45 and a light chain CDR1, CDR2, and CDR3 identical to the CDR1, CDR2, and CDR3 amino acid sequences of SEQ ID NO:46; or (iv) a heavy chain CDR1, CDR2, and CDR3 identical to the CDR1, CDR2, and CDR3 amino acid sequences of SEQ ID NO:47 and a light chain CDR1, CDR2, and CDR3 identical to the CDR1, CDR2, and CDR3 amino acid sequences of SEQ ID NO:48.

4. The multi-specific binding protein according to claim 2, wherein the first antigen-binding site comprises a heavy chain variable domain at least 95% identical to SEQ ID NO: 1 and a light chain variable domain at least 95% identical to SEQ ID NO:2, SEQ ID NO: 4, SEQ ID NO:6, SEQ ID NO:8, SEQ ID NO: 10, SEQ ID NO:14, SEQ ID NO: 16, SEQ ID NO: 18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO: 40, or SEQ ID NO:96.

5. The multi-specific binding protein according to claim 3, wherein the first antigen-binding site comprises (i) a heavy chain variable domain at least 95% identical to SEQ ID NO:41 and a light chain variable domain at least 95% identical to SEQ ID NO:42;

(ii) a heavy chain variable domain at least 95% identical to SEQ ID NO:43 and a light chain variable domain at least 95% identical to SEQ ID NO:44;

(iii) a heavy chain variable domain at least 95% identical to SEQ ID NO:45 and a light chain variable domain at least 95% identical to SEQ ID NO:46;

(iv) a heavy chain variable domain at least 95% identical to SEQ ID NO:47 and a light chain variable domain at least 95% identical to SEQ ID NO:48.

6. The multi-specific binding protein according to claim 1, wherein the first antigen-binding site comprises:

(i) a heavy chain variable domain identical to SEQ ID NO:41 and a light chain variable domain identical to SEQ ID NO:42;

(ii) a heavy chain variable domain identical to SEQ ID NO:43 and a light chain variable domain identical to SEQ ID NO:44;

(iii) a heavy chain variable domain identical to SEQ ID NO:45 and a light chain variable domain identical to SEQ ID NO:46;

(iv) a heavy chain variable domain identical to SEQ ID NO:47 and a light chain variable domain identical to SEQ ID NO:48; or (v) a heavy chain variable domain identical to SEQ ID NO: 1 and a light chain variable domain identical to SEQ ID NO:2, SEQ ID NO:4, SEQ ID NO:6, SEQ ID NO:8, SEQ ID NO: 10, SEQ ID NO: 14, SEQ ID NO: 16, SEQ ID NO: 18, SEQ ID NO:20, SEQ ID NO:22, SEQ ID NO: 24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, or SEQ ID NO:96.

7. The multi-specific binding protein according to claim 1, wherein the second antigen-binding site comprises a heavy chain variable domain and a light chain variable domain.

8. The multi-specific binding protein according to claim 7, wherein the heavy chain variable domain and the light chain variable domain of the second antigen-binding site are present on the same polypeptide.

9. The multi-specific binding protein according to claim 1, wherein the second antigen-binding site comprises:

(i) a heavy chain CDR1 sequence identical to the amino acid sequence of SEQ ID NO: 50; a heavy chain CDR2 sequence identical to the amino acid sequence of SEQ ID NO:51; a heavy chain CDR3 sequence identical to the amino acid sequence of ID NO: 52; a light chain CDR1 sequence identical to the amino acid sequence of SEQ ID NO:55; a light chain CDR2 sequence identical to the amino acid sequence of SEQ ID NO:56; and a light chain CDR3 sequence identical to the amino acid sequence of SEQ ID NO: 57 or SEQ ID NO: 58;

(ii) a heavy chain CDR1 sequence identical to the amino acid sequence of SEQ ID NO: 79; a heavy chain CDR2 sequence identical to the amino acid sequence of SEQ ID NO: 80;

a heavy chain CDR3 sequence identical to the amino acid sequence of SEQ ID NO:81; a light chain CDR1 sequence identical to the amino acid sequence of SEQ ID NO:82; a light chain CDR2 sequence identical to the amino acid sequence of SEQ ID NO: 83; and a light chain CDR3 sequence identical to the amino acid sequence of SEQ ID NO:84;

(iii) a heavy chain CDR1 sequence identical to the amino acid sequence of SEQ ID NO: 85; a heavy chain CDR2 sequence identical to the amino acid sequence of SEQ ID NO: 86; a heavy chain CDR3 sequence identical to the amino acid sequence of SEQ ID NO:87; a light chain CDR1 sequence identical to the amino acid sequence of SEQ ID NO:88; a light chain CDR2 sequence identical to the amino acid sequence SEQ ID NO: 89; and a light chain CDR3 sequence identical to the amino acid sequence of SEQ ID NO:90; or (iv) a heavy chain CDR1 sequence identical to the amino acid sequence of SEQ ID NO: 137; a heavy chain CDR2 sequence identical to the amino acid sequence of SEQ ID NO: 138; a heavy chain CDR3 sequence identical to the amino acid of SEQ ID NO:139; a light chain CDR1 sequence identical to the amino acid sequence of SEQ ID NO:140; a light chain CDR2 sequence identical to the amino acid sequence of SEQ ID NO:141; and a light chain CDR3 sequence identical to the amino acid sequence of SEQ ID NO:142.

10. The multi-specific binding protein according to claim 9, wherein (i) the heavy chain variable domain of the second antigen-binding site comprises an amino acid sequence at least 95% identical to SEQ ID NO:49 and the light chain variable domain of the second antigen-binding site comprises an amino acid sequence at least 95% identical to SEQ ID NO: 53 or SEQ ID NO:54;

(ii) the heavy chain variable domain of the second antigen-binding site comprises an amino acid sequence at least 95% identical to SEQ ID NO: 59 and the light chain variable domain of the second antigen-binding site comprises an amino acid sequence at least 95% identical to SEQ ID NO:60;

(iii) the heavy chain variable domain of the second antigen-binding site comprises an amino acid sequence at least 95% identical to SEQ ID NO:61 and the light chain variable domain of the second antigen-binding site comprises an amino acid sequence at least 95% identical to SEQ ID NO:62; or (iv) the heavy chain variable domain of the second antigen-binding site comprises an amino acid sequence at least 95% identical to SEQ ID NO:91 and the light chain variable domain of the second antigen-binding site comprises an amino acid sequence at least 95% identical to SEQ ID NO:92.

11. The multi-specific binding protein according to claim 1, wherein (i) the heavy chain variable domain of the second antigen-binding site comprises an amino acid sequence identical to SEQ ID NO:49 and the light chain variable domain of the second antigen-binding site comprises an amino acid sequence identical to SEQ ID NO: 53 or SEQ ID NO:54;

(ii) the heavy chain variable domain of the second antigen-binding site comprises an amino acid sequence identical to SEQ ID NO:59 and the light chain variable domain of the second antigen-binding site comprises an amino acid sequence identical to SEQ ID NO:60;

(iii) the heavy chain variable domain of the second antigen-binding site comprises an amino acid sequence identical to SEQ ID NO:61 and the light chain variable domain of the second antigen-binding site comprises an amino acid sequence identical to SEQ ID NO:62; or (iv) the heavy chain variable domain of the second antigen-binding site comprises an amino acid sequence identical to SEQ ID NO:91 and the light chain variable domain of the second antigen-binding site comprises an amino acid sequence identical to SEQ ID NO:92.

12. The multi-specific binding protein according to claim 1, wherein each of the first and second human IgG1 antibody Fc domains comprises an amino acid sequence at least 90% identical to amino acids 234-332 of a human IgG1 antibody, numbered according to EU numbering.

13. The multi-specific binding protein according to claim 1, wherein each of the first and second human IgG1 antibody Fc domains comprises an amino acid sequence at least 90% identical to the Fc domain of human IgG1 and differs from said Fc domain of human IgG1 at one or more positions selected from the group consisting of Q347, Y349, L351, S354, E356, E357, K360, Q362, S364, T366, L368, K370, N390, K392, T394, D399, S400, D401, F405, Y407, K409, T411, and K439, numbered according to EU numbering.

14. The multi-specific binding protein of claim 13, wherein each of the first and second human IgG1 antibody Fc domains comprises one or more of the substitutions K360E, K409W, Q347R, D399V, and F405T, numbered according to EU numbering.

15. A formulation comprising the multi-specific binding protein according to claim 1 and a pharmaceutically acceptable carrier.

16. A host cell comprising one or more nucleic acids encoding the multi-specific binding protein according to claim 1.

17. A method of directly and/or indirectly enhancing BCMA-expressing tumor cell death, the method comprising exposing the BCMA-expressing tumor cell and a natural killer cell to the multi-specific binding protein according to claim 1.

18. A method of treating BCMA-expressing cancer, wherein the method comprises administering an effective amount of the multi-specific binding protein according to claim 1 to a patient in need thereof.

19. The method of claim 18, wherein the BCMA-expressing cancer is selected from the group consisting of multiple myeloma, acute myelomonocytic leukemia, T cell lymphoma, acute monocytic leukemia, and follicular lymphoma.

20. The method of claim 18, wherein the BCMA-expressing cancer is multiple myeloma.

* * * * *

SEQUENCE LISTING

```
<160> NUMBER OF SEQ ID NOS: 143

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 2
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105


<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105
```

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95
```

```
Phe Gly Gly Gly Thr Lys Val Glu Ile Lys
            100                 105


<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
            100                 105


<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105
```

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
```

```
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115


<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105


<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
```

115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 14

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Ile
                85                  90                  95

Thr Phe Gly Gly Gly Thr Lys Val Glu Ile Lys
            100                 105
```

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
            100                 105


<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105


<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105


<210> SEQ ID NO 21
```

<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105
```

<210> SEQ ID NO 23
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105


<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105


<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 28
<211> LENGTH: 106
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 28

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105
```

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 29

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 30
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 30

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
```

```
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105


<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 32
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
```

```
                85                  90                  95

Phe Gly Gly Gly Thr Lys Val Glu Ile Lys
            100                 105


<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115


<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105


<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 35

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 36
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Gly Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr His Ser Phe Pro Thr
85 90 95

Phe Gly Gly Gly Thr Lys Val Glu Ile Lys
100 105

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

```
Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105
```

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110
```

```
Val Thr Val Ser Ser
        115


<210> SEQ ID NO 40
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105


<210> SEQ ID NO 41
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Ser Ser Ile Arg His Ala Tyr Tyr Tyr Tyr Gly Met
            100                 105                 110

Asp Val Trp Gly Gln Gly Thr Thr Val Thr Val Ser Ser
        115                 120                 125


<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile

```
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105


<210> SEQ ID NO 45
<211> LENGTH: 121
<212> TYPE: PRT
<213> ORGANISM: Homo sapiens

<400> SEQUENCE: 45

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120


<210> SEQ ID NO 46
<211> LENGTH: 110
<212> TYPE: PRT
<213> ORGANISM: Homo sapiens

<400> SEQUENCE: 46

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110


<210> SEQ ID NO 47
<211> LENGTH: 115
<212> TYPE: PRT
```

<213> ORGANISM: Homo sapiens

<400> SEQUENCE: 47

```
Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115
```

<210> SEQ ID NO 48
<211> LENGTH: 108
<212> TYPE: PRT
<213> ORGANISM: Homo sapiens

<400> SEQUENCE: 48

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60
```

```
Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115


<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Tyr Tyr Ile Asn
1               5


<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Ile Tyr Phe Ala Ser Gly Asn Ser Glu Tyr Asn Gln Lys Phe Thr
1               5                   10                  15

Gly


<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Tyr Asp Tyr Asp Trp Tyr Phe Asp Val
1               5                   10


<210> SEQ ID NO 53
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

```
Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
            100                 105                 110


<210> SEQ ID NO 54
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
            100                 105                 110


<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Ser Ser Gln Ser Leu Val His Ser Asn Gly Asn Thr Tyr Leu His
1               5                   10                  15


<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Val Ser Asn Arg Phe Ser
1               5


<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 57

```
Ala Glu Thr Ser His Val Pro Trp Thr
1               5
```

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

```
Ser Gln Ser Ser Ile Tyr Pro Trp Thr
1               5
```

<210> SEQ ID NO 59
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115
```

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80
```

```
Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110


<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asn Gly Tyr Asp Val Leu Asp Asn Trp Gly
            100                 105                 110

Gln Gly Thr Leu Val Thr Val Ser Ser
        115                 120


<210> SEQ ID NO 62
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys Arg
            100                 105


<210> SEQ ID NO 63
<211> LENGTH: 184
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 63

Met Leu Gln Met Ala Gly Gln Cys Ser Gln Asn Glu Tyr Phe Asp Ser
1 5 10 15

Leu Leu His Ala Cys Ile Pro Cys Gln Leu Arg Cys Ser Ser Asn Thr
20 25 30

Pro Pro Leu Thr Cys Gln Arg Tyr Cys Asn Ala Ser Val Thr Asn Ser
35 40 45

Val Lys Gly Thr Asn Ala Ile Leu Trp Thr Cys Leu Gly Leu Ser Leu
50 55 60

Ile Ile Ser Leu Ala Val Phe Val Leu Met Phe Leu Leu Arg Lys Ile
65 70 75 80

Asn Ser Glu Pro Leu Lys Asp Glu Phe Lys Asn Thr Gly Ser Gly Leu
85 90 95

Leu Gly Met Ala Asn Ile Asp Leu Glu Lys Ser Arg Thr Gly Asp Glu
100 105 110

Ile Ile Leu Pro Arg Gly Leu Glu Tyr Thr Val Glu Glu Cys Thr Cys
115 120 125

Glu Asp Cys Ile Lys Ser Lys Pro Lys Val Asp Ser Asp His Cys Phe
130 135 140

Pro Leu Pro Ala Met Glu Glu Gly Ala Thr Ile Leu Val Thr Thr Lys
145 150 155 160

Thr Asn Asp Tyr Cys Lys Ser Leu Pro Ala Ala Leu Ser Ala Thr Glu
165 170 175

Ile Glu Lys Ser Ile Ser Ala Arg
180

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Ser Phe Ser Gly Tyr Tyr Trp Ser
1 5

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Glu Ile Asp His Ser Gly Ser Thr Asn Tyr Asn Pro Ser Leu Lys Ser
1 5 10 15

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Ala Arg Ala Arg Gly Pro Trp Ser Phe Asp Pro
1 5 10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gly Thr Phe Ser Ser Tyr Ala Ile Ser
1 5

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Ile Ile Pro Ile Phe Gly Thr Ala Asn Tyr Ala Gln Lys Phe Gln
1 5 10 15

Gly

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ala Arg Gly Asp Ser Ser Ile Arg His Ala Tyr Tyr Tyr Tyr Gly Met
1 5 10 15

Asp Val

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Lys Ser Ser Gln Ser Val Leu Tyr Ser Ser Asn Asn Lys Asn Tyr Leu
1 5 10 15

Ala

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Trp Ala Ser Thr Arg Glu Ser 1 5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gln Gln Tyr Tyr Ser Thr Pro Ile Thr
1 5

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Gly Ser Ile Ser Ser Ser Ser Tyr Tyr Trp Gly
1 5 10

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Ser Ile Tyr Tyr Ser Gly Ser Thr Tyr Tyr Asn Pro Ser Leu Lys Ser
1 5 10 15

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Ala Arg Gly Ser Asp Arg Phe His Pro Tyr Phe Asp Tyr
1 5 10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Arg Ala Ser Gln Ser Val Ser Arg Tyr Leu Ala
1 5 10

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Asp Ala Ser Asn Arg Ala Thr
1 5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Gln Gln Phe Asp Thr Trp Pro Pro Thr
1 5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Asp Tyr Ser Ile Asn
1 5

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Trp Ile Asn Thr Glu Thr Arg Glu Pro Ala Tyr Ala Tyr Asp Phe Arg
1 5 10 15

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Asp Tyr Ser Tyr Ala Met Asp Tyr
1 5

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Arg Ala Ser Glu Ser Val Thr Ile Leu Gly Ser His Leu Ile His
1 5 10 15

<210> SEQ ID NO 83

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Ala Ser Asn Val Gln Thr
1               5


<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Gln Ser Arg Thr Ile Pro Arg Thr
1               5


<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asn Tyr Trp Met His
1               5


<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Thr Tyr Arg Gly His Ser Asp Thr Tyr Tyr Asn Gln Lys Phe Lys
1               5                   10                  15

Gly


<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ala Ile Tyr Asn Gly Tyr Asp Val Leu Asp Asn
1               5                   10


<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 88

Ser Ala Ser Gln Asp Ile Ser Asn Tyr Leu Asn
1 5 10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Tyr Thr Ser Asn Leu His Ser
1 5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gln Gln Tyr Arg Lys Leu Pro Trp Thr
1 5

<210> SEQ ID NO 91
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Val Leu Gly Trp Phe Asp Tyr Trp Gly Gln Gly Thr Leu Val
100 105 110

Thr Val Ser Ser
115

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Tyr Pro Pro
85 90 95

Asp Phe Thr Phe Gly Gln Gly Thr Lys Val Glu Ile Lys
100 105

<210> SEQ ID NO 93
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Asn
20 25 30

Ala Met Gly Trp Val Arg Gln Ala Pro Gly Lys Gly Leu Glu Trp Val
35 40 45

Ser Ala Ile Ser Gly Pro Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Val Leu Gly Trp Phe Asp Tyr Trp Gly Gln Gly Thr Leu Val
100 105 110

Thr Val Ser Ser
115

<210> SEQ ID NO 94
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Asp Glu
20 25 30

Tyr Leu Ser Trp Tyr Gln Gln Lys Pro Gly Gln Ala Pro Arg Leu Leu
35 40 45

Ile His Ser Ala Ser Thr Arg Ala Thr Gly Ile Pro Asp Arg Phe Ser
50 55 60

Gly Ser Gly Ser Gly Thr Asp Phe Thr Leu Ala Ile Ser Arg Leu Glu
65 70 75 80

Pro Glu Asp Phe Ala Val Tyr Tyr Cys Gln Gln Tyr Gly Tyr Pro Pro
85 90 95

Asp Phe Thr Phe Gly Gln Gly Thr Lys Val Glu Ile Lys
100 105

<210> SEQ ID NO 95
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asp His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Ala Arg Gly Pro Trp Ser Phe Asp Pro Trp Gly Gln Gly Thr Leu
100 105 110

Val Thr Val Ser Ser
115

<210> SEQ ID NO 96
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Glu Gln Tyr Asp Ser Tyr Pro Thr
85 90 95

Phe Gly Gly Gly Thr Lys Val Glu Ile Lys
100 105

<210> SEQ ID NO 97
<211> LENGTH: 126

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Arg Gly Arg Lys Ala Ser Gly Ser Phe Tyr Tyr Tyr Tyr Gly
100 105 110

Met Asp Val Trp Gly Gln Gly Thr Thr Val Thr Val Ser Ser
115 120 125

<210> SEQ ID NO 98
<211> LENGTH: 113
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

Asp Ile Val Met Thr Gln Ser Pro Asp Ser Leu Ala Val Ser Leu Gly
1 5 10 15

Glu Arg Ala Thr Ile Asn Cys Glu Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Pro Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Tyr Ser Tyr Pro Tyr Thr Phe Gly Gln Gly Thr Lys Leu Glu Ile
100 105 110

Lys

<210> SEQ ID NO 99
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 99

Glu Val Gln Leu Leu Glu Ser Gly Gly Gly Leu Val Gln Pro Gly Gly
1 5 10 15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
        115                 120


<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
            100                 105


<210> SEQ ID NO 101
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
        115                 120


<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105


<210> SEQ ID NO 103
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp Asp His Gly Met Asp
            100                 105                 110

Val Trp Gly Gln Gly Thr Thr Val Thr Val Ser Ser
        115                 120


<210> SEQ ID NO 104
```

<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105
```

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

```
Phe Thr Phe Ser Ser Tyr Ala Met Ser
1               5
```

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

```
Ala Ile Ser Gly Ser Gly Gly Ser Thr Tyr Tyr Ala Asp Ser Val Lys
1               5                   10                  15

Gly
```

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

```
Ala Lys Asp Gly Gly Tyr Tyr Asp Ser Gly Ala Gly Asp Tyr
1               5                   10
```

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Arg Ala Ser Gln Gly Ile Asp Ser Trp Leu Ala
1 5 10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Ala Ala Ser Ser Leu Gln Ser
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Gln Gln Gly Val Ser Tyr Pro Arg Thr
1 5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Phe Thr Phe Ser Ser Tyr Ser Met Asn
1 5

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Ser Ile Ser Ser Ser Ser Ser Tyr Ile Tyr Tyr Ala Asp Ser Val Lys
1 5 10 15

Gly

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Ala Arg Gly Ala Pro Met Gly Ala Ala Ala Gly Trp Phe Asp Pro 1 5 10 15

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Arg Ala Ser Gln Gly Ile Ser Ser Trp Leu Ala
1 5 10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Ala Ala Ser Ser Leu Gln Ser
1 5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Gln Gln Gly Val Ser Phe Pro Arg Thr
1 5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Tyr Thr Phe Thr Gly Tyr Tyr Met His
1 5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Trp Ile Asn Pro Asn Ser Gly Gly Thr Asn Tyr Ala Gln Lys Phe Gln
1 5 10 15

Gly

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Ala Arg Asp Thr Gly Glu Tyr Tyr Asp Thr Asp Asp His Gly Met Asp
1 5 10 15

Val

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Arg Ala Ser Gln Ser Val Ser Ser Asn Leu Ala
1 5 10

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Gly Ala Ser Thr Arg Ala Thr
1 5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Gln Gln Asp Asp Tyr Trp Pro Pro Thr
1 5

<210> SEQ ID NO 123
<211> LENGTH: 121
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Phe Trp Gly Trp Ile Arg Gln Pro Pro Gly Lys Gly Leu Glu
35 40 45

Trp Ile Gly Ser Ile Tyr Tyr Ser Gly Ile Thr Tyr Tyr Asn Pro Ser
50 55 60

Leu Lys Ser Arg Val Thr Ile Ser Val Asp Thr Ser Lys Asn Gln Phe
65 70 75 80

```
Ser Leu Lys Leu Ser Ser Val Thr Ala Ala Asp Thr Ala Val Tyr Tyr
                85                  90                  95

Cys Ala Arg His Asp Gly Ala Thr Ala Gly Leu Phe Asp Tyr Trp Gly
            100                 105                 110

Gln Gly Thr Leu Val Thr Val Ser Ser
        115                 120


<210> SEQ ID NO 124
<211> LENGTH: 108
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Ser Ser Tyr Phe Trp Gly
1               5


<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ile Tyr Tyr Ser Gly Ile Thr Tyr Tyr Asn Pro Ser Leu Lys Ser
1               5                   10                  15


<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127
```

His Asp Gly Ala Thr Ala Gly Leu Phe Asp Tyr
1 5 10

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Gly Gly Asn Asn Ile Gly Ser Lys Ser Val His
1 5 10

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Asp Asp Ser Asp Arg Pro Ser
1 5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Gln Val Trp Asp Ser Ser Ser Asp His Val Val
1 5 10

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Asp Asn Ala Met Gly
1 5

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Ala Ile Ser Gly Pro Gly Ser Ser Thr Tyr Tyr Ala Asp Ser Val Lys
1 5 10 15

<210> SEQ ID NO 133
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 133

Val Leu Gly Trp Phe Asp Tyr
1               5


<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Ala Ser Gln Ser Val Ser Asp Glu Tyr Leu Ser
1               5                   10


<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ser Ala Ser Thr Arg Ala Thr
1               5


<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Gln Tyr Gly Tyr Pro Pro Asp Phe Thr
1               5                   10


<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Tyr Ala Met Ser
1               5


<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ile Ser Gly Ser Gly Gly Ser Thr Tyr Tyr Ala Asp Ser Val Lys
1               5                   10                  15
```

Gly

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Val Leu Gly Trp Phe Asp Tyr
1               5

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Arg Ala Ser Gln Ser Val Ser Ser Ser Tyr Leu Ala
1               5                   10

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Gly Ala Ser Ser Arg Ala Thr
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Gln Gln Tyr Gly Tyr Pro Pro Asp Phe Thr
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Gly Phe Thr Phe Ser Asp Asn Ala Met Gly
1               5                   10